United States Patent [19]

Schoen et al.

[11] Patent Number: 5,726,307
[45] Date of Patent: Mar. 10, 1998

[54] BENZO-FUSED LACTAMS PROMOTE RELEASE OF GROWTH HORMONE

[75] Inventors: William R. Schoen, Edison; Matthew J. Wyvratt, Mountainside, both of N.J.

[73] Assignee: Merck & Co., Inc., Rahway, N.J.

[21] Appl. No.: 356,935

[22] Filed: Dec. 15, 1994

Related U.S. Application Data

[62] Division of Ser. No. 961,008, Oct. 14, 1992, Pat. No. 5,374,721.
[51] Int. Cl.⁶ ............ C07D 285/36; C07D 267/14
[52] U.S. Cl. ............ 540/491; 540/453; 544/52; 544/105
[58] Field of Search .............. 540/491, 455; 544/105, 52

[56] References Cited

U.S. PATENT DOCUMENTS 5,374,721  12/1994  Schoen et al. .............. 540/491

*Primary Examiner*—Robert T. Bond
*Attorney, Agent, or Firm*—J. Eric Thies; David L. Rose

[57] ABSTRACT

There are disclosed certain novel compounds identified as benzo-fused lactams which promote the release of growth hormone in humans and animals. This property can be utilized to promote the growth of food animals to render the production of edible meat products more efficient, and in humans, to increase the stature of those afflicted with a lack of a normal secretion of natural growth hormone. Growth promoting compositions containing such benzo-fused lactams as the active ingredient thereof are also disclosed.

6 Claims, No Drawings

BENZO-FUSED LACTAMS PROMOTE RELEASE OF GROWTH HORMONE

CROSS REFERENCE TO RELATED APPLICATIONS

This application is a division of application Ser. No. 07/961,008, filed Oct. 14, 1992, issuing as U.S. Pat. No. 5,374,721 on Dec. 20, 1994.

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptidyl agents for promoting the release of growth hormone which may be administered parenterally, nasally or by the oral route.

SUMMARY OF THE INVENTION

The instant invention covers certain benzo-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the benzo-fused lactam compounds. It is a further object of this invention to describe procedures for the preparation of such compounds. A still further object is to describe the use of such compounds to increase the secretion of growth hormone in humans and animals. A still further object of this invention is to describe compositions containing the benzo-fused lactam compounds for the use of treating humans and animals so as to increase the level of growth hormone secretions. Further objects will become apparent from a reading of the following description.

DESCRIPTION OF THE INVENTION

The novel benzo-fused lactams of the instant invention are best described in the following structural formula I:

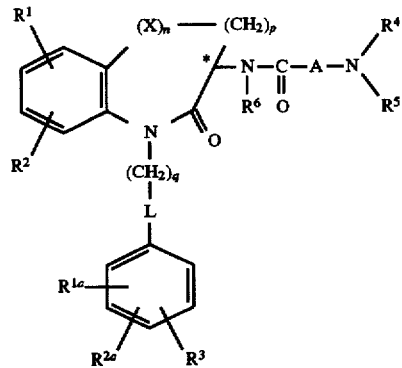

where L is

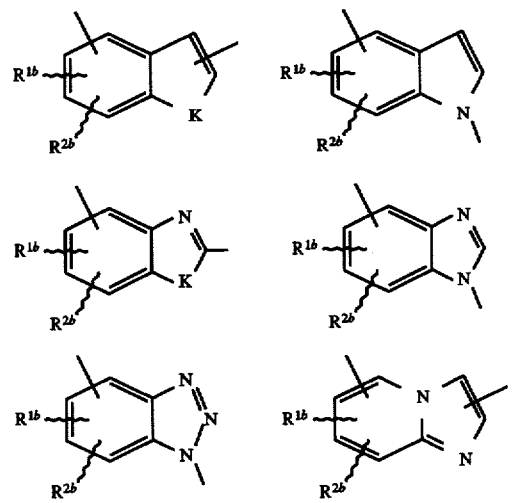

where K is O, S or N—$R^{13}$; and $R^{1b}$ and $R^{2b}$ may be attached to either ring of the benzo-fused heterocycle;

n is 0 or 1;

p is 0 to 3;

q is 0 to 4;

X is C=O, O, S(O)$_m$.

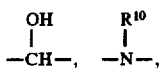

—CH=CH—;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, $C_1$-$C_3$ perfluoroalkoxy, —S(O)$_m R^{7a}$, cyano, nitro, $R^{7b}O(CH_2)_v$—, $R^{7b}COO(CH_2)_v$—, $R^{7b}OCO(CH_2)_v$—, $R^4R^5N(CH_2)_v$—, $R^{7b}CON(R^4)(CH_2)_v$—, $R^4R^5NCO(CH_2)_v$—, phenyl or substituted phenyl where the substituents are from 1 to 3 of halogen, $C_1$-$C_6$ alkyl, $C_1$-$C_6$ alkoxy, or hydroxy; $R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl or substituted phenyl; phenyl or substituted phenyl where the phenyl substituents are from 1 to 3 of halogen, $C_1$-$C_6$ alkyl, $C_1$-$C_6$ alkoxy, or hydroxy and v is 0 to 3;

$R^3$ is hydrogen, $R^9$, $C_1$-$C_6$ alkyl substituted with $R^9$, phenyl substituted with $R^9$, or phenoxy substituted with $R^9$;

$R^9$ is

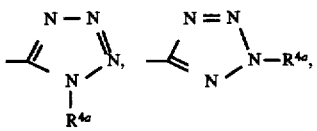

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_v CO$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4R^5NN(R^5)CO(CH_2)_v$—, $R^4R^5NN(R^5)CS(CH_2)_v$—, $R^{7b}CON(R^4)N(R^5)CO(CH_2)_v$—, $R^{7b}CON(R^4)N(R^5)CS(CH_2)_v$—, $R^{7a}CON(OR^{7b})CO(CH_2)_v$—, $R^4N(OR^{7b})CO(CH_2)_v$—, $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CSN(R^{12c})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 3;

$R^{12a}$, $R^{12b}$ and $R^{12c}$ are independently $R^{5a}$, $OR^{5a}$, or $COR^{5a}$; $R^{12a}$ and $R^{12b}$, or $R^{12b}$ and $R^{12c}$, or $R^{13}$ and $R^{12b}$, or $R^{12a}$ and $R^{4b}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3 and $R^1$ and $R^{10}$ are as defined;

$R^{13}$ is $C_1$-$C_3$ perfluoroalkyl, $C_1$-$C_6$ alkyl, substituted $C_1$-$C_6$ alkyl, where the substitutents are hydroxy, —NR$^{10}$R$^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy where $R^{10}$ and $R^{11}$ are independently hydrogen, $C_1$-$C_6$ alkyl, phenyl, phenyl $C_1$-$C_6$ alkyl, $C_1$-$C_5$-alkoxycarbonyl, or $C_1$-$C_5$-alkanoyl-$C_1$-$C_6$ alkyl;

$R^4$, $R^{4a}$, $R^{4b}$, and $R^5$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl, or substituted $C_3$-$C_{10}$ alkynyl where the substituents on the phenyl, alkyl, alkenyl or alkynyl are from 1 to 5 of hydroxy, $C_1$-$C_6$ alkoxy, $C_3$-$C_7$ cycloalkyl, fluoro, $R^1$, $R^2$ independently disubstituted phenyl $C_1$-$C_3$ alkoxy, $R^1$, $R^2$ independently disubstituted phenyl, $C_1$-$C_{20}$ alkanoyloxy, $C_1$-$C_5$ alkoxycarbonyl, carboxy, formyl, or —NR$^{10}$R$^{11}$; or $R^4$ and $R^5$ can be taken together to form —(CH$_2$)$_r$B(CH$_2$)$_s$— where B, r, s, $R^1$, $R^2$, $R^{10}$ and $R^{11}$ are as defined above;

$R^6$ is hydrogen, $C_1$-$C_{10}$ alkyl, phenyl or phenyl $C_1$-$C_{10}$ alkyl;

A is

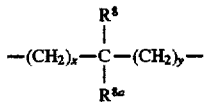

where x and y are independently 0–3;

$R^8$ and $R^{8a}$ are independently hydrogen, $C_1$-$C_{10}$ alkyl, trifluoromethyl, phenyl, substituted $C_1$-$C_{10}$ alkyl where the substituents are from 1 to 3 of imidazolyl, indolyl, hydroxy, fluoro, S(O)$_m R^{7a}$, $C_1$-$C_6$ alkoxy, $C_3$-$C_7$ cycloalkyl, $R^1$, $R^2$ independently disubstituted phenyl $C_1$-$C_3$ alkoxy, $R^1$, $R^2$ independently disubstituted phenyl, $C_1$-$C_5$-alkanoyloxy, $C_1$-$C_5$ alkoxycarbonyl, carboxy, formyl, or —NR$^{10}$R$^{11}$ where $R^1$, $R^2$, $R^{10}$ and $R^{11}$ are as defined above; or $R^8$ and $R^{8a}$ can be taken together to form —(CH$_2$)$_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atom fluorine, chlorine, bromine and iodine.

Certain of the above defined terms may occur more than once in the above formula and upon such occurrence each term shall be defined independently of the other.

Preferred compounds of the instant invention are realized when in the above structural formula:

n is 0 or 1;
p is 0 to 3;
q is 0 to 2;
L is as defined above;
X is O, S(O)$_m$.

—CH=CH—;

m is 0 to 2;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents are from 1 to 3 of halogen, C$_1$–C$_6$ alkyl, C$_1$–C$_6$ alkoxy, or hydroxy;

R$^{7a}$ and R$^{7b}$ are independently hydrogen, C$_1$–C$_3$ perfluoroalkyl, C$_1$–C$_6$ alkyl, substituted C$_1$–C$_6$ alkyl, where the substituents are phenyl; phenyl and v is 0 to 2;

R$^3$ is hydrogen, R$^9$, C$_1$–C$_6$ alkyl substituted with R$^9$, phenyl substituted with R$^9$, or phenoxy substituted with R$^9$;

R$^9$ is

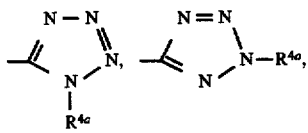

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^4$R$^5$N(CH$_2$)$_v$—, R$^{7b}$CON(R$^4$)(CH$_2$)$_v$—, R$^4$R$^5$NCO(CH$_2$)$_v$—, R$^4$R$^5$NCS(CH$_2$)$_v$—, R$^4$R$^5$NN(R$^5$)CO(CH$_2$)$_v$—, R$^{7b}$CON(R$^4$)N(R$^5$)CO(CH$_2$)$_v$—, R$^4$N(OR$^{7b}$)CO(CH$_2$)$_v$—, R$^{7a}$CON(OR$^{7b}$)CO(CH$_2$)$_v$—, R$^{4b}$R$^{12a}$NCON(R$^{12b}$)(CH$_2$)$_v$—, R$^{4b}$R$^{12a}$NCSN(R$^{12b}$)(CH$_2$)$_v$—, R$^{4b}$R$^{12a}$NN(R$^{12b}$)CON(R$^{12c}$)(CH$_2$)$_v$—, R$^{4b}$R$^{12a}$NN(R$^{12b}$)COO(CH$_2$)$_v$—, R$^{4b}$R$^{12a}$NCOO(CH$_2$)$_v$— or R$^{13}$OCON(R$^{12b}$)(CH$_2$)$_v$—, where v is 0 to 3;

R$^{12a}$, R$^{12b}$ and R$^{12c}$ are independently R$^{5a}$, OR$^{5a}$, or COR$^{5a}$; R$^{12a}$ and R$^{12b}$, or R$^{12b}$ and R$^{12c}$, or R$^{13}$ and R$^{12b}$ or R$^{12a}$ and R$^{4b}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3, R$^1$ is as defined above and R$^{10}$ is hydrogen, C$_1$–C$_6$ alkyl, phenyl C$_1$–C$_6$ alkyl or C$_1$–C$_5$ alkanoyl-C$_1$–C$_6$ alkyl;

R$^{13}$ is C$_1$–C$_3$ perfluoroalkyl, C$_1$–C$_6$ alkyl, substituted C$_1$–C$_6$ alkyl, where the substituents are hydroxy, —NR$^{10}$R$^{11}$, carboxy, phenyl or substituted phenyl; phenyl or substituted phenyl where the substituents on the phenyl are from 1 to 3 of halogen, C$_1$–C$_6$ alkyl, C$_1$–C$_6$ alkoxy or hydroxy; where R$^{10}$ and R$^{11}$ are as defined;

R$^4$, R$^{4a}$, R$^{4b}$, and R$^5$ are independently hydrogen, phenyl, substituted phenyl, C$_1$–C$_{10}$ alkyl, substituted C$_1$–C$_{10}$ alkyl, where the substituents on the alkyl or phenyl are from 1 to 5 of hydroxy, C$_1$–C$_6$ alkoxy, C$_3$–C$_7$ cycloalkyl, fluoro, R$^1$, R$^2$ independently disubstituted phenyl C$_1$–C$_3$ alkoxy, R$^1$, R$^2$ independently disubstituted phenyl, C$_1$–C$_{20}$-alkanoyloxy, C$_1$–C$_5$ alkoxycarbonyl, carboxy or formyl;

R$^4$ and R$^5$ can be taken together to form —(CH$_2$)$_r$B(CH$_2$)$_s$— where B is CHR$^1$, O, S(O)$_m$ or N—R$^{10}$, r and s are independently 1 to 3 and R$^1$ and R$^{10}$ are as defined above;

R$^6$ is hydrogen, C$_1$–C$_{10}$ alkyl or phenyl C$_1$–C$_{10}$ alkyl;

A is

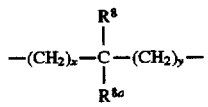

where x and y are independently 0–2;

R$^8$ and R$^{8a}$ are independently hydrogen, C$_1$–C$_{10}$ alkyl, substituted C$_1$–C$_{10}$ alkyl where the substituents are from 1 to 3 of imidazolyl, indolyl, hydroxy, fluoro, S(O)$_m$R$^{7a}$, C$_1$–C$_6$ alkoxy, R$^1$, R$^2$ independently disubstituted phenyl, C$_1$–C$_5$-alkanoyloxy, C$_1$–C$_5$ alkoxycarbonyl, carboxy, formyl or —NR10R$^{11}$ where R$^{10}$ and R$^{11}$ are independently hydrogen, C$_1$–C$_6$ alkyl, or C$_1$–C$_5$ alkanoyl-C$_1$–C$_6$ alkyl; or R$^8$ and R$^{8a}$ can be taken together to form —(CH$_2$)$_t$— where t is 2 to 4; and R$^8$ and R$^{8a}$ can independently be joined to one or both of R$^4$ and R$^5$ to form alkylene bridges between the terminal nitrogen and the alkyl portion of the A group wherein the bridge contains from 1 to 5 carbon atoms; and pharmaceutically acceptable salts thereof.

Additional preferred compounds are realized in the above structural formula when:

n is 0 or 1;
p is 0 to 2;
q is 0 to 2;
L is as defined above;
X is S(O)$_m$ or —CH=CH—;
m is 0 or 1;
R$^1$, R$^2$, R$^{1a}$, R$^{2a}$, R$^{1b}$, and R$^{2b}$ are independently hydrogen, halogen, C$_1$–C$_7$ alkyl, C$_1$–C$_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents are from 1 to 3 of halogen, C$_1$–C$_6$ alkyl, C$_1$–C$_6$ alkoxy, or hydroxy;

R$^{7a}$ and R$^{7b}$ are independently hydrogen, C$_1$–C$_6$ alkyl, substituted C$_1$–C$_6$ alkyl, where the substituents are phenyl and v is 0 to 2;

R$^3$ is hydrogen, R$^9$, C$_1$–C$_6$ alkyl substituted with R$^9$, phenyl substituted with R$^9$, or phenoxy substituted with R$^9$;

R$^9$ is

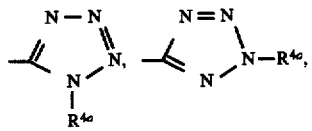

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^4$R$^5$N(CH$_2$)$_v$—, R$^{7b}$CON(R$^4$)(CH$_2$)$_v$—, R$^4$R$^5$NCO(CH$_2$)$_v$—, R$^4$R$^5$NCS(CH$_2$)$_v$—, R$^4$N(OR$^{7b}$)CO(CH$_2$)$_v$—, R$^{7a}$CON(OR$^{7b}$)CO(CH$_2$)$_v$—, R$^{4b}$R$^{12a}$NCON(R$^{12b}$)(CH$_2$)$_v$—, R$^{4b}$R$^{12a}$NCSN(R$^{12b}$)(CH$_2$)$_v$—, R$^{4b}$R$^{12a}$NN(R$^{12b}$)CON(R$^{12c}$)(CH$_2$)$_v$—, R$^{4b}$R$^{12a}$NN(R$^{12b}$)COO(CH$_2$)$_v$—, R$^{4b}$R$^{12a}$NCOO(CH$_2$)$_v$— or R$^{13}$OCON(R$^{12b}$)(CH$_2$)$_v$—, where v is 0 to 2;

R$^{12a}$, R$^{12b}$ and R$^{12c}$ are independently R$^{5a}$ or OR$^{5a}$, R$^{12a}$ and R$^{12b}$, or R$^{12b}$ and R$^{12c}$, or R$^{13}$ and R$^{12b}$ or R$^{12a}$ and R$^{4b}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 2, R$^1$ is as defined above and R$^{10}$ is hydrogen, C$_1$–C$_6$ alkyl or C$_1$–C$_5$ alkanoyl-C$_1$–C$_6$ alkyl;

R$^{13}$ is C$_1$–C$_6$ alkyl, substituted C$_1$–C$_6$ alkyl, where the substituents are phenyl or substituted phenyl; phenyl or substituted phenyl where the substituents on the phenyl are from 1 to 3 of halogen, C$_1$–C$_6$ alkyl, C$_1$–C$_6$ alkoxy or hydroxy;

R$^4$, R$^{4a}$, R$^{4b}$, and R$^5$ are independently hydrogen, C$_1$–C$_{10}$ alkyl, substituted C$_1$–C$_{10}$ alkyl, where the substituents on the alkyl are from 1 to 5 of hydroxy, $C_1$-$C_6$ alkoxy, fluoro, $R^1$, $R^2$ independently disubstituted phenyl, $C_1$-$C_{20}$-alkanoyloxy, $C_1$-$C_5$ alkoxycarbonyl or carboxy;

$R^6$ is hydrogen or $C_1$-$C_{10}$ alkyl;

A is

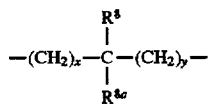

where x and y are independently 0–1;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy; or $R^8$ and $R^{8a}$ can be taken together to form —$(CH_2)_t$— where t is 2; or $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

Still further preferred compounds of the instant invention are realized in the above structural formula when;

n is 0 or 1;
p is 0 to 2;
q is 1;
L is as defined above;
X is $S(O)_m$ or —CH=CH—;
m is 0 or 1;
$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl, substituted $C_1$-$C_6$ alkyl, where the substituents are phenyl and v is 0 or 1;

$R^3$ is hydrogen, $R^9$, or $C_1$-$C_6$ alkyl substituted with $R^9$;
$R^9$ is

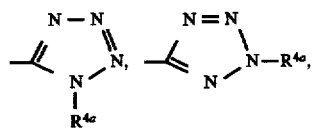

$R^{7b}O(CH_2)_v$—, $R^{7b}COO(CH_2)_v$—, $R^{7b}OCO(CH_2)_v$—, $R^{7b}CO(CH_2)_v$—, $R^{7b}CON(R^4)(CH_2)_v$—, $R^4R^5NCO$ $(CH_2)_v$—, $R^4N(OR^{7b})CO(CH_2)_v$—, $R^{4b}R^{12a}NCON$ $(R^{12b})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO$ $(CH_2)_v$— or $R^{13}OCON(R^{12b})(CH_2)_v$—, where v is 0 to 2;

$R^{12a}$, $R^{12b}$ and $R^{12c}$ are independently $R^{5a}$, $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2. $R^1$ is as defined above and $R^{10}$ is hydrogen, $C_1$-$C_6$ alkyl or $C_1$-$C_5$ alkanoyl-$C_1$-$C_6$ alkyl;

$R^{13}$ is $C_1$-$C_6$ alkyl, substituted $C_1$-$C_6$ alkyl, where the substituents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

$R^4$, $R^{4a}$, $R^{4b}$, and $R^5$ are independently hydrogen, $C_1$-$C_{10}$ alkyl, substituted $C_1$-$C_{10}$ alkyl, where the substituents on the alkyl are from 1 to 3 of hydroxy, $C_1$-$C_3$ alkoxy, fluoro, $R^1$, $R^2$ independently disubstituted phenyl, $C_1$-$C_{20}$ alkanoyloxy, $C_1$-$C_5$ alkoxycarbonyl or carboxy;

$R^6$ is hydrogen;

A is

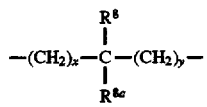

where x and y are independently 0–1;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy; or $R^8$ and $R^{8a}$ can be taken together to form —$(CH_2)_t$— where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

Representative examples of the nomenclature employed are given below:

3-Amino-N-[1-[[3-bromo-2-[2-(1H-tetrazol-5-yl)phenyl]-5-benzofuranyl]methyl]-7-chloro-2,3,4,5-tetrahydro-2-oxo-1H-1-benzazepin-3-yl]-3-methylbutanamide

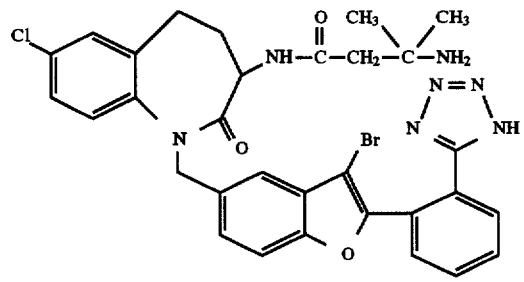

2-[5-[[3-[(2-Amino-2-methyl-1-oxopropyl)amino]-2,3,4,5-tetrahydro-2-oxo-1H-1-benzazepin-1-yl]methyl]benzo[b]thien-2-yl]-N-ethylbenzamide

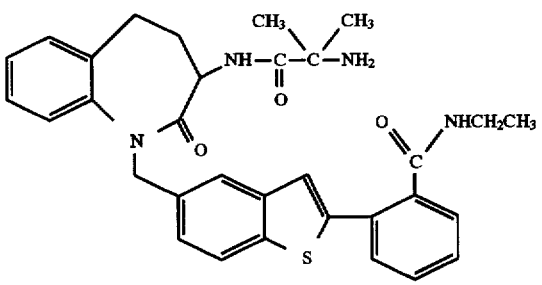

3-[2(R)-Hydroxypropyl]amino-N-[1-[[2-[2-[(methylaminocarbonyl)amino]phenyl]-1H-indol-5-yl]methyl]-2,3,4,5-tetrahydro-2-oxo-1H-1-benzazepin-3-yl]-3-methylbutanamide

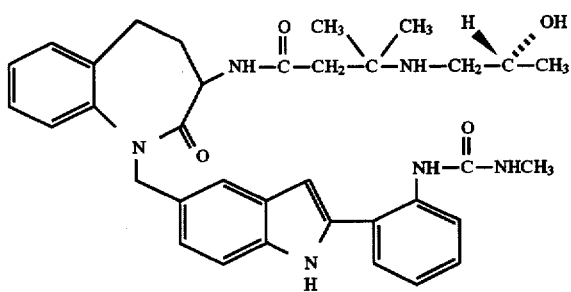

3-[2(S),3-Dihydroxypropyl]amino-N-[5-[[2-[2-(hydroxymethyl)phenyl]-5-benzoxazolyl]methyl]-2,3,4,5-tetrahydro-4-oxo-5H-1,5-benzothiazepin-3-yl]-3-methylbutanamide

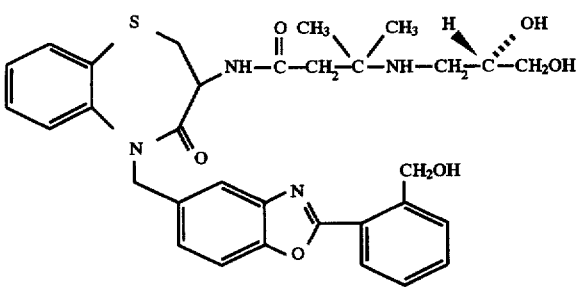

Representative preferred growth hormone releasing compounds of the present invention include the following:

1. 3-Amino-N-[1-[[3-bromo-2-[2-(1H-tetrazol-5-yl)phenyl]-5-benzofuranyl]methyl]-2,3,4,5-tetrahydro-2-oxo-1H-1-benzazepin-3(R)-yl]-3-methylbutanamide
2. 3-Amino-N-[1-[[2-[2-(1H-tetrazol-5-yl)phenyl]-5-benzofuranyl]methyl]-2,3,4,5-tetrahydro-2-oxo-1H-1-benzazepin-3(R)-yl]-3-methylbutanamide
3. 3-[2(R)-Hydroxypropyl]amino-N-[1-[[3-bromo-2-[2-(1H-tetrazol-5-yl)phenyl]-5-benzofuranyl]methyl]-2,3,4,5-tetrahydro-2-oxo-1H-1-benzazepin-3(R)-yl]-3-methylbutanamide
4. 3-[2(S),3-Dihydroxypropyl]amino-N-[1-[[3-bromo-2-[2-(1H-tetrazol-5-yl)phenyl]-5-benzofuranyl]methyl]-2,3,4,5-tetrahydro-2-oxo-1H-1-benzazepin-3(R)-yl]-3-methylbutanamide
5. 2-Amino-N-[1-[[3-bromo-2-[2-(1H-tetrazol-5-yl)phenyl]-5-benzofuranyl]methyl]-2,3,4,5-tetrahydro-2-oxo-1H-1-benzazepin-3(R)-yl]-2-methylpropanamide
6. 3-Amino-N-[1-[[3-bromo-2-[2-(1H-tetrazol-5-yl)phenyl]benzo[b]thien-5-yl]methyl]-2,3,4,5-tetrahydro-2-oxo-1H-1-benzazepin-3(R)-yl]-3-methylbutanamide
7. 3-[2(R)-Hydroxypropyl]amino-N-[1-[[3-bromo-2-[2-(1H-tetrazol-5-yl)phenyl]benzo[b]thien-5-yl]methyl]-2,3,4,5-tetrahydro-2-oxo-1H-1-benzazepin-3(R)-yl]-3-methylbutanamide
8. 3-[2(S),3-Dihydroxypropyl]amino-N-[1-[[3-bromo-2-[2-(1H-tetrazol-5-yl)phenyl]benzo[b]thien-5-yl]methyl]-2,3,4,5-tetrahydro-2-oxo-1H-1-benzazepin-3(R)-yl]-3-methylbutanamide
9. 3-Amino-N-[1-[[2-[2-(1H-tetrazol-5-yl)phenyl]benzo[b]thien-5-yl]methyl]-2,3,4,5-tetrahydro-2-oxo-1H-1-benzazepin-3(R)-yl]-3-methylbutanamide
10. 2-Amino-N-[1-[[3-bromo-2-[2-(1H-tetrazol-5-yl)phenyl]benzo[b]thien-5-yl]methyl]-2,3,4,5-tetrahydro-2-oxo-1H-1-benzazepin-3(R)-yl]-2-methylpropanamide
11. 3-Amino-N-[1-[[3-bromo-2-[2-(1H-tetrazol-5-yl)phenyl]-1H-indol-5-yl]methyl]-2,3,4,5-tetrahydro-2-oxo-1H-1-benzazepin-3(R)-yl]-3-methylbutanamide
12. 3-Amino-N-[1-[[2-[2-(1H-tetrazol-5-yl)phenyl]-1H-indol-5-yl]methyl]-2,3,4,5-tetrahydro-2-oxo-1H-1-benzazepin-3(R)-yl]-3-methylbutanamide
13. 3-[(2(R)-Hydroxypropyl)amino]-N-[1-[[3-bromo-2-[2-(1H-tetrazol-5-yl)phenyl]-1H-indol-5-yl]methyl]-2,3,4,5-tetrahydro-2-oxo-1H-1-benzazepin-3(R)-yl]-3-methylbutanamide
14. 3-[2(S),3-Dihydroxypropyl]amino-N-[1-[[3-bromo-2-[2-(1H-tetrazol-5-yl)phenyl]-1H-indol-5-yl]methyl]-2,3,4,5-tetrahydro-2-oxo-1H-1-benzazepin-3(R)-yl]-3-methylbutanamide
15. 3-Amino-N-[1-[[3-bromo-2-[2-(1H-tetrazol-5-yl)phenyl]-1H-indol-5-yl]methyl]-7-trifluoromethyl-2,3,4,5-tetrahydro-2-oxo-1H-1-benzazepin-3(R)-yl]-3-methylbutanamide
16. (R)-2-[5-[[3-[(3-Amino-3-methyl-1-oxobutyl)amino]-2,3,4,5-tetrahydro-2-oxo-1H-1-benzazepin-1-yl]methyl]-3-bromo-2-benzofuranyl]-N-ethylbenzamide
17. (R)-2-[5-[[3-[(3-Amino-3-methyl-1-oxobutyl)amino]-2,3,4,5-tetrahydro-2-oxo-1H-1-benzazepin-1-yl]methyl]-2-benzofuranyl]-N-ethylbenzamide
18. (R)-2-[5-[[3-[(3-Amino-3-methyl-1-oxobutyl)amino]-7-methoxy-2,3,4,5-tetrahydro-2-oxo-1H-1-benzazepin-1-yl]methyl]-3-bromo-2-benzofuranyl]-N-ethylbenzamide
19. (R)-2-[5-[[3-[[2(R)-Hydroxypropyl]amino]-3-methyl-1-oxobutyl]amino]-2,3,4,5-tetrahydro-2-oxo-1H-1-benzazepin-1-yl]methyl]-3-bromo-2-benzofuranyl]-N-ethylbenzamide
20. (R)-2-[5-[[3-[[3-[2(S),3-Dihydroxypropyl]amino-3-methyl-1-oxobutyl]amino]-2,3,4,5-tetrahydro-2-oxo-1H-1-benzazepin-1-yl]methyl]-3-bromo-2-benzofuranyl]-N-ethylbenzamide
21. (R)-2-[5-[[3-[(3-Amino-3-methyl-1-oxobutyl)amino]-2,3,4,5-tetrahydro-2-oxo-1H-1-benzazepin-1-yl]methyl]-3-bromobenzo[b]thien-2-yl]-N-ethylbenzamide
22. (R)-2-[5-[[3-[(3-Amino-3-methyl-1-oxobutyl)amino]-2,3,4,5-tetrahydro-2-oxo-1H-1-benzazepin-1-yl]methyl]benzo[b]thien-2-yl]-N-ethylbenzamide
23. (R)-2-[5-[[3-[[3-[(2(R)-Hydroxypropyl)amino]-3-methyl-1-oxobutyl]amino]-2,3,4,5-tetrahydro-2-oxo-1H-1-benzazepin-1-yl]methyl]-3-bromobenzo[b]thien-2-yl]-N-ethylbenzamide
24. (R)-2-[5-[[3-[[3-[2(S),3-Dihydroxypropyl]amino-3-methyl-1-oxobutyl]amino]-2,3,4,5-tetrahydro-2-oxo-1H-1-benzazepin-1-yl]methyl]-3-bromobenzo[b]thien-2-yl]-N-ethylbenzamide
25. (R)-2-[5-[[3-[(2-Amino-2-methyl-1-oxopropyl)amino]-2,3,4,5-tetrahydro-2-oxo-1H-1-benzazepin-1-yl]methyl]-3-bromobenzo[b]thien-2-yl]-N-ethylbenzamide 26. (R)-2-[5-[[3-[(3-Amino-3-methyl-1-oxobutyl)amino]-2,3,4,5-tetrahydro-2-oxo-1H-1-benzazepin-1-yl]methyl]-3-bromo-1H-indol-2-yl]-N-ethylbenzamide
27. (R)-2-[5-[[3-[(3-Amino-3-methyl-1-oxobutyl)amino]-2,3,4,5-tetrahydro-2-oxo-1H-1-benzazepin-1-yl]methyl]-1H-indol-2-yl]-N-ethylbenzamide
28. (R)-2-[5-[[3-[[3-[(2(R)-Hydroxypropyl)amino]-3-methyl-1-oxobutyl]amino]-2,3,4,5-tetrahydro-2-oxo-1H-1-benzazepin-1-yl]methyl]-3-bromo-1H-indol-2-yl]-N-ethylbenzamide
29. (R)-2-[5-[[3-[[3-[2(S),3-Dihydroxypropyl]amino-3-methyl-1-oxobutyl]amino]-2,3,4,5-tetrahydro-2-oxo-1H-1-benzazepin-1-yl]methyl]-3-bromo-1H-indol-2-yl]-N-ethylbenzamide
30. (R)-2-[5-[[3-[(2-Amino-2-methyl-1-oxopropyl)amino]-2,3,4,5-tetrahydro-2-oxo-1H-1-benzazepin-1-yl]methyl]-3-bromo-1H-indol-2-yl]-N-ethylbenzamide
31. 3-Amino-N-[1-[[3-bromo-2-[2-[(methylaminocarbonyl)amino]phenyl]-5-benzofuranyl]methyl]-2,3,4,5-tetrahydro-2-oxo-1H-1-benzazepin-3(R)-yl]-3-methylbutanamide
32. 3-Amino-N-[1-[[2-[2-[(methylaminocarbonyl)amino]phenyl]-5-benzofuranyl]methyl]-2,3,4,5-tetrahydro-2-oxo-1H-1-benzazepin-3(R)-yl]-3-methylbutanamide
33. 3-[(2(R)-Hydroxypropyl)amino]-N-[1-[[3-bromo-2-[2-[(methylaminocarbonyl)amino]phenyl]-5-benzofuranyl]methyl]-2,3,4,5-tetrahydro-2-oxo-1H-1-benzazepin-3(R)-yl]-3-methylbutanamide
34. 3-[2(S),3-Dihydroxypropyl]amino-N-[1-[[3-bromo-2-[2-[(methylaminocarbonyl)amino]phenyl]-5-benzofuranyl]methyl]-2,3,4,5-tetrahydro-2-oxo-1H-1-benzazepin-3(R)-yl]-3-methylbutanamide
35. 2-Amino-N-[1-[[3-bromo-2-[2-[(methylaminocarbonyl)amino]phenyl]-5-benzofuranyl]methyl]-2,3,4,5-tetrahydro-2-oxo-1H-1-benzazepin-3(R)-yl]-2-methylpropanamide
36. 3-Amino-N-[1-[[3-bromo-2-[2-[(methylaminocarbonyl)amino]phenyl]-1H-indol-5-yl]methyl]-2,3,4,5-tetrahydro-2-oxo-1H-1-benzazepin-3(R)-yl]-3-methylbutanamide
37. 3-Amino-N-[1-[[2-[2-[(methylaminocarbonyl)amino]phenyl]-1H-indol-5-yl]methyl]-2,3,4,5-tetrahydro-2-oxo-1H-1-benzazepin-3(R)-yl]-3-methylbutanamide
38. 3-[(2(R)-Hydroxypropyl)amino]-N-[1-[[3-bromo-2-[2-[(methylaminocarbonyl)amino]phenyl]-1H-indol-5-yl]methyl]-2,3,4,5-tetrahydro-2-oxo-1H-1-benzazepin-3(R)-yl]-3-methylbutanamide
39. 3-[2(S),3-Dihydroxypropyl]amino-N-[1-[[3-bromo-2-[2-[(methylaminocarbonyl)amino]phenyl]-1H-indol-5-yl]methyl]-2,3,4,5-tetrahydro-2-oxo-1H-1-benzazepin-3(R)-yl]-3-methylbutanamide
40. 2-Amino-N-[1-[[3-bromo-2-[2-[(methylaminocarbonyl)amino]phenyl]-1H-indol-5-yl]methyl]-2,3,4,5-tetrahydro-2-oxo-1H-1-benzazepin-3(R)-yl]-2-methylpropanamide
41. 3-Amino-N-[1-[[3-bromo-2-[2-[(methylaminocarbonyl)amino]phenyl]benzo[b]thien-5-yl]methyl]-2,3,4,5-tetrahydro-2-oxo-1H-1-benzazepin-3(R)-yl]-3-methylbutanamide
42. 3-Amino-N-[1-[[2-[2-[(methylaminocarbonyl)amino]phenyl]benzo[b]thien-5-yl]methyl]-2,3,4,5-tetrahydro-2-oxo-1H-1-benzazepin-3(R)-yl]-3-methylbutanamide
43. 3-[(2(R)-Hydroxypropyl)amino]-N-[1-[[3-bromo-2-[2-[(methylaminocarbonyl)amino]phenyl]benzo[b]thien-5-yl]methyl]-2,3,4,5-tetrahydro-2-oxo-1H-1-benzazepin-3(R)-yl]-3-methylbutanamide
44. 3-[2(S),3-Dihydroxypropyl]amino-N-[1-[[3-bromo-2-[2-[(methylaminocarbonyl)amino]phenyl]benzo[b]thien-5-yl]methyl]-2,3,4,5-tetrahydro-2-oxo-1H-1-benzazepin-3(R)-yl]-3-methylbutanamide
45. 2-Amino-N-[1-[[3-bromo-2-[2-[(methylaminocarbonyl)amino]phenyl]benzo[b]thien-5-yl]methyl]-2,3,4,5-tetrahydro-2-oxo-1H-1-benzazepin-3(R)-yl]-3-methylbutanamide
46. 3-Amino-N-[1-[[2-[2-(1H-tetrazol-5-yl)phenyl]-5-benzoxazolyl]methyl]-2,3,4,5-tetrahydro-2-oxo-1H-1-benzazepin-3(R)-yl]-3-methylbutanamide
47. 3-[(2(R)-Hydroxypropyl)amino]-N-[1-[[2-[2-(1H-tetrazol-5-yl)phenyl]-5-benzoxazolyl]methyl]-2,3,4,5-tetrahydro-2-oxo-1H-1-benzazepin-3(R)-yl]-3-methylbutanamide
48. 3-[2(S),3-Dihydroxypropyl]amino-N-[1-[[2-[2-(1H-tetrazol-5-yl)phenyl]-5-benzoxazolyl]methyl]-2,3,4,5-tetrahydro-2-oxo-1H-1-benzazepin-3(R)-yl]-3-methylbutanamide
49. 2-Amino-N-[1-[[2-[2-(1H-tetrazol-5-yl)phenyl]-5-benzoxazolyl]methyl]-2,3,4,5-tetrahydro-2-oxo-1H-1-benzazepin-3(R)-yl]-2-methylpropanamide
50. 3-[(2(R)-Hydroxypropyl)amino]-N-[1-[[2-[2-(1H-tetrazol-5-yl)phenyl]-5-benzoxazolyl]methyl]-7-trifluoromethyl-2,3,4,5-tetrahydro-2-oxo-1H-1-benzazepin-3(R)-yl]-3-methylbutanamide
51. (R)-2-[5-[[3-[(3-Amino-3-methyl-1-oxobutyl)amino]-2,3,4,5-tetrahydro-2-oxo-1H-1-benzazepin-1-yl]methyl]-2-benzoxazolyl]-N-ethylbenzamide
52. (R)-2-[5-[[3-[[3-[(2(R)-Hydroxypropyl)amino]-3-methyl-1-oxobutyl]amino]-2,3,4,5-tetrahydro-2-oxo-1H-1-benzazepin-1-yl]methyl]-2-benzoxazolyl]-N-ethylbenzamide
53. (R)-2-[5-[[3-[[3-[2(S),3-Dihydroxypropyl]amino-3-methyl-1-oxobutyl]amino]-2,3,4,5-tetrahydro-2-oxo-1H-1-benzazepin-1-yl]methyl]-2-benzoxazolyl]-N-ethylbenzamide
54. (R)-2-[5-[[3-[(2-Amino-2-methyl-1-oxopropyl)amino]-2,3,4,5-tetrahydro-2-oxo-1H-1-benzazepin-1-yl]methyl]-2-benzoxazolyl]-N-ethylbenzamide
55. (R)-2-[5-[[3-[[3-[2(S),3-Dihydroxypropyl]amino-3-methyl-1-oxobutyl]amino]-6-methylthio-2,3,4,5-tetrahydro-2-oxo-1H-1-benzazepin-1-yl]methyl]-2-benzoxazolyl]-N-ethylbenzamide
56. 3-Amino-N-[1-[[2-[2-[(methylaminocarbonyl)amino]phenyl]-5-benzoxazolyl]methyl]-2,3,4,5-tetrahydro-2-oxo-1H-1-benzazepin-3(R)-yl]-3-methylbutanamide
57. 3-[(2(R)-Hydroxypropyl)amino]-N-[1-[[2-[2-[(methylaminocarbonyl)amino]phenyl]-5-benzoxazolyl]methyl]-2,3,4,5-tetrahydro-2-oxo-1H-1-benzazepin-3(R)-yl]-3-methylbutanamide
58. 3-[2(S),3-Dihydroxypropyl]amino-N-[1-[[2-[2-[(methylaminocarbonyl)amino]phenyl]-5-benzoxazolyl]methyl]-2,3,4,5-tetrahydro-2-oxo-1H-1-benzazepin-3(R)-yl]-3-methylbutanamide
59. 2-Amino-N-[1-[[2-[2-[(methylaminocarbonyl)amino]phenyl]-5-benzoxazolyl]methyl]-2,3,4,5-tetrahydro-2-oxo-1H-1-benzazepin-3(R)-yl]-2-methylpropanamide
60. 3-Amino-N-[1-[[2-[2-[(methylaminocarbonyl)amino]phenyl]-5-benzoxazolyl]methyl]-6,7-difluoro-2,3,4,5-tetrahydro-2-oxo-1H-1-benzazepin-3(R)-yl]-3-methylbutanamide
61. 3-Amino-N-[1-[[3-bromo-2-[2-(hydroxymethyl)phenyl]-5-benzofuranyl]methyl]-2,3,4,5-tetrahydro-2-oxo-1H-1-benzazepin-3(R)-yl]-3-methylbutanamide
62. 3-Amino-N-[1-[[2-[2-(hydroxymethyl)phenyl]-5-benzofuranyl]methyl]-2,3,4,5-tetrahydro-2-oxo-1H-1-benzazepin-3(R)-yl]-3-methylbutanamide
63. 3-[(2(R)-Hydroxypropyl)amino]-N-[1-[[3-bromo-2-[2-(hydroxymethyl)phenyl]-5-benzofuranyl]methyl]-2,3,4, 64. 3-[2(S),3-Dihydroxypropyl]amino-N-[1-[[3-bromo-2-[2-(hydroxymethyl)phenyl]-5-benzofuranyl]methyl]-2,3,4,5-tetrahydro-2-oxo-1H-1-benzazepin-3(R)-yl]-3-methylbutanamide
65. 2-Amino-N-[1-[[3-bromo-2-[2-(hydroxymethyl)phenyl]-5-benzofuranyl]methyl]-2,3,4,5-tetrahydro-2-oxo-1H-1-benzazepin-3(R)-yl]-2-methylpropanamide
66. 3-[(2(R)-Hydroxypropyl)amino]-N-[1-[[3-bromo-2-[2-(hydroxymethyl)phenyl]-5-benzofuranyl]methyl]-7-fluoro-2,3,4,5-tetrahydro-2-oxo-1H-1-benzazepin-3(R)-yl]-3-methylbutanamide
67. 3-Amino-N-[1-[[3-bromo-2-[2-(hydroxymethyl)phenyl]benzo[b]thien-5-yl]methyl]-2,3,4,5-tetrahydro-2-oxo-1H-1-benzazepin-3(R)-yl]-3-methylbutanamide
68. 3-Amino-N-[1-[[2-[2-(hydroxymethyl)phenyl]benzo[b]thien-5-yl]methyl]-2,3,4,5-tetrahydro-2-oxo-1H-1-benzazepin-3(R)-yl]-3-methylbutanamide
69. 3-[(2(R)-Hydroxypropyl)amino]-N-[1-[[3-bromo-2-[2-(hydroxymethyl)phenyl]benzo[b]thien-5-yl]methyl]-2,3,4,5-tetrahydro-2-oxo-1H-1-benzazepin-3(R)-yl]-3-methylbutanamide
70. 3-[2(S),3-Dihydroxypropyl]amino-N-[1-[[3-bromo-2-[2-(hydroxymethyl)phenyl]benzo[b]thien-5-yl]methyl]-2,3,4,5-tetrahydro-2-oxo-1H-1-benzazepin-3(R)-yl]-3-methylbutanamide
71. 2-Amino-N-[1-[[3-bromo-2-[2-(hydroxymethyl)phenyl]benzo[b]thien-5-yl]methyl]-2,3,4,5-tetrahydro-2-oxo-1H-1-benzazepin-3(R)-yl]-2-methylpropanamide
72. 3-[(2(R)-Hydroxypropyl)amino]-N-[1-[[3-bromo-2-[2-(hydroxymethyl)phenyl]benzo[b]thien-5-yl]methyl]-6,7-difluoro-2,3,4,5-tetrahydro-2-oxo-1H-1-benzazepin-3(R)-yl]-3-methylbutanamide
73. 3-Amino-N-[1-[[3-bromo-2-[2-(hydroxymethyl)phenyl]-1H-indol-5-yl]methyl]-2,3,4,5-tetrahydro-2-oxo-2H-1-benzazepin-3(R)-yl]-3-methylbutanamide
74. 3-Amino-N-[1-[[2-[2-(hydroxymethyl)phenyl]-1H-indol-5-yl]methyl]-2,3,4,5-tetrahydro-2-oxo-1H-1-benzazepin-3(R)-yl]-3-methylbutanamide
75. 3-[(2(R)-Hydroxypropyl)amino-N-[1-[[3-bromo-2-[2-(hydroxymethyl)phenyl]-1H-indol-5-yl]methyl]-2,3,4,5-tetrahydro-2-oxo-1H-1-benzazepin-3(R)-yl]-3-methylbutanamide
76. 3-[2(S),3-Dihydroxypropyl]amino-N-[1-[[3-bromo-2-[2-(hydroxymethyl)phenyl]-1H-indol-5-yl]methyl]-2,3,4,5-tetrahydro-2-oxo-1H-1-benzazepin-3(R)-yl]-3-methylbutanamide
77. 2-Amino-N-[1-[[3-bromo-2-[2-(hydroxymethyl)phenyl]-1H-indol-5-yl]methyl]-2,3,4,5-tetrahydro-2-oxo-1H-1-benzazepin-3(R)-yl]-2-methylpropnamide
78. 3-[2(S),3-Dihydroxypropyl]amino-N-[1-[[3-bromo-2-[2-(hydroxymethyl)phenyl]-1H-indol-5-yl]methyl]-7-methylthio-2,3,4,5-tetrahydro-2-oxo-1H-1-benzazepin-3(R)-yl]-3-methylbutanamide
79. 3-Amino-N-[1-[[2-[2-(1H-tetrazol-5-yl)phenyl]-5-benzoxazolyl]methyl]-2,3,4,5-tetrahydro-2-oxo-1H-1-benzazepin-3(R)-yl]-3-methylbutanamide
80. 3-[(2(R)-Hydroxypropyl)amino]-N-[1-[[2-[2-(1H-tetrazol-5-yl)phenyl]-5-benzoxazolyl]methyl]-2,3,4,5-tetrahydro-2-oxo-1H-1-benzazepin-3(R)-yl]-3-methylbutanamide
81. 3-[2(S),3-Dihydroxypropyl]amino-N-[1-[[2-[2-(1H-tetrazol-5-yl)phenyl]-5-benzoxazolyl]methyl]-2,3,4,5-tetrahydro-2-oxo-1H-1-benzazepin-3(R)-yl]-3-methylbutanamide
82. 2-Amino-N-[1-[[2-[2-(1H-tetrazol-5-yl)phenyl]-5-benzoxazolyl]methyl]-2,3,4,5-tetrahydro-2-oxo-1H-1-benzazepin-3(R)-yl]-2-methylpropanamide
83. 3-[(2(R)-Hydroxypropyl)amino]-N-[1-[[2-[2-(1H-tetrazol-5-yl)phenyl]-5-benzoxazolyl]methyl]-7-trifluoromethyl-2,3,4,5-tetrahydro-2-oxo-1H-1-benzazepin-3(R)-yl]-benzazepin-3(R)-yl]-3-methylbutanamide
84. 3-Amino-N-[5-[[3-bromo-2-[2-(1H-tetrazol-5-yl)phenyl]-5-benzofuranyl]methyl]-2,3,4,5-tetrahydro-4-oxo-5H-1,5-benzothiazepin-3(S)-yl]-3-methylbutanamide
85. 3-[2(R)-Hydroxypropyl]amino-N-[5-[[3-bromo-2-[2-(1H-tetrazol-5-yl)phenyl]-5-benzofuranyl]methyl]-2,3,4,5-tetrahydro-4-oxo-5H-1,5-benzothiazepin-3(S)-yl]-3-methylbutanamide
86. 3-Amino-N-[5-[[3-bromo-2-[2-(1H-tetrazol-5-yl)phenyl]benzo[b]thien-5-yl]methyl]-2,3,4,5-tetrahydro-4-oxo-5H-1,5-benzothiazepin-3(S)-yl]-3-methylbutanamide
87. 3-[2(R)-Hydroxypropyl]amino-N-[5-[[3-bromo-2-[2-(1H-tetrazol-5-yl)phenyl]benzo[b]thien-5-yl]methyl]-2,3,4,5-tetrahydro-4-oxo-5H-1,5-benzothiazepin-3(S)-yl]-3-methylbutanamide
88. 3-Amino-N-[5-[[3-bromo-2-[2-(1H-tetrazol-5-yl)phenyl]-1H-indol-5-yl]methyl]-2,3,4,5-tetrahydro-4-oxo-5H-1,5-benzothiazepin-3(S)-yl]-3-methylbutanamide
89. 3-[(2(R)-Hydroxypropyl)amino]-N-[5-[[3-bromo-2-[2-(1H-tetrazol-5-yl)phenyl]-1H-indol-5-yl]methyl]-2,3,4,5-tetrahydro-4-oxo-5H-1,5-benzothiazepin-3(S)-yl]-3-methylbutanamide
90. (R)-2-[5-[[3-[(3-Amino-3-methyl-1-oxobutyl)amino]-2,3,4,5-tetrahydro-4-oxo-5H-1,5-benzothiazepin-5-yl]methyl]-3-bromo-2-benzofuranyl]-N-ethylbenzamide
91. (R)-2-[5-[[3-[[2(R)-Hydroxypropyl]amino]-3-methyl-1-oxobutyl]amino]-2,3,4,5-tetrahydro-4-oxo-5H-1,5-benzothiazepin-1-yl]methyl]-3-bromo-2-benzofuranyl]-N-ethylbenzamide
92. (R)-2-[5-[[3-[[2(R)-Hydroxypropyl]amino]-3-methyl-1-oxobutyl]amino]-2,3,4,5-tetrahydro-4-oxo-5H-1,5-benzothiazepin-1-yl]methyl]-3-bromo-2-benzofuranyl]-N-ethylbenzamide
93. (R)-2-[5-[[3-[(3-Amino-3-methyl-1-oxobutyl)amino]-2,3,4,5-tetrahydro-4-oxo-5H-1,5-benzothiazepin-1-yl]methyl]-3-bromobenzo[b]thien-2-yl]-N-ethylbenzamide
94. (R)-2-[5-[[3-[[2(R)-Hydroxypropyl)amino]-3-methyl-1-oxobutyl]amino]-2,3,4,5-tetrahydro-4-oxo-5H-1,5-benzothiazepin-1-yl]methyl]-3-bromobenzo[b]thien-2-yl]-N-ethylbenzamide
95. (R)-2-[5-[[3-[(3-Amino-3-methyl-1-oxobutyl)amino]-2,3,4,5-tetrahydro-4-oxo-5H-1,5-benzothiazepin-1-yl]methyl]-3-bromo-1H-indol-2-yl]-N-ethylbenzamide
96. (R)-2-[5-[[3-[[2(R)-Hydroxypropyl)amino]-3-methyl-1-oxobutyl]amino]-2,3,4,5-tetrahydro-4-oxo-5H-1,5-benzothiazepin-1-yl]methyl]-3-bromo-1H-indol-2-yl]-N-ethylbenzamide
97. 3-Amino-N-[5-[[3-bromo-2-[2-[(methylaminocarbonyl)amino]phenyl]-5-benzofuranyl]methyl]-2,3,4,5-tetrahydro-4-oxo-5H-1,5-benzothiazepin-3(S)-yl]-3-methylbutanamide
98. 3-[(2(R)-Hydroxypropyl)amino]-N-[5-[[3-bromo-2-[2-[(methylaminocarbonyl)amino]phenyl]-5-benzofuranyl]methyl]-2,3,4,5-tetrahydro-4-oxo-5H-1,5-benzothiazepin-3(S)-yl]-3-methylbutanamide
99. 3-Amino-N-[5-[[3-bromo-2-[2-[(methylaminocarbonyl)amino]phenyl]-1H-indol-5-yl]methyl]-2,3,4,5-tetrahydro-4-oxo-5H-1,5-benzothiazepin-3(S)-yl]-3-methylbutanamide
100. 3-[(2(R)-Hydroxypropyl)amino]-N-[5-[[3-bromo-2-[2-[(methylaminocarbonyl)amino]phenyl]-1H-indol-5-yl]

methyl]-2,3,4,5-tetrahydro-4-oxo-5H-1,5-benzothiazepin-3(S)-yl]-3-methylbutanamide 101. 3-Amino-N-[5-[[3-bromo-2-[2-[(methylaminocarbonyl)amino]phenyl]benzo[b]thien-5-yl]methyl]-2,3,4,5-tetrahydro-4-oxo-5H-1,5-benzothiazepin-3(S)-yl]-3-methylbutanamide 102. 3-[(2(R)-Hydroxypropyl)amino]-N-[5-[[3-bromo-2-[2-[(methylaminocarbonyl)amino]phenyl]benzo[b]thien-5-yl]methyl]-2,3,4,5-tetrahydro-4-oxo-5H-1,5-benzothiazepin-3(S)-yl]-3-methylbutanamide 103. 3-[(2(R)-Hydroxypropyl)amino]-N-[5-[[2-[2-(1H-tetrazol-5-yl)phenyl]-5-benzoxazolyl]methyl]-2,3,4,5-tetrahydro-4-oxo-5H-1,5-benzothiazepin-3(S)-yl]-3-methylbutanamide 104. (R)-2-[5-[[3-[[3-[(2(R)-Hydroxypropyl)amino]-3-methyl-1-oxobutyl]amino]-2,3,4,5-tetrahydro-4-oxo-5H-1,5-benzothiazepin-1-yl]methyl]-2-benzoxazolyl]-N-ethylbenzamide 105. 3-[(2(R)-Hydroxypropyl)amino]-N-[5-[[3-bromo-2-[2-(hydroxymethyl)phenyl]-5-benzofuranyl]methyl]-2,3,4,5-tetrahydro-4-oxo-5H-1,5-benzothiazepin-3(S)-yl]-3-methylbutanamide 106. 3-[(2(R)-Hydroxypropyl)amino]-N-[5-[[2-[2-[(methylaminocarbonyl)amino]phenyl]-5-benzoxazolyl]methyl]-2,3,4,5-tetrahydro-4-oxo-5H-1,5-benzothiazepin-3(S)-yl]-3-methylbutanamide 107. 2-Amino-N-[5-[[3-bromo-2-[2-(hydroxymethyl)phenyl]-5-benzofuranyl]methyl]-2,3,4,5-tetrahydro-4-oxo-5H-1,5-benzothiazepin-3(S)-yl]-2-methylpropanamide 108. 3-[(2(R)-Hydroxypropyl)amino]-N-[5-[[3-bromo-2-[2-(hydroxymethyl)phenyl]benzo[b]thien-5-yl]methyl]-2,3,4,5-tetrahydro-4-oxo-5H-1,5-benzothiazepin-3(S)-yl]-3-methylbutanamide 109. 2-Amino-N-[5-[[3-bromo-2-[2-(hydroxymethyl)phenyl]benzo[b]thien-5-yl]methyl]-2,3,4,5-tetrahydro-4-oxo-5H-1,5-benzothiazepin-3(S)-yl]-2-methylpropanamide 110. 3-[(2(R)-Hydroxypropyl)amino-N-[5-[[3-bromo-2-[2-(hydroxymethyl)phenyl]-1H-indol-5-yl]methyl]-2,3,4,5-tetrahydro-4-oxo-5H-1,5-benzothiazepin-3(S)-yl]-3-methylbutanamide 111. 3-[(2(R)-Hydroxypropyl)amino]-N-[1-[[2-[2-(1H-tetrazol-5-yl)phenyl]-5-benzoxazolyl]methyl]-2,3,4,5-tetrahydro-4-oxo-5H-1,5-benzothiazepin-3(S)-yl]-3-methylbutanamide The compounds of the instant invention all have at least one asymmetric center as noted by the asterisk in structural Formulae I and Ia. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the 3-amino substituent is above the plane of the structure, as seen in Formula Ia, is more active and thus more preferred over the compound in which the 3-amino substituent is below the plane of the structure. This center will be designated according to the R/S rules as either R or S depending upon the value of X.

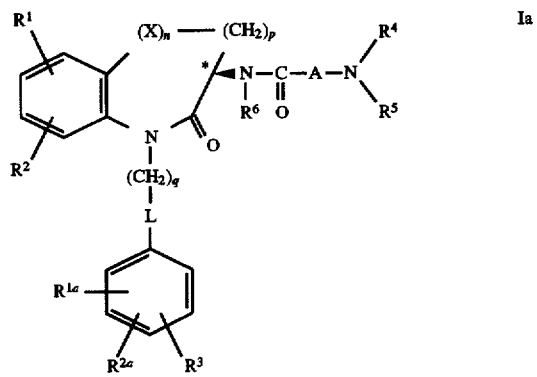

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

The compounds (I) of the present invention are prepared from aminolactam intermediates such as those of formula II. The preparation of these intermediates is described in the following reaction Schemes.

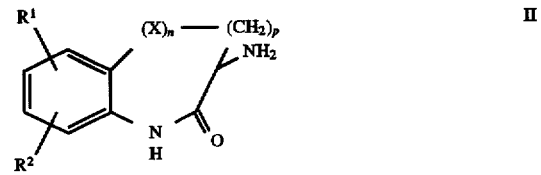

Benzo-fused lactams 3 wherein the lactam is a seven-membered ring are conveniently prepared from substituted tetralones 2 using known procedures. The substituted tetralones are, in some cases, commercially available or are prepared from a suitably substituted derivative of 4-phenylbutyric acid 1. Cyclization of 1 can be achieved by a number of methods well known in the literature including treatment with polyphosphoric acid at elevated temperatures as shown in Scheme 1.

SCHEME 1

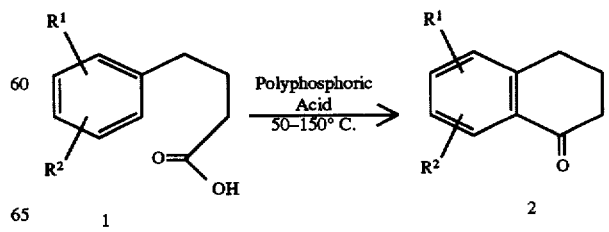

-continued
SCHEME 1

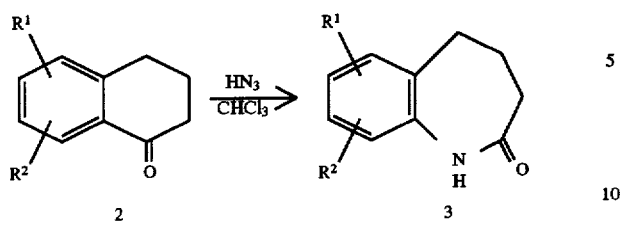

Conversion of substituted tetralones 2 to benzolactams 3 can be achieved by a number of methods familiar to those skilled in the art. A suitable method involves the use of hydrazoic acid (Schmidt reaction) to form the substituted benzolactam 3.

Benzo-fused lactams wherein the lactam is an eight-membered ring (6) are prepared as described by D. H. Jones, et al, J. Chem. Soc. C, 2176–2181 (1969) by an analogous series of transformations starting from a substituted derivative of 5-phenylpentanoic acid 4 as shown in Scheme 2.

SCHEME 2

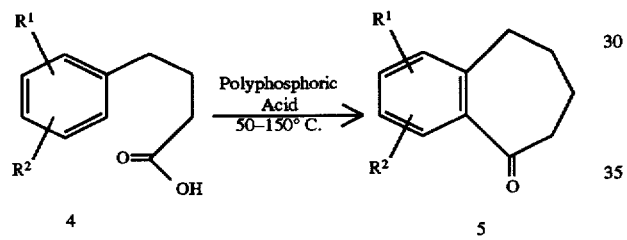

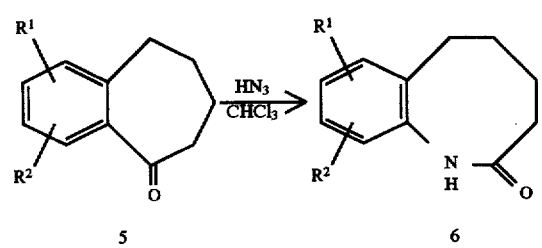

As shown in Scheme 3, 3-aminobenzolactam analogs wherein the lactam is a six-membered ring (11) are prepared from a substituted derivative of 2-nitrobenzyl chloride (or bromide) 7 by the method of A. L. Davis, et al, Arch. Biochem. Biophys, 102, 48–51 (1963) and references cited therein.

SCHEME 3

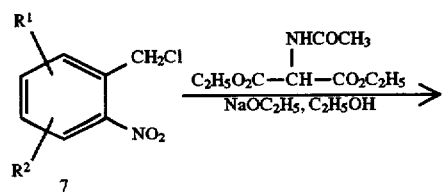

-continued
SCHEME 3

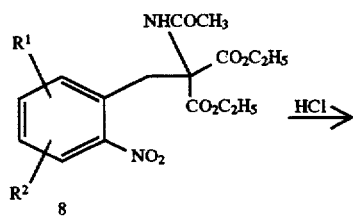

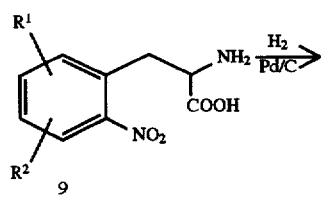

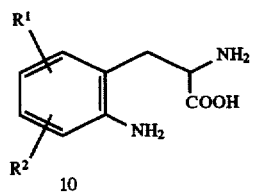

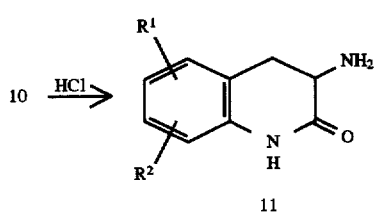

Conversion of substituted benzo-fused lactams to the requisite 3-amino derivatives can be achieved by a number of methods familiar to those skilled in the art, including those described by Watthey, et al, J. Med. Chem., 28, 1511–1516 (1985) and references cited therein. One common route proceeds via the intermediacy of a 3-halo (chloro, bromo or iodo) intermediate which is subsequently displaced by a nitrogen nucleophile, typically azide. A useful method of forming the 3-iodobenzolactam intermediate 12 involves treating the benzolactam with two equivalents each of iodotrimethylsilane and iodine at low temperature, as illustrated in Scheme 4 for the seven-membered ring analog 3.

SCHEME 4

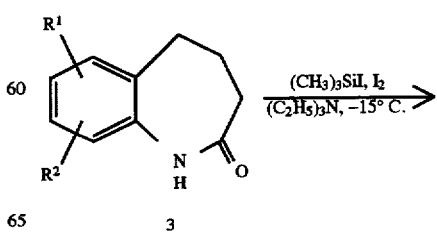

-continued
SCHEME 4

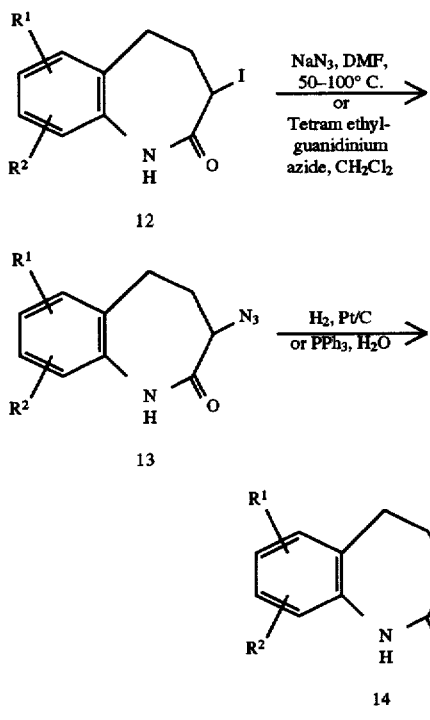

Elaboration of the iodo-benzolactams to the desired aminolactam intermediates II is achieved by a two-step procedure illustrated in Scheme 4. Typically, iodo-benzolactams 12 are treated with sodium azide in N,N-dimethylformamide at 50°–100° C. to give the 3-azido derivatives 13. Alternatively, tetramethylguanidinium azide in a solvent such as methylene chloride can be employed to achieve similar results. Hydrogenation with a metal catalyst, such as platinum on carbon, or alternatively, treatment with triphenylphosphine in wet toluene, results in formation of the amine derivative 14. Formation of the analogous derivatives of the eight-membered benzolactams is also achieved by the routes shown in Scheme 4.

Chiral aminobenzolactams are obtained by resolution of the racemates by classical methods familiar to those skilled in the art. For example, resolution can be achieved by formation of diastereomeric salts of the racemic amines with optically active acids such as D- and L-tartaric acid. Determination of absolute stereochemistry can be achieved in a number of ways including X-ray analysis of a suitable crystalline derivative.

A useful preparation of the chiral intermediate 19 is shown in Scheme 5.

SCHEME 5

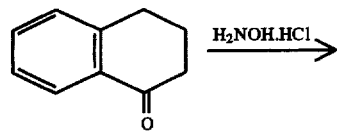

-continued
SCHEME 5

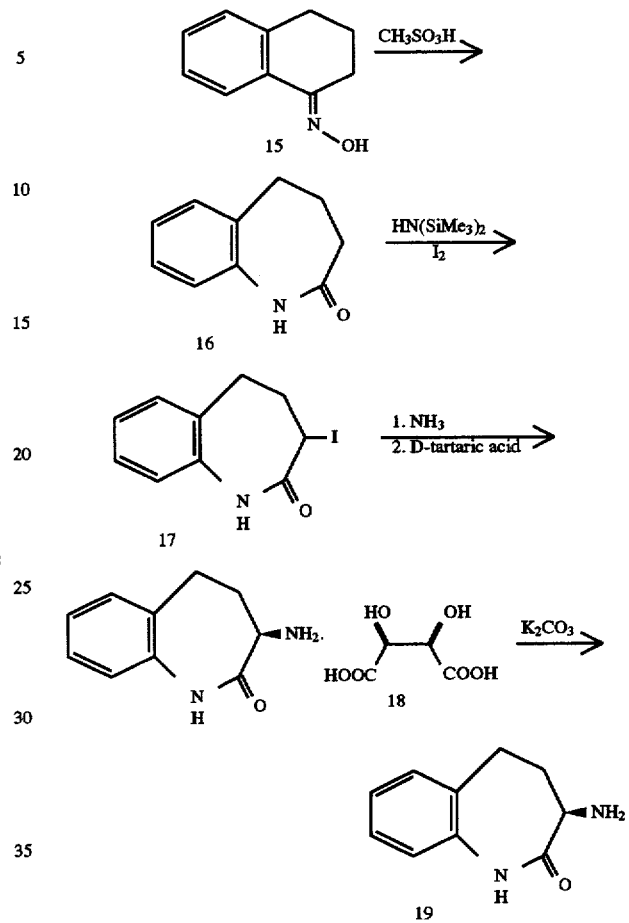

Conversion of 1-tetralone to the seven-membered benzolactam 16 is achieved by Beckman rearrangement of the intermediate oxime 15. Treatment of 16 with iodine and hexamethyldisilazane gives the 3-iodo derivative 17 which is sequentially treated with ammonia and D-tartaric acid to give the diastereomeric D-tartrate salt 18 after recrystallization. Liberation of the free amine 19 is achieved by neutralization of the D-tartrate salt with potassium carbonate followed by extractive isolation.

Intermediates of Formula II wherein X is a sulfur atom are prepared by methods described in the literature and known to those skilled in the art. As illustrated in Scheme 6, the seven-membered ring analog 27 is prepared from a protected derivative of cysteine 21 by the method of Slade, et al., J. Med. Chem., 28, 1517–1521 (1985) and references cited therein (CBz=benzyloxycarbonyl).

SCHEME 6

21
-continued
SCHEME 6

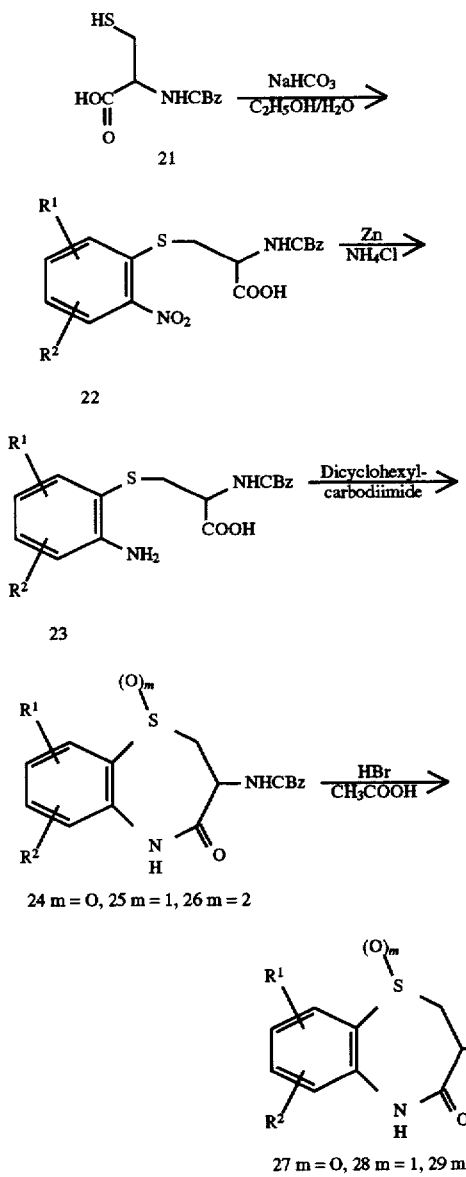

Sulfoxide and sulfone intermediates 28 and 29 are prepared by oxidation of 24 with various oxidants such as sodium periodate or meta-chloroperbenzoic acid. Eight-membered ring intermediates of Formula II wherein X is sulfur can be prepared by an analogous route starting from derivatives of homo-cysteine.

Intermediates of Formula II wherein X is an oxygen atom are prepared by methods described in the literature and known to those skilled in the art. For example, the seven-membered ring analog 26 can be prepared from a substituted derivative of 3-(2-nitrophenoxy)propanoic acid 30 by the method of J. Ott, Arch. Pharm. (Weinheim, Ger.), 323(9), 601–603 (1990).

22
SCHEME 7

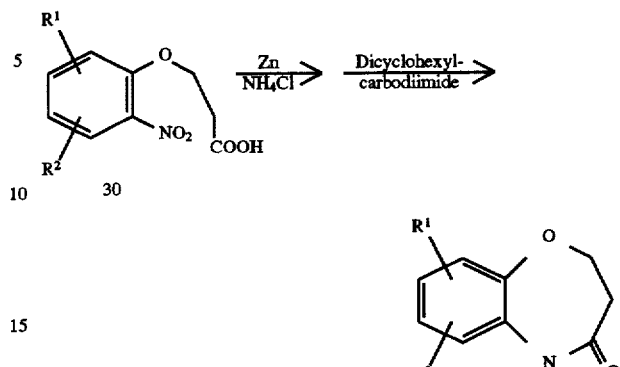

Six-membered ring analogs wherein X is oxygen (33) may be prepared by reaction of a substituted derivative of 2-aminophenol 32 with chloroacetyl chloride by the method of Huang and Chan, Synthesis, 10, 851 (1984) and references cited therein. Subsequent incorporation of an amino group at the 3 position of either 31 or 33 is achieved by the methods described in Scheme 4.

SCHEME 8

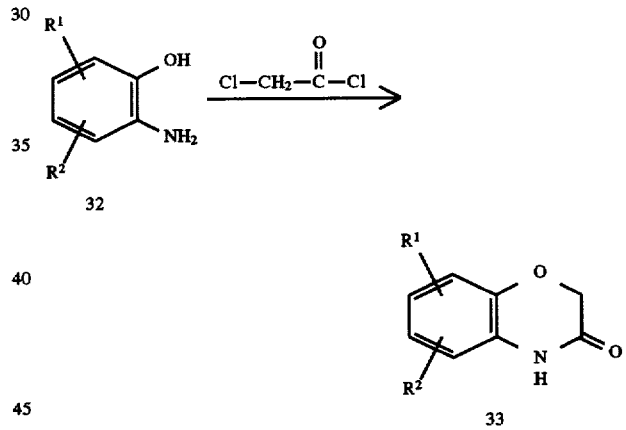

Seven-membered ring analogs of Formula II wherein X is C=O can be prepared from derivatives of tryptophan as described in the Australian Journal of Chemistry, 33, 633–640 (1980). Seven-membered ring analogs of Formula II wherein X is CH=CH can be prepared from the aforementioned analogs wherein X is C=O. Treatment of 34 with chemical reducing agents such as sodium borohydride in a polar solvent such as methanol or ethanol results in reduction to give the secondary alcohol derivative 35 (X=CHOH).

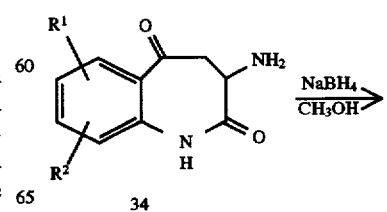

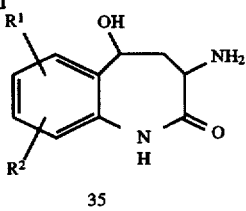

35

Dehydration of 35 can be achieved by several methods decribed in the literature and familiar to those skilled in the art. For example, treatment of 35 in an inert solvent, such as benzene, with a strong acid such as p-toluenesulfonic acid, will result in dehydration to the unsaturated analog 36.

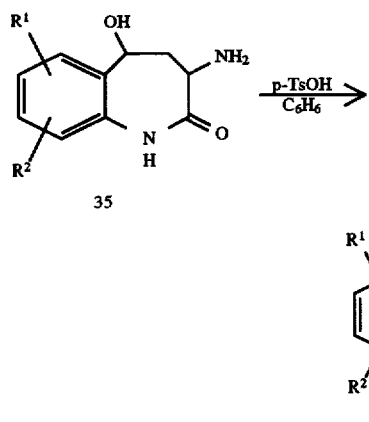

Intermediates of formula II can be further elaborated to new intermediates (formula III) which are substituted on the amino group (Scheme 9). Reductive alkylation of II with an aldehyde is carried out under conditions known in the art; for example, by catalytic hydrogenation with hydrogen in the presence of platinum, palladium or nickel catalysts or with chemical reducing agents such as sodium cyanoborohydride in an inert solvent such as methanol or ethanol.

SCHEME 9

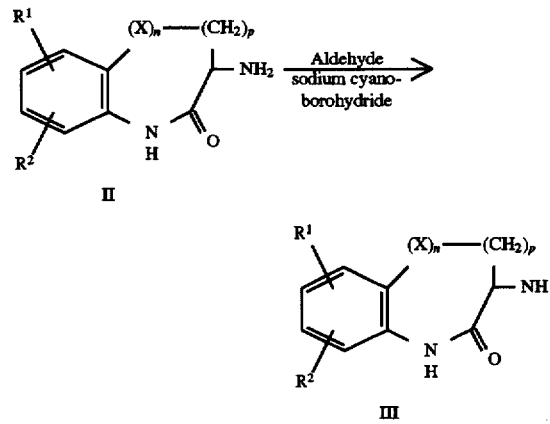

Attachment of the amino acid sidechain to intermediates of formula III is accomplished by the route shown in Scheme 10. Coupling is conveniently carried out by the use of an appropriately protected amino acid derivative, such as that illustrated by formula IV, and a coupling reagent such as benzotriazol-1-yloxytris(dimethylamino)phosphonium hexafluorophosphate ("BOP") in an inert solvent such as methylene chloride. Separation of unwanted side products, and purification of intermediates is achieved by chromatography on silica gel, employing flash chromatography (W. C. Still, M. Kahn and A. Mitra, J. Org. Chem., 43, 2923 (1978)) or by medium pressure liquid chromatography.

SCHEME 10

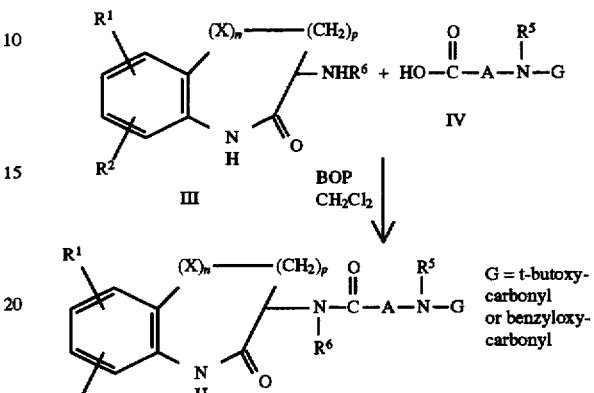

The protected amino acid derivatives IV are, in many cases, commercially available in t-butoxycarbonyl (BOC) or benzyloxycarbonyl (CBz) forms. A useful method to prepare the preferred sidechain 41 is shown in Scheme 11.

SCHEME 11

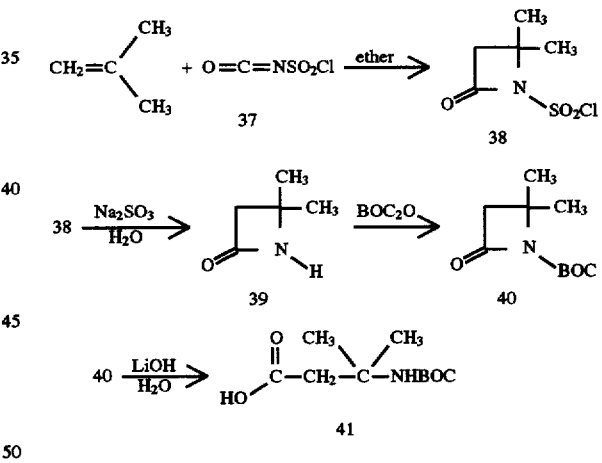

Reaction of isobutylene with N-chlorosulfonylisocyanate 37 in diethyl ether gives the azetidinone derivative 38. Removal of the chlorosulfonyl group with aqueous sodium sulfite followed by reaction with di-t-butyl-dicarbonate gives the BOC-protected intermediate 40. Alkaline hydrolysis gives the protected amino acid derivative 41 in good overall yield.

Intermediates of formula VII can be prepared as shown in Scheme 12 by treatment of the desired lactam intermediate V with an alkylating agent VI, wherein Y is a good leaving group such as Cl, Br, I, O-methanesulfonyl or O-(p-toluenesulfonyl). Alkylation of intermediates of formula V is conveniently carried out in anhydrous dimethyl formamide (DMF) in the presence of bases such as sodium hydride or potassium t-butoxide for a period of 0.5 to 24 hours at temperatures of 20°–100° C. Substituents on the alkylating agent VI may need to be protected during alkylation. A description of such protecting groups may be found in: *Protective Groups in Organic Synthesis*, T. W. Greene, John Wiley and Sons, New York, 1981.

SCHEME 12

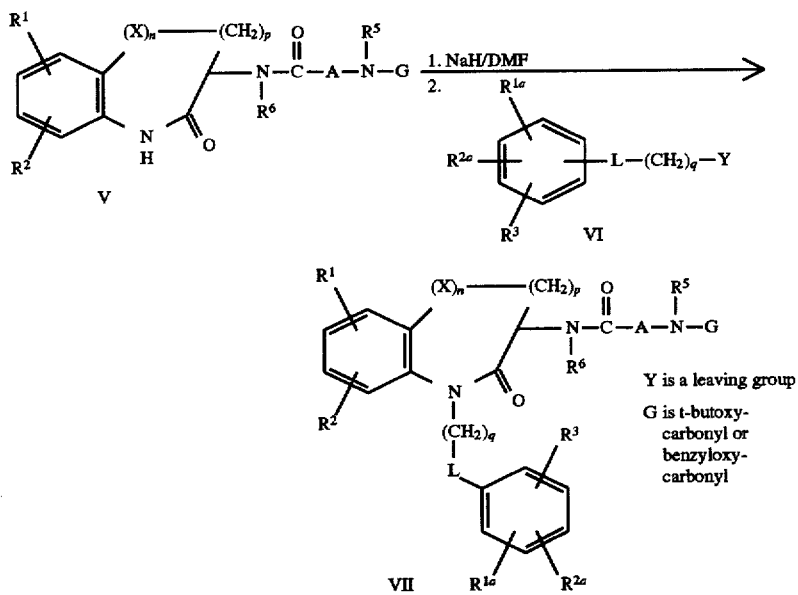

Y is a leaving group

G is t-butoxy-
carbonyl or
benzyloxy-
carbonyl

Alkylating agents VI containing the appropriate benzo-fused heterocyclic linkage L are prepared from the corresponding methyl derivatives by methods described in the chemical literature and familiar to one skilled in the art. Compounds of formula VI wherein L is a substituted benzothiophene or benzofuran containing the aryl substituent at C-2 (45), are prepared as shown in Scheme 13. Reaction of 42 with 43 gives the benzo-fused product 44 directly. Conversion to the requisite alkylating agent 45 is achieved by bromination with N-bromosuccinimide in an inert solvent such as carbon tetrachloride using a free radical initiator such as azobisisobutyronitrile (AIBN) at elevated temperature. Reaction with compounds of formula V is then carried out according to the conditions described in Scheme 12.

SCHEME 13

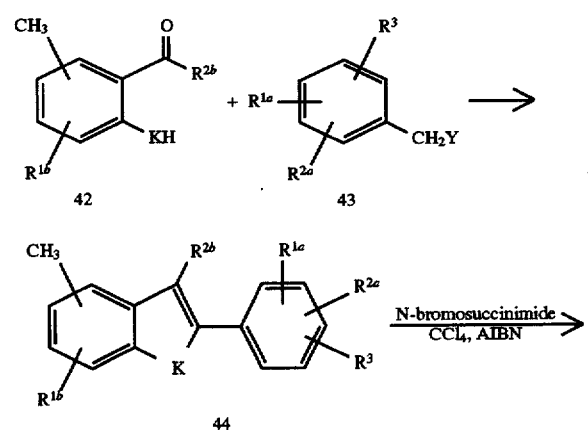

-continued
SCHEME 13

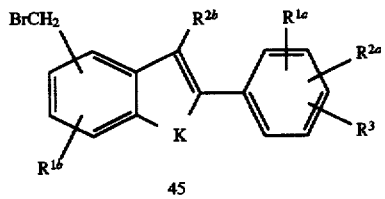

K is O or S
Y is a leaving group

An alternative route to 2-aryl substituted benzothiophene, benzofuran or indole intermediates 49 is shown in Scheme 14. Intermediate 46, containing a hydrogen atom at C-2, can be metallated by treatment with a strong base, such as n-butyllithium. Reaction of the metallated intermediate with trimethylborate, followed by aqueous workup, gives the 2-substituted boronic acid 47. Treatment of 47 with the bromo (or iodo) benzene derivative 48 in the presence of a transition metal catalyst, such as tetrakis (triphenylphosphine)palladium(0), gives the coupled product 49.

SCHEME 14

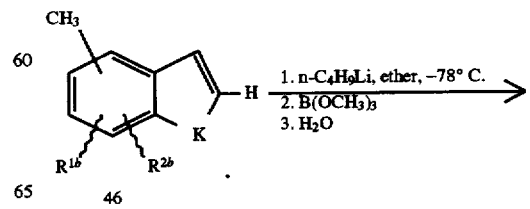

SCHEME 14 -continued

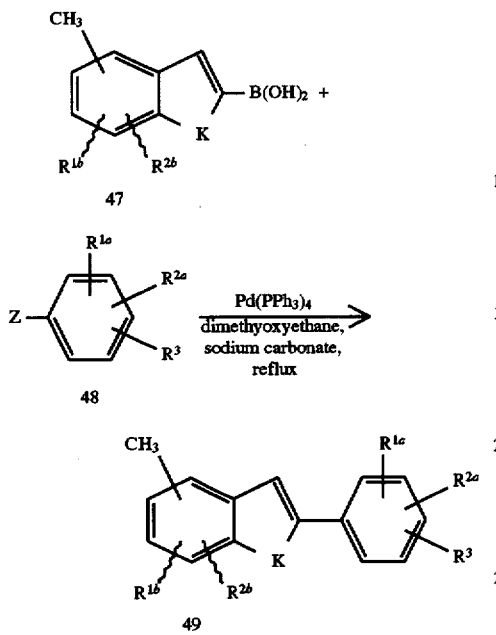

K is O, S or N—BOC
Z is bromine or iodine

SCHEME 16

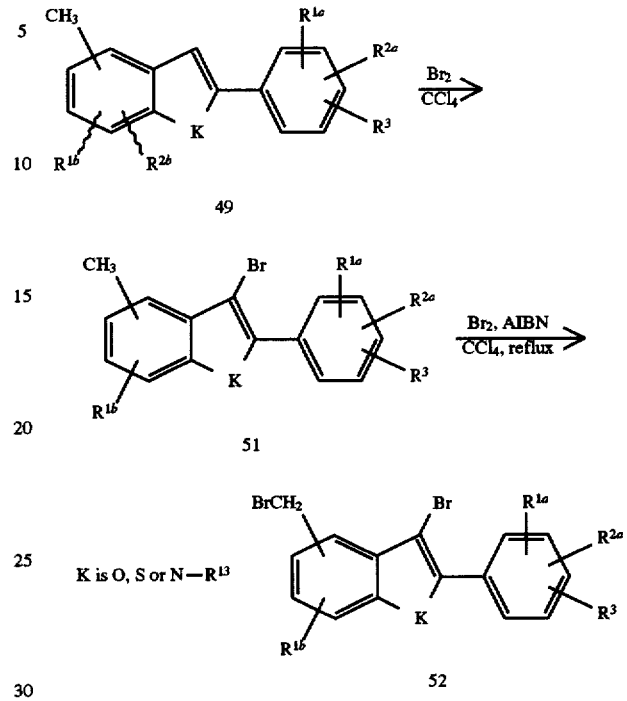

K is O, S or N—R¹³

2-Aryl substituted indole derivatives 49 can be elaborated to new intermediates 50 by the sequence shown in Scheme 15. Removal of the BOC protecting group with trifluoroacetic acid, followed by treatment with $R^{13}$—Y in the presence of a strong base, such as sodium hydride or potassium t-butoxide, gives the alkylated product 50.

3-Aryl substituted indole derivatives 56 are prepared from substituted hydrazine compounds 53 as illustrated in Scheme 17. Treatment with phenylacetaldehyde derivative 54 in a protic solvent, such as methanol or ethanol, gives hydrazone 55 which can be cyclized under acidic conditions at elevated temperature to give the desired 3-aryl indole 56.

SCHEME 15

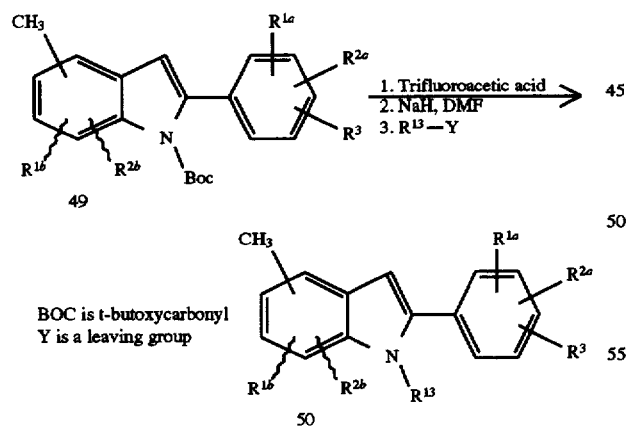

BOC is t-butoxycarbonyl
Y is a leaving group

SCHEME 17

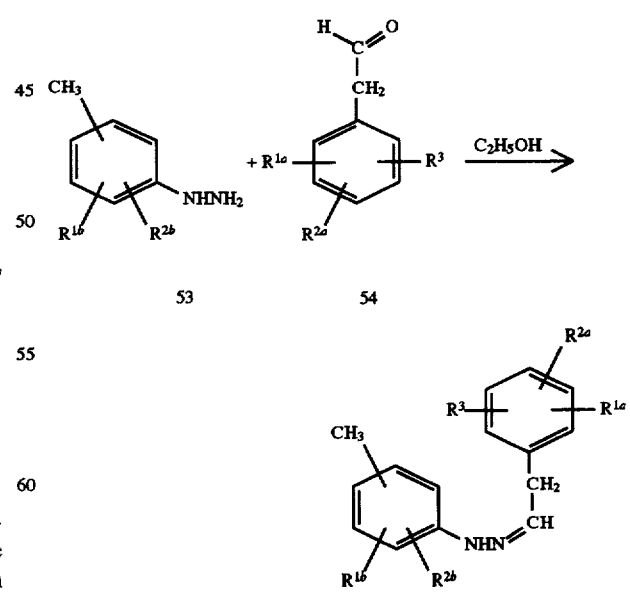

As illustrated in Scheme 16, 2-aryl benzothiophene, benzofuran and indole intermediates 49 may be converted to the 3-bromo derivatives 51 by reaction with bromine in carbon tetrachloride. Subsequent conversion to the alkylating agent 52 is carried out with N-bromosuccinimide as described above.

-continued
SCHEME 17

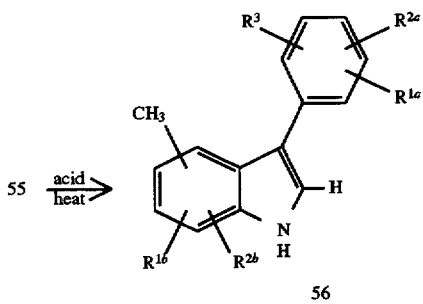

1-Aryl substituted analogs 59 are synthesized by the route shown in Scheme 18. Arylation of indole 57 by treatment with fluorobenzene derivative 58 in the presence of a strong base, such as sodium hydride, in a polar solvent, such as dimethylformamide, gives the desired N-aryl product 59.

SCHEME 18

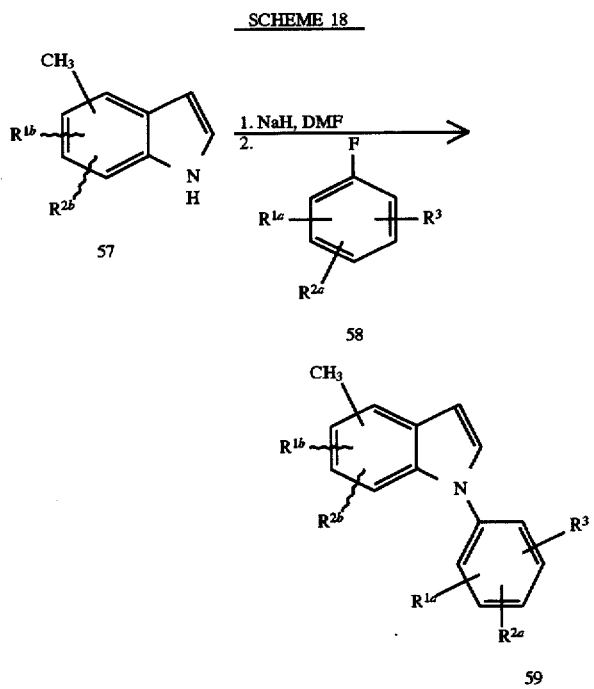

Compounds of formula VI wherein L is a 2-aryl substituted benzoxazole, benzthiazole or benzimidazole are prepared from the appropriately substituted aniline derivative 60 as indicated in Scheme 19. Condensation of 60 with the benzaldehyde compound 61 affords imine 62 which can be cyclized to the product 63 with barium manganate according to the procedure of R. Srivastava, et al. (Synth. Comm., 18, 1537–1544, 1986.). Conversion to the desired alkylating agent is carried out according to the procedure described in Scheme 13.

SCHEME 19

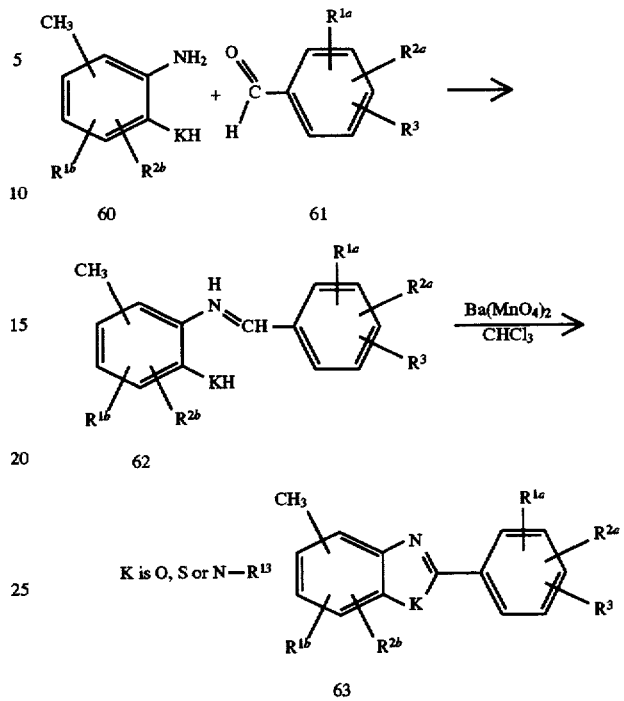

Benzimidazole compounds containing an N-aryl substituent 68 are prepared as shown in Scheme 20. Reaction of aniline derivative 65 with fluoronitrobenzene 64 gives the coupled product 66 which can be reduced to the diamine 67 by a variety of methods known to one skilled in the art, for example reaction with hydrogen in the presence of a metal catalyst, such as palladium on carbon. Reaction of 67 with $R^{2b}COOH$ under acidic conditions at elevated temperature, according to the procedure of J. Hendrickson (J. Org. Chem., 52, 4137–4139, 1987.), leads to the N–1 substituted compound 68. Bromination of 68 and alkylation with compounds of formula V is achieved by the methods described above.

SCHEME 20

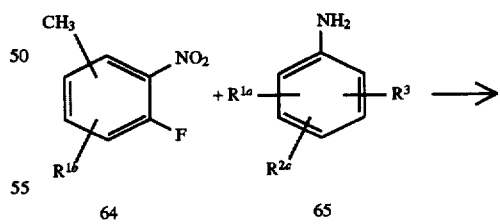

SCHEME 20 -continued

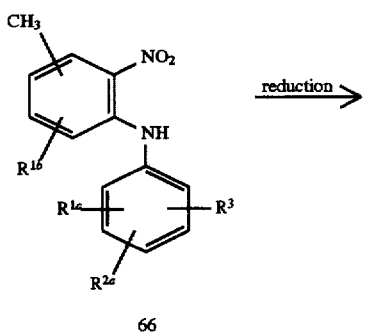

66

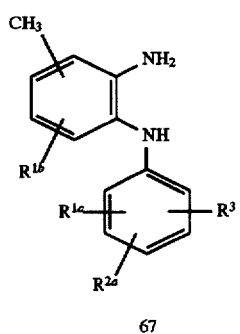

67

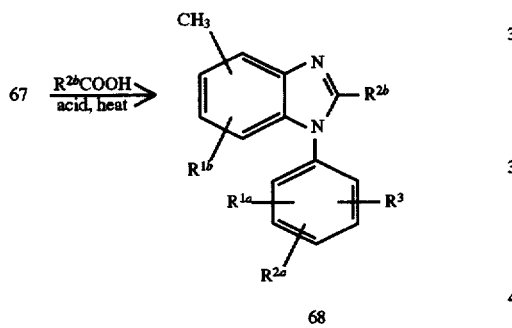

68

Compounds of formula VI wherein L is an N-aryl benzotriazole 69 are prepared from the intermediate 66 as described in Scheme 21. Diazotization according to the procedure of R. W. G. Preston, et al, (J. Chem. Soc., 1942, 500.), gives the cyclized benzotriazole product 69. Bromination of 69 and alkylation with compounds of formula V is achieved by the methods described above.

SCHEME 21

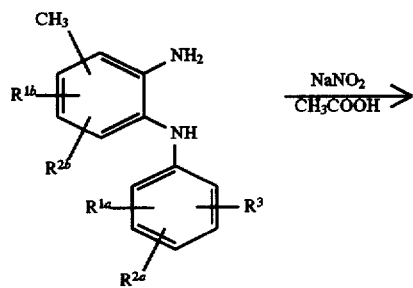

66

SCHEME 21 -continued

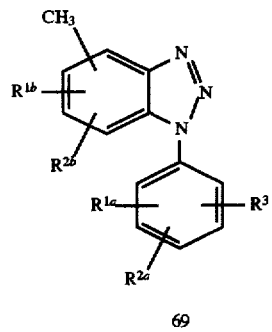

69

Aryl substituted imidazo[1,2-a]pyridine derivatives 72 can be prepared by treatment of an appropriately substituted 2-aminopyridine compound 70 with the phenacyl bromide 71 at elevated temperature under the conditions of C. Djerassi (J. Amer. Chem. Soc., 76, 4470, 1954) as shown in Scheme 22. Bromination of 72 and alkylation with compounds of formula V is achieved by the methods decribed above.

SCHEME 22

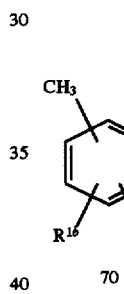

70

71

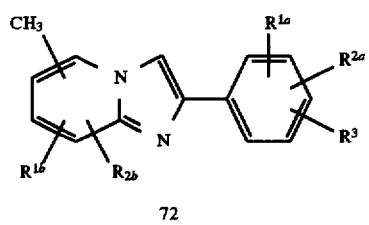

72

Compounds of formula I wherein $R^3$ is a tetrazole (75) are prepared as described in Scheme 23 by alkylation of V with a suitably substituted alkylating agent 73 containing a nitrile as tetrazole precursor. Elaboration to the desired tetrazole product 75 is carried out by treatment with trimethyltin azide in refluxing toluene.

SCHEME 23

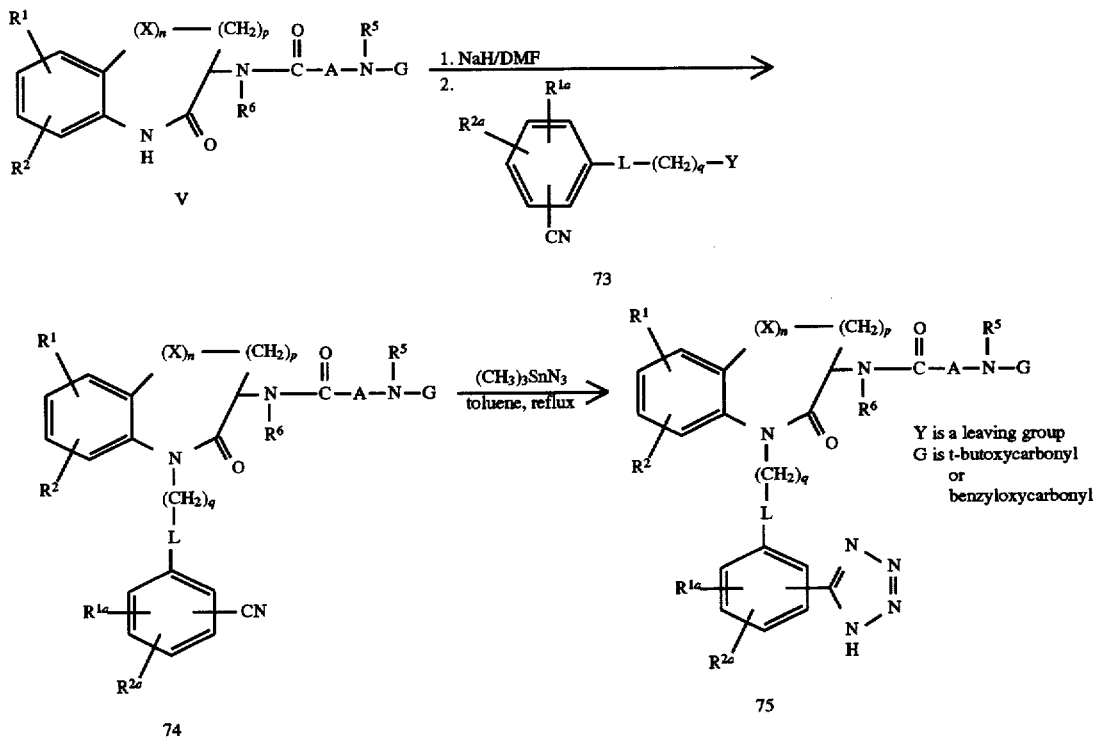

Y is a leaving group
G is t-butoxycarbonyl
or
benzyloxycarbonyl

A convenient synthesis of the useful intermediate 80 is presented in Scheme 24. Reaction of p-cresol with methylmagnesium chloride, followed by paraformaldehyde gives aldehyde 76. Treatment of 76 with α-bromo-o-toluonitrile under basic conditions gives the benzofuran product 77 in high yield. Conversion of the nitrile group to the tetrazole 78 is achieved by reaction with trimethyltin azide in boiling toluene. Bromination at C-3, followed by treatment with triphenylmethyl chloride gives the protected intermediate 79 which is converted to the desired alkylating agent 80 by the method described in Scheme 13.

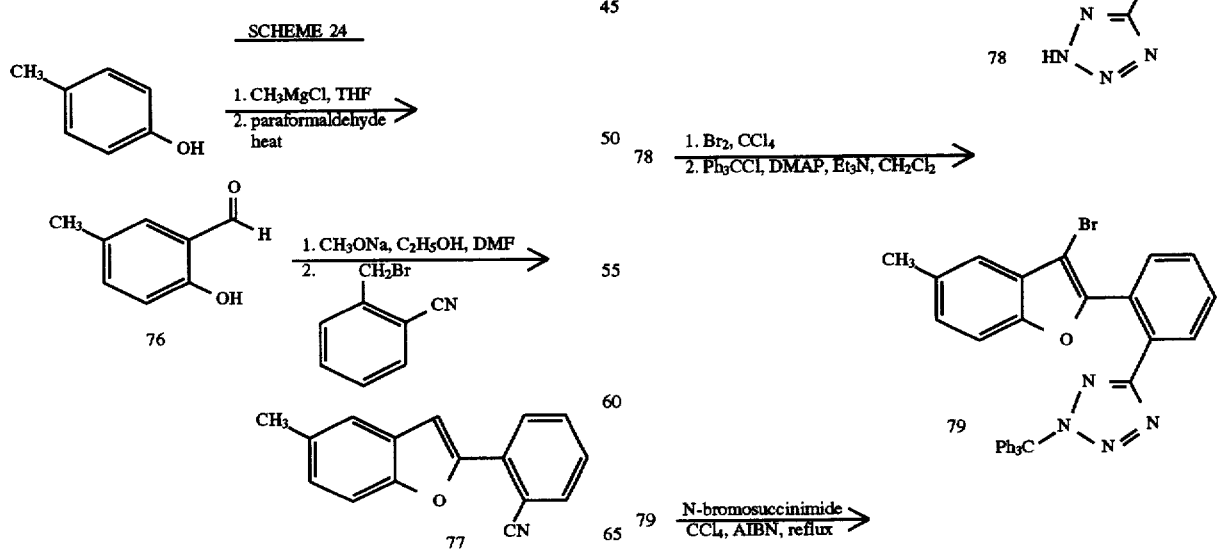

-continued
SCHEME 24

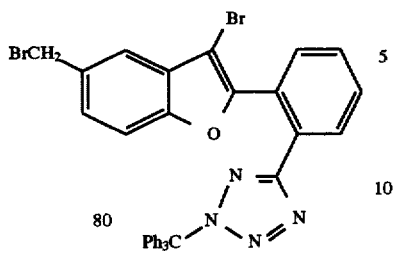

Compounds of Formula I wherein $R^3$ is taken as $R^4R^5NCO(CH_2)_v$ and v is 0 can be prepared by several methods. For example, as shown in Scheme 25, compound 81 wherein $R^4$ and $R^5$ are both hydrogen is conveniently prepared by hydrolysis of a nitrile precursor 74.

SCHEME 25

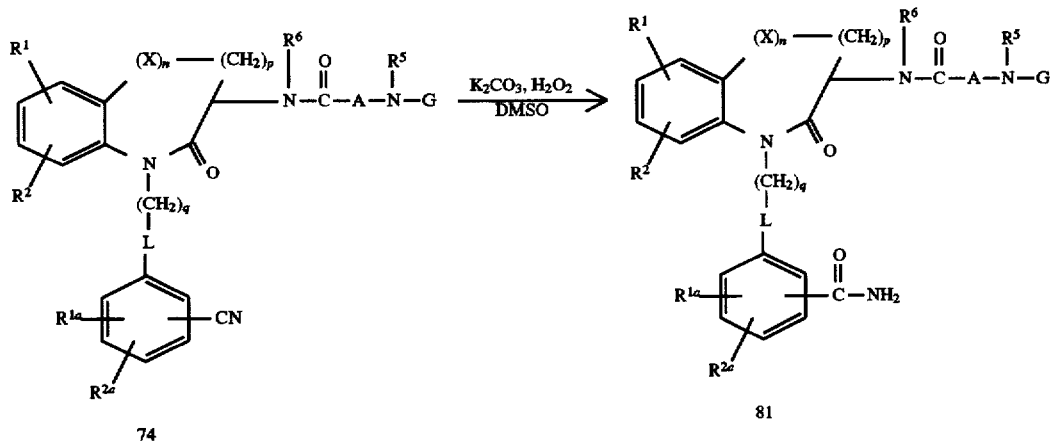

Thus, treatment of the nitrile 74 with hydrogen peroxide and a strong base, such as potassium carbonate, in a polar solvent, such as dimethylsulfoxide at temperatures of 25° C. to 150° C. results in formation of the amide derivative 81.

Compounds of Formula I wherein $R^3$ is taken as $R^4R^5NCO(CH_2)_v$ and v is 0 and $R^4$ and/or $R^5$ are not hydrogen (83) are prepared from the corresponding carboxylic acid derivatives 82 as shown in Scheme 26.

SCHEME 26

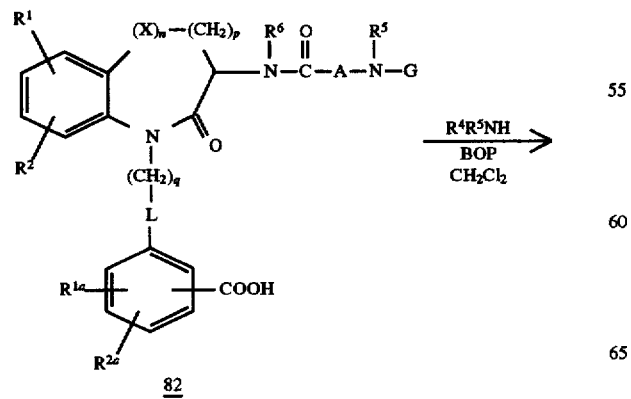

-continued
SCHEME 26

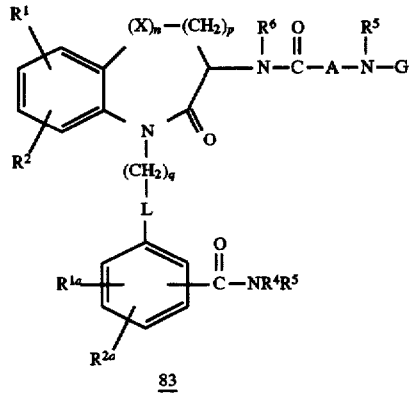

Coupling of the carboxylic acid derivative 82 with $R^4R^5NH$ is conveniently carried out by the use of a coupling reagent such as benzotriazol-1-yloxytris(dimethylamino) phosphonium hexafluorophosphate ("BOP") in an inert solvent such as methylene chloride.

Compounds of formula I where $R^3$ is a carbamate, semicarbazide or urea derivative, wherein this functionality is attached to the phenyl ring by a nitrogen atom are prepared from intermediates 85, obtained by alkylation with a derivative of formula VI wherein R³ is a nitro group 84 as shown in Scheme 27.

SCHEME 27

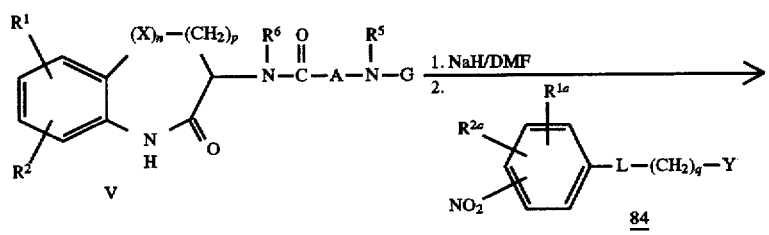

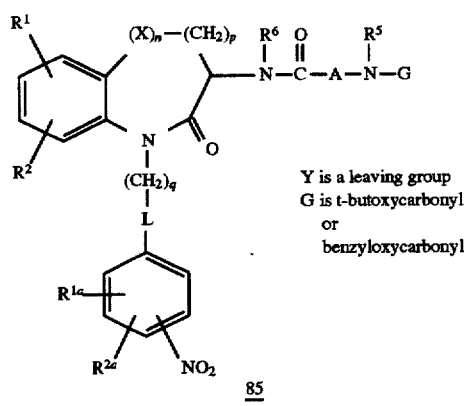

Y is a leaving group
G is t-butoxycarbonyl
or
benzyloxycarbonyl

As shown in Scheme 28, reduction of the nitro group of 85 is achieved by hydrogenation in the presence of a metal catalyst, such as palladium on carbon, in a protic solvent such as methanol or ethanol. It may be appreciated by one skilled in the art that for certain compounds where catalytic hydrogenation is incompatible with existing functionality, alternative methods of reduction are indicated, such as chemical reduction with stannous chloride under acidic conditions. It should also be noted that the protecting group G in intermediate 85 must be compatible with the experimental conditions anticipated for reduction. For example, intermediates 85 wherein G is t-butoxycarbonyl (BOC) are stable to the conditions of catalytic reduction employed in the conversion to 86. Intermediates 86 may also be further elaborated to new intermediates 87 by reductive alkylation with an aldehyde by the aforementioned procedures.

SCHEME 28

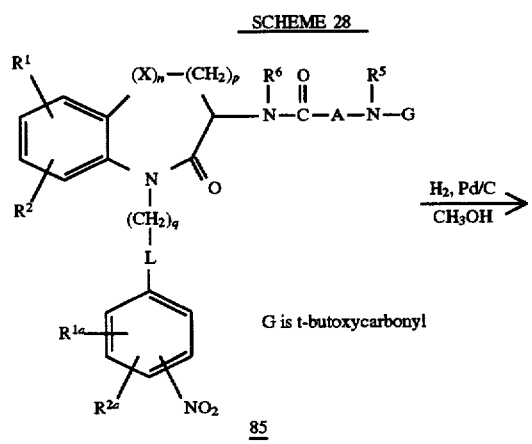

G is t-butoxycarbonyl

-continued
SCHEME 28

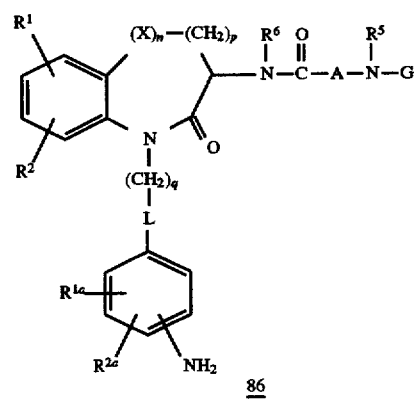

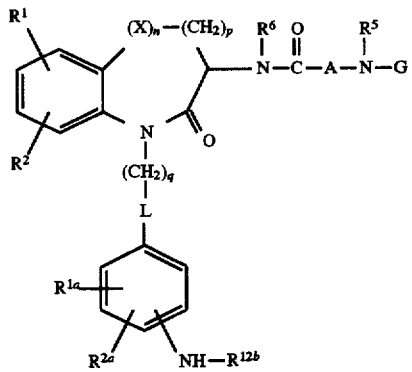

Elaboration of 87 to carbamate compounds 88 is achieved by reaction with the appropriate chloroformate reagent in pyridine or in methylene chloride with triethylamine as shown in Scheme 29.

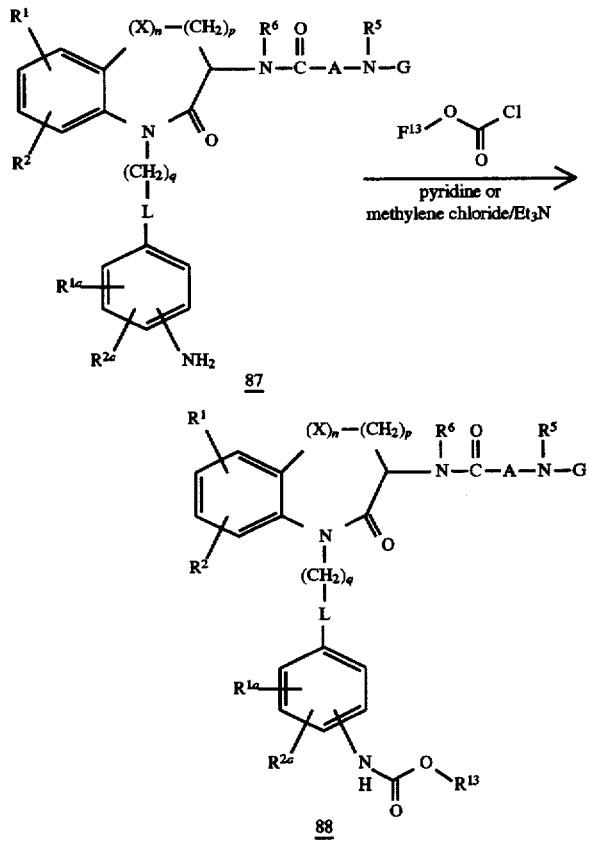

Transformation of amine intermediate 86 to urea derivatives is accomplished in several ways. Terminally disubstituted compounds 89 can be obtained directly by reaction of 86 with a disubstituted carbamoyl chloride in an inert solvent such as methylene chloride in the presence of triethylamine or 4-dimethylaminopyridine. In addition, monosubstituted compounds 90 wherein either $R^{4b}$ or $R^{12a}$ is hydrogen are obtained from 86 by reaction with an isocyanate as shown in Scheme 30.

Alternatively, amine 86 is converted to an isocyanate 91 by treatment with phosgene or an equivalent reagent such as bis(trichloromethyl)carbonate (triphosgene) as indicated in Scheme 31. Subsequent reaction of 91 with primary or secondary amines in an inert solvent such as methylene chloride gives the corresponding urea derivates 92 in good yield. Isocyanate 91 is also converted to substituted semicarbazides 93 or hydroxy- or alkoxyureas 94 by reaction with substituted hydrazines or hydroxy- or alkoxylamines, respectively.

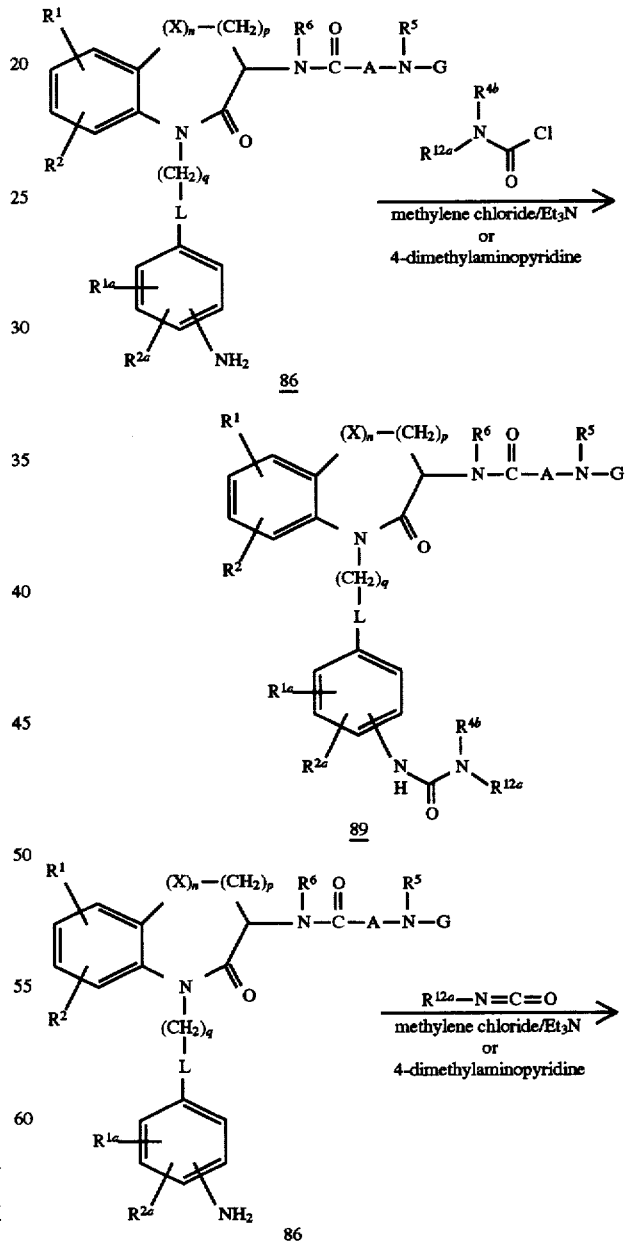

-continued
SCHEME 30
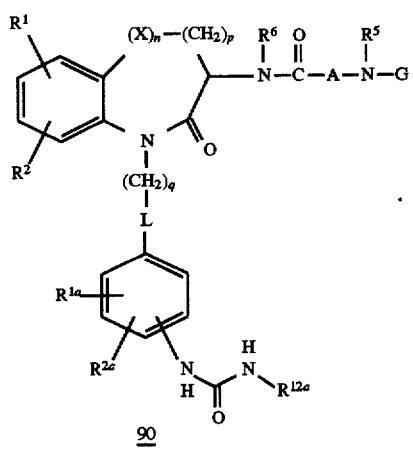
90
SCHEME 31
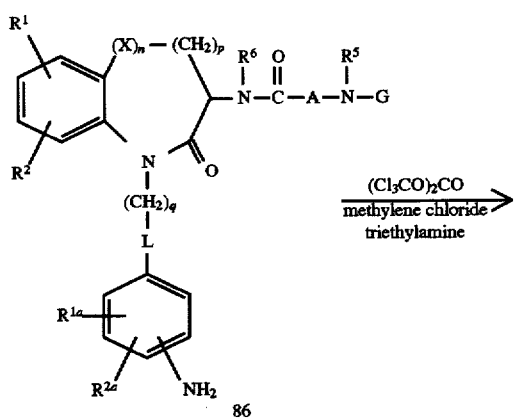
86
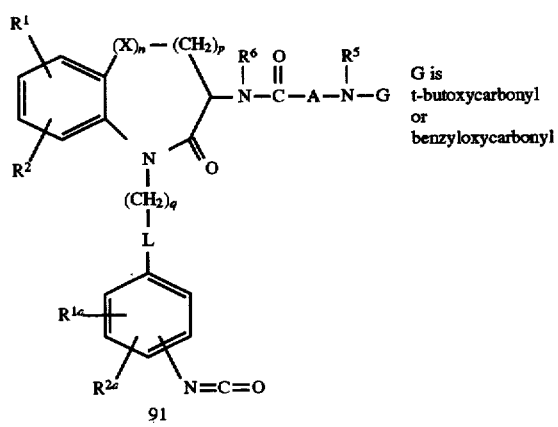
91
-continued
SCHEME 31
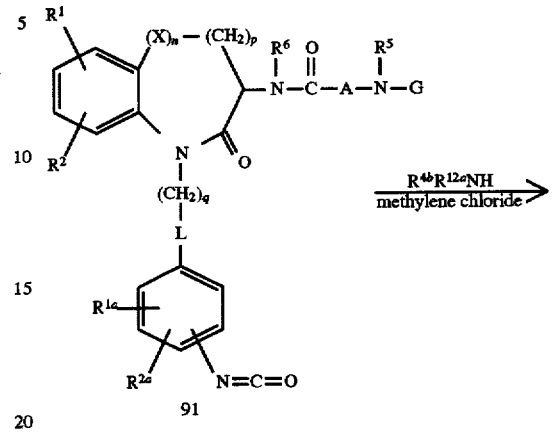
91
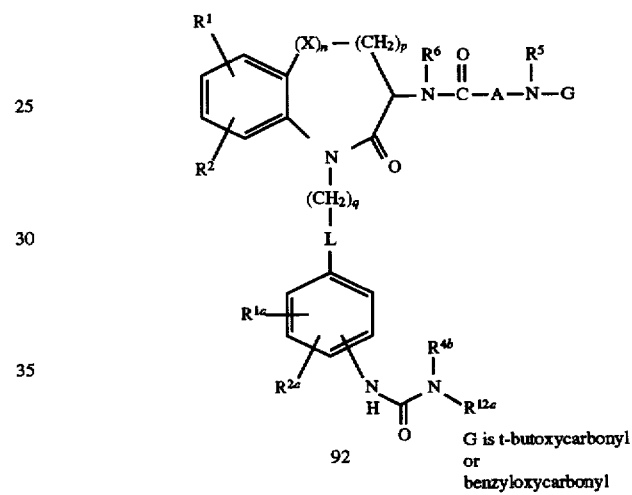
92  G is t-butoxycarbonyl or benzyloxycarbonyl
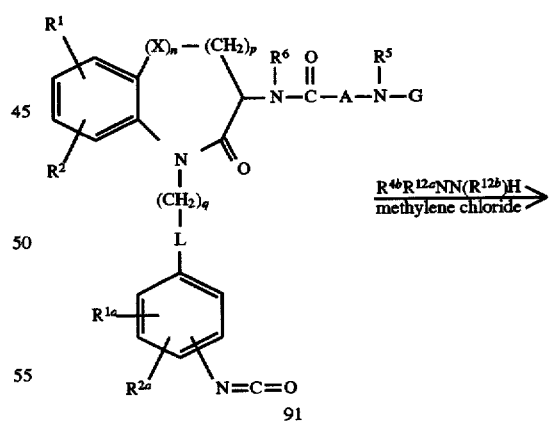
91

43
-continued
SCHEME 31

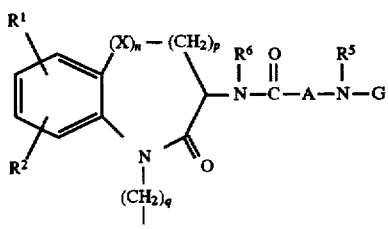

93  G is t-butoxycarbonyl or benzyloxycarbonyl

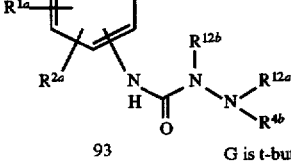

91

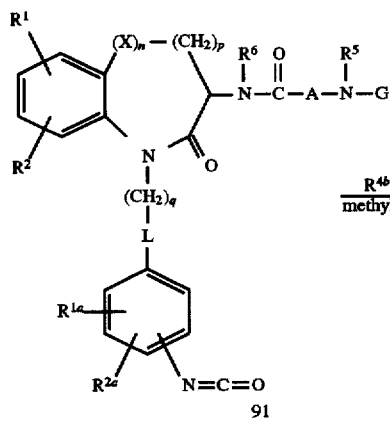

94  G is t-butoxycarbonyl or benzyloxycarbonyl

Compounds of formula I where $R^3$ is a carbazate or carbamate derivative where attachment to the phenyl ring is through the oxygen atom of the carbazate or carbamate linkage are prepared from the acetophenone intermediate 95 as indicated in Scheme 32.

44

Oxidative rearrangement of 95 through the use of a peroxy-carboxylic acid (Baeyer-Villager reaction) such as m-chloroperbenzoic acid gives the ester 96 which is hydrolyzed in the presence of a strong base such as sodium or lithium hydroxide to give phenol 97.

Reaction of 97 with an isocyanate leads directly to carbamate analogs 98. Additionally, treatment of 97 with N,N'-carbonyldiimidazole in dimethylformamide can form an activated intermediate which will react with substituted hydrazine reagents to give carbazate products 99.

SCHEME 32

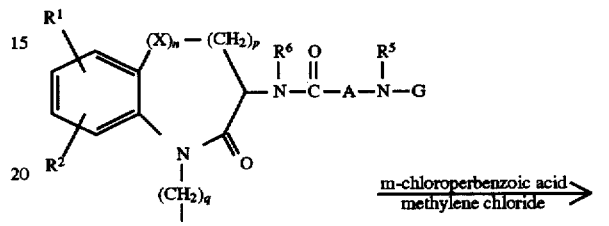

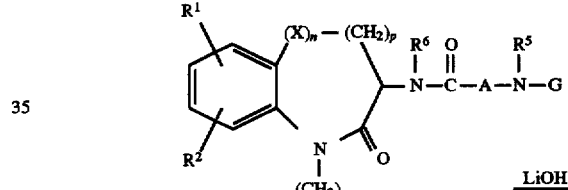

95

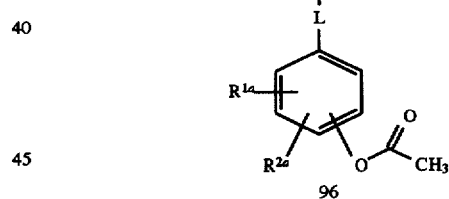

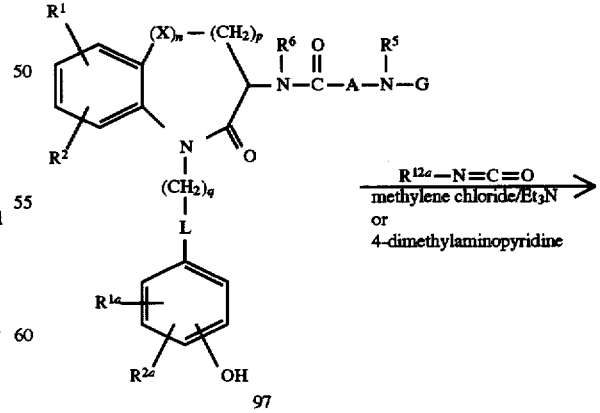

97

SCHEME 32 -continued

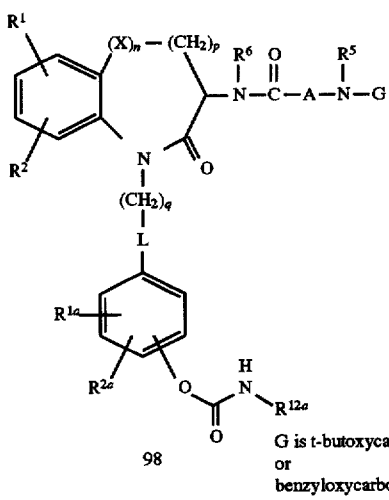

98  G is t-butoxycarbonyl or benzyloxycarbonyl

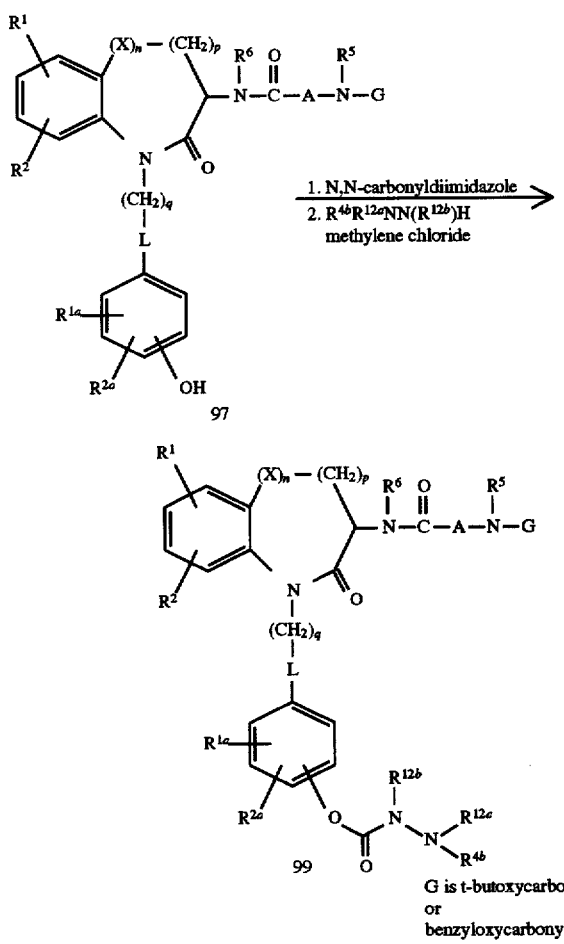

97

1. N,N-carbonyldiimidazole
2. R⁴ᵇR¹²ᵃNN(R¹²ᵇ)H
   methylene chloride

99  G is t-butoxycarbonyl or benzyloxycarbonyl

Compounds of formula I wherein $R^3$ contains the linkage —$CH_2N(R^{12b})$— can be prepared from the t-butyl ester intermediate 100 as described in Scheme 33. Removal of the t-butyl ester through the use of trifluoroacetic acid gives the carboxylic acid 101. It may be appreciated by one skilled in the art that the protecting group G in 100 must therefore be compatible with the strongly acidic conditions employed for ester cleavage, hence G is taken as benzyloxycarbonyl. Conversion of the carboxylic acid to the benzylamine derivative 102 can be achieved by a five-step sequence consisting of: 1) formation of a mixed anhydride with isobutyl chloroformate; 2) reduction with sodium borohydride to the benzyl alcohol; 3) formation of the mesylate with methanesulfonyl chloride; 4) formation of the azide by reaction with sodium azide, and finally, 5) reduction of the azide with tin(II) chloride. The benzylamine intermediate 102 can be further elaborated to 103 by the aforementioned reductive amination procedure.

SCHEME 33

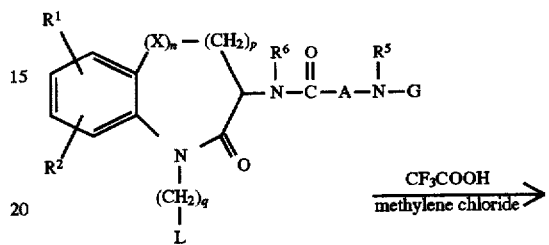

100

$\xrightarrow[\text{methylene chloride}]{CF_3COOH}$

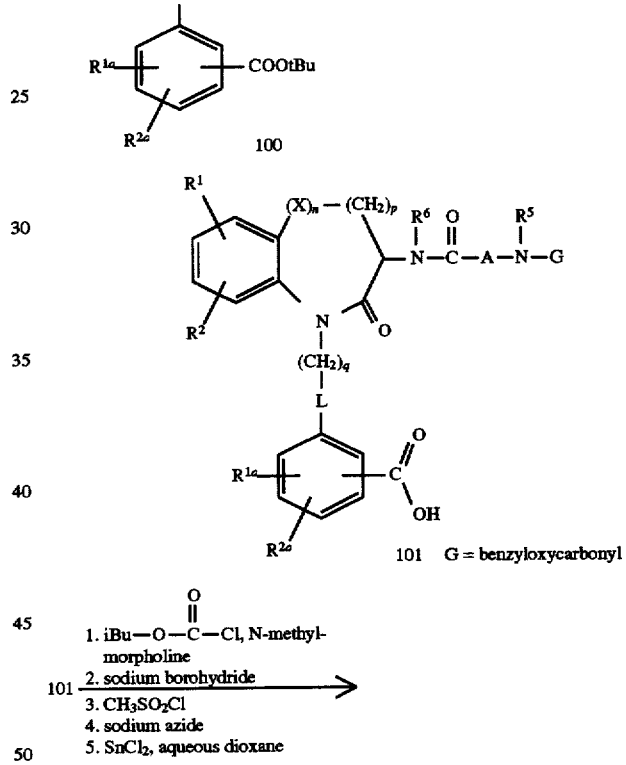

101  G = benzyloxycarbonyl $$\begin{array}{c}O\\\|\end{array}$$

1. iBu—O—C—Cl, N-methyl-morpholine
2. sodium borohydride
3. CH₃SO₂Cl
4. sodium azide
5. SnCl₂, aqueous dioxane

101 →

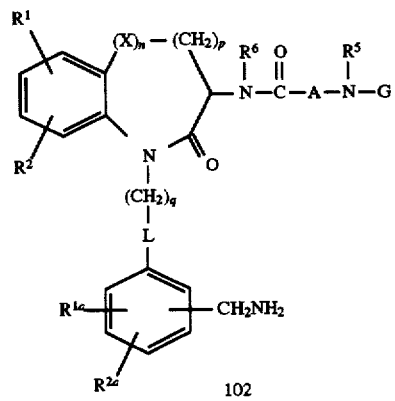

102

47
-continued
SCHEME 33
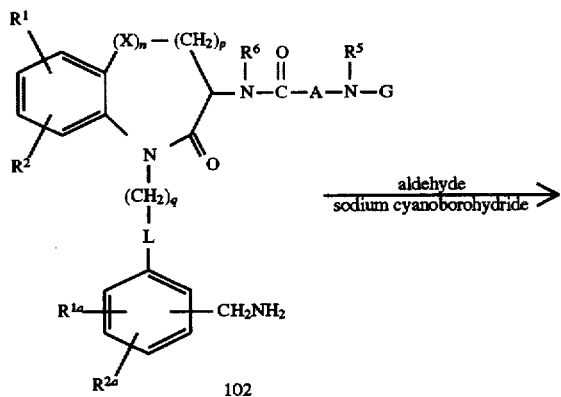
102
48
-continued
SCHEME 33
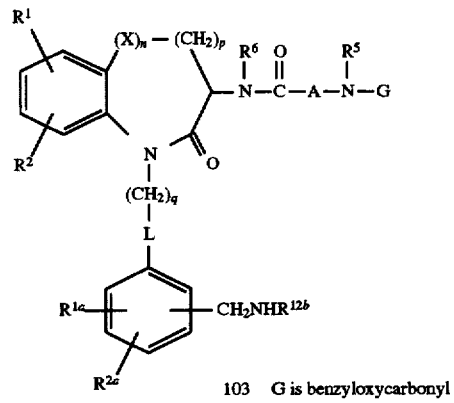
103  G is benzyloxycarbonyl
Reaction of amine 103 with the appropriate reagents to form urea-linked compounds 104 and 105 carbamate-linked compounds 106, and amide-linked structures 107 are illustrated in Scheme 34.
SCHEME 34
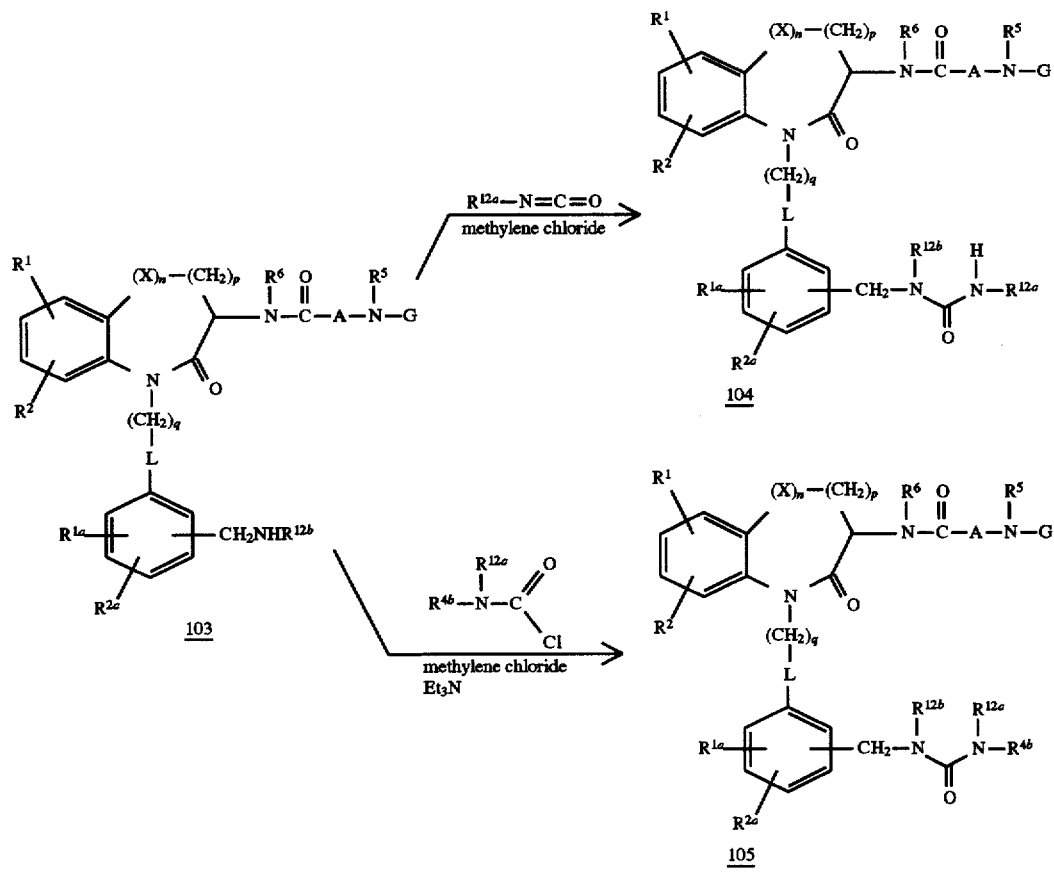

-continued
SCHEME 34

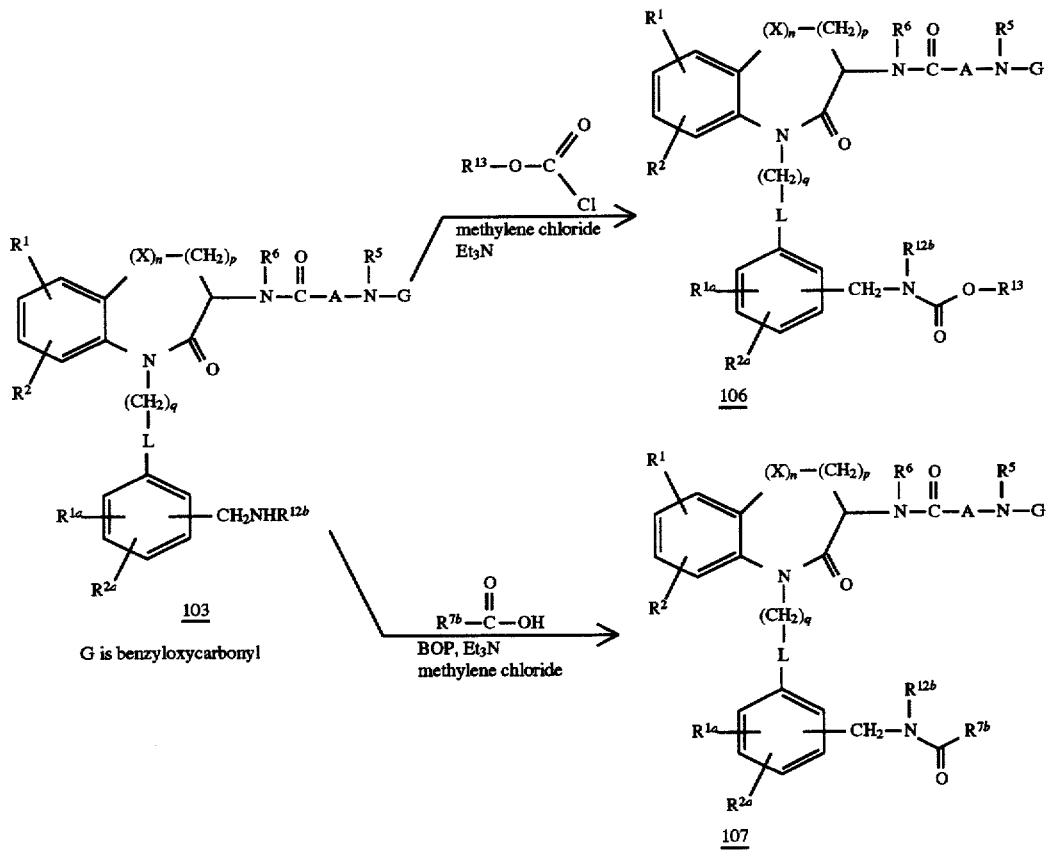

Conversion to the final products of formula I wherein $R^4$ is hydrogen, is carried out by simultaneous or sequential removal of all protecting groups from intermediate VII as illustrated in Scheme 35. Removal of benzyloxycarbonyl groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Catalytic hydrogenation is also employed in the removal of N-triphenylmethyl (trityl) protecting groups. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis*.

SCHEME 35

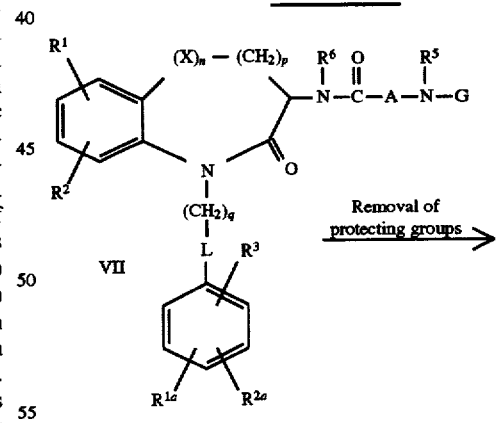

-continued
SCHEME 35

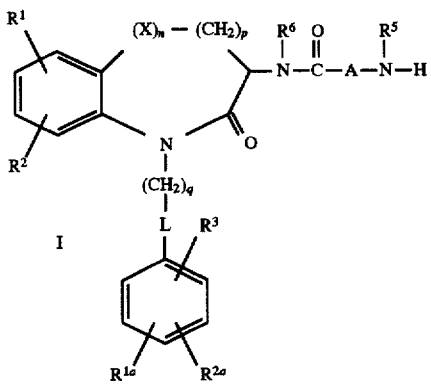

Compounds of formula I wherein $R^4$ and $R^5$ are each hydrogen can be further elaborated by reductive alkylation with an aldehyde by the aforementioned procedures or by alkylations such as by reaction with various epoxides as shown in Scheme 36. The products, obtained as hydrochloride or trifluoroacetate salts, are conveniently purified by reverse phase high performance liquid chromatography (HPLC) or by recrystallization.

SCHEME 36

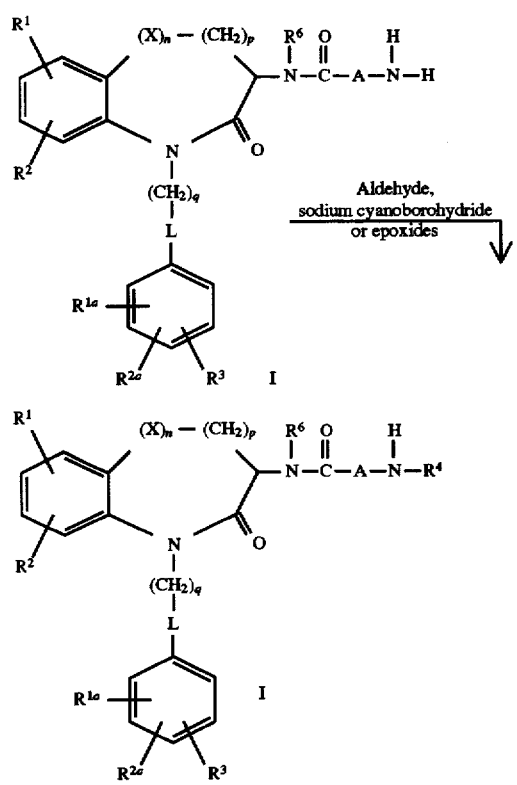

Removal of benzyloxycarbonyl groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis* T. W. Greene, John Wiley and Sons, New York, 1981.

Compounds of formula I wherein $R^4$ and $R^5$ are each hydrogen can be further elaborated by reductive alkylation with an aldehyde by the aforementioned procedures or by alkylations such as by reaction with various epoxides. The products, obtained as hydrochloride or trifluoroacetate salts, are conveniently purified by reverse phase high performance liquid chromatogrphy (HPLC) or by recrystallization.

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed novel benzo-fused lactam growth hormone secretagogues is in combination with other growth hormone secretagogues such as GHRP-6, GHRP-1 as described in U.S. Pat. No. 4,411,890; and publications WO 89/07110 and WO 89/07111 and B-HT920 or growth hormone releasing factor and its analogs or growth hormone and its analogs or somatomedins including IGF-1 and IGF-2. A still further use of the disclosed novel benzo-fused lactam growth hormone secretagogues is in combination with $\alpha_2$ adrenergic agonists or $\beta_3$ adrenergic agonists in the treatment of obesity or in combination with parathyroid hormone or bisphosphonates, such as MK-217 (alendronate), in the treatment of osteoporosis.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; Prevention of catabolic side effects of glucocorticoids, treatment of osteoporosis, stimulation of the immune system, treatment of retardation, acceleration of wound healing, accelerating bone fracture repair, treatment of growth retardation, treating renal failure or insufficiency resulting in growth retardation, treatment of physiological short stature, including growth hormone deficient children, treating short stature associated with chronic illness, treatment of obesity and growth retardation associated with obesity, treating growth retardation associated with Prader-Willi syndrome and Turner's syndrome; Accelerating the recovery and reducing hospitalization of burn patients; Treatment of intrauterine growth retardation, skeletal dysplasia, hypercortisolism and Cushings syndrome; Induction of pulsatile growth hormone release; Replacement of growth hormone in stressed patients; Treatment of osteochondrodysplasias, Noonans syndrome, schizophrenia, depression, Alzheimer's disease, delayed wound healing, and psychosocial deprivation; treatment of pulmonary dysfunction and ventilator dependency; Attenuation of protein catabolic response after a major operation; reducing cachexia and protein loss due to chronic illness such as cancer or AIDS. Treatment of hyperinsulinemia including nesidioblastosis; Adjuvant treatment for ovulation induction; To stimulate thymic development and prevent the age-related decline of thymic function; Treatment of immunosuppressed patients; Improvement in muscle strength, mobility, maintenance of skin thickness, metabolic homeostasis, renal hemeostasis in the frail elderly; Stimulation of osteoblasts, bone remodelling, and cartilage growth; Stimulation of the immune system in companion animals and treatment of disorders of aging in companion animals; Growth promotant in livestock; and stimulation of wool growth in sheep.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg. of body weight daily are administered to patients and animals, e.g., mammals, to obtain effective release of growth hormone.

The following examples are provided for the purpose of further illustration only and are not intended to be limitations on the disclosed invention.

EXAMPLE 1

3-Amino-N-[1-[[3-bromo-2-[2-(1H-tetrazol-5-yl) phenyl]-5-benzofuranyl]methyl]-2,3,4,5-tetrahydro-2-oxo-1H-1-benzazepin-3(R)-yl]-3-methylbutanamide, trifluoroacetate Step A: 1-Tetralone oxime To 4.6 L of water at room temperature in a 4-neck 50 L flask sitting in a steam bath apparatus equipped with an overhead stirrer, a temperature probe and reflux condenser was added 3.72 Kg (27.36 mol) of sodium acetate with stirring, followed by 1.9 Kg of hydroxylamine hydrochloride (27.36 mol). To this slurry at room temperature, 12 L of ethanol was added followed by 1.994 Kg (13.68 mol) of 1-tetralone. Additional ethanol (1.7 L) was used to rinse off the funnel and added to the reaction mixture. The resulting light orange slurry was heated to 75° C. over 40 minutes and maintained at 75°–85° C. for another 75 minutes. The reaction mixture was cooled with the aid of ice packed around the flask. When the internal temperature reached 32° C., the reaction mixture was pumped over 15 minutes into 60 L of ice contained in a 200 L vessel. The reaction vessel was washed with an additional 2 L of water which was added to the 200 L vessel. When the ice melted, the mixture was filtered through a filter pad and the wet cake washed with 4 L of water. The wet cake was suction dried for 1 hour then transferred to two trays and dried under vacuum at 40° C. for 2 days to give 2.094 Kg (13.01 mol, 95%) of product. $^1$H NMR (250 MHz,CDCl$_3$): 1.90 (m,2H), 2.80 (t,6 Hz,2H), 2.88 (t,6 Hz,2H), 7.15–7.35 (m,3H), 7.90 (d,8 Hz,1H), 8.9 (br s,1H).

Step B: 2,3,4,5-Tetrahydro-1H-1-benzazepin-2-one

To 10 L of methanesulfonic acid in a 22 L 3-neck flask equipped with an overhead stirrer, a temperature probe, nitrogen inlet and reflux condenser was added 2.6 Kg (18.61 mol) of phosphorus pentoxide. An additional 1.6 L of methanesulfonic acid was used to wash all the phosphorus pentoxide into the vessel. The mixture was heated at 90° C. for 2.5 hours then cooled to 50° C. using an ice bath and treated with 2.00 Kg (12.41 mol) of 1-tetralone oxime in several portions over 15 minutes. The mixture was heated at 63° C. for 10 minutes then slowly heated to 80° C. and kept at 80° C. for 3 hours. The reaction mixture was pumped into 70 L of ice then treated slowly with 11.25 L of 50% aqueous sodium hydroxide over 90 minutes at such a rate so as to maintain the temperature below 28° C. The mixture was filtered and 4 L of the filtrate was used to rinse the vessel. The wet cake (pink) was washed with 8 L of water then suction dried for 45 minutes then transferred to two trays and dried under vacuum at 40° C. for 2 days to give 1.9 Kg (11.79 mol, 95%) of product. $^1$H NMR (250 MHz,CDCl$_3$): 2.24 (m,2H), 2.38 (t,6 Hz,2H), 2.82 (t,6 Hz,2H), 7.03 (d,8 Hz,1H), 7.13 (m,1H), 7.24 (m,2H), 8.63 (br s,1H).

Step C: 3-Iodo-2,3,4,5-tetrahydro-1H-1-benzazepin-2-one

A suspension of 1.8 Kg (11.17 mol) of 2,3,4,5-tetrahydro-1H-1-benzazepin-2-one in a mixture of 22.33 L of methylene chloride and 11.78 L (55.83 mol) of hexamethyldisilazane was heated at reflux for 10 minutes then cooled to 30° C. and treated with 8.503 Kg (33.5 mol) of iodine in one portion. The mixture was heated at reflux for 2.5 hours then cooled to room temperature. Aqueous sodium sulfite containing 4.926 Kg of sodium sulfite in 44 L of water was cooled to 0° C. and into it was poured the reaction mixture in several portions with vigorous stirring while maintaining the temperature below 10° C. The reaction vessel was rinsed with 22.33 L of methylene chloride and the washing transferred to the quenching mixture. The quenching mixture was stirred vigorously and the layers allowed to separate. The aqueous layer was removed and reextracted with 22.33 L of methylene chloride. The combined organic layers were washed with 11 L of water and concentrated under vacuum to a final volume of approximately 5 L. The residue was treated with 55 L of toluene and concentrated under vacuum to a final volume of 10 L. The resulting slurry was removed by filtration and the filter cake washed with an additional 5 L of toluene and dried under vacuum at ambient temperature for 24 hours to give 1.842 Kg (6.42 mol, 57%) of product. $^1$H NMR (200 MHz,CDCl$_3$): 2.6–2.8 (m,3H), 2.93 (m,1H), 4.64 (t,8 Hz,1H), 6.97 (d,8 Hz,1H), 7.10–7.35 (m,3H), 7.55 (br s,1H).

Step D: 3(R)-Amino-2,3,4,5-tetrahydro-1H-1-benzazepin-2-one, D-tartaric acid salt 3-Iodo-2,3,4,5-tetrahydro-1H-1-benzazepin-2-one (1.79 Kg, 6.24 mol) was slurried in 6.2 L of methanol and the slurry charged into an autoclave. Condensed ammonia (1.55 L) was added and the autoclave closed, with stirring, and heated to 100° C. over 1 hour. Heating at 100° C. was continued for 2 hours then the autoclave was allowed to cool to room temperature over 1 hour, during which time the internal pressure was 150–155 psi. The reaction mixture was transferred to a polyethylene jug and the autoclave rinsed with 2×8 L of methanol. The washings were concentrated under vacuum at 30° C. then combined with the reaction mixture and concentrated to near dryness under vacuum at 30° C. The resulting residue was dissolved in 4 L of ethyl acetate then concentrated to dryness under vacuum at 30° C.

Sodium chloride (712 g) was dissolved in 2 L of water and 1.0 Kg of sodium carbonate was dissolved in 6 L of water. Two liters of the sodium carbonate solution was added to the concentrated residue and the resulting slurry transferred to an extraction flask. Another 2 L portion of the sodium carbonate solution was added to the residue flask and the solution transferred to the extraction flask. The remaining sodium carbonate solution was used in the same way. The sodium chloride solution was added to the sodium carbonate/aminolactam emulsion and the resulting mixture stirred for 10 minutes then extracted with four 6 L portions of methylene chloride. The combined methylene chloride layers were concentrated to dryness; the residue was treated with 2 L of 200 proof ethanol and the resulting slurry concentrated to dryness under vacuum to give 1.171 Kg of crude product.

The crude product was slurried in 8 L of ethanol and treated with 900 g of D-tartaric acid in one portion. Water (7 L) was added and the mixture heated to 77° C., then additional ethanol (45 L) was added and heating continued. The solution was cooled to 43° C. and treated with the seed slurry. (The seed slurry was prepared by the route described above starting with 10.50 g of crude product and 9.1 g of D-tartaric acid.) The solution was aged at room temperature for 48 hours. The slurry formed was removed by filtration and the wet cake washed with 1.8 L of ethanol. The resulting filter cake was suction dried with nitrogen bleeding for 20 hours then transferred into a drying tray and dried under vacuum for 24 hours to give 354 g (1.085 mol, 17.4%) of the product. $^1$H NMR (250 MHz,CDCl$_3$): 2.13 (m,1H), 2.51 (m,2H), 2.73 (m,2H), 3.68 (t,6 Hz,1H), 3.98 (s,2H), 7.05 (d,8 Hz,1H), 7.16 (t,8 Hz,1H), 7.30 (m,2H), 7.6 (br s,5H), 10.26 (br s,1H).

Step E: 3(R)-Amino-2,3,4,5-tetrahydro-1H-1-benzazepin-2-one

A solution of 229.23 g (0.700 mol) of 3(R)-amino-2,3,4,5-tetrahydro-1H-1-benzazepin-2-one, D-tartrate in 4.1 L of water was treated with 194 g (1.40 mol) of potassium carbonate. Subsequent portions of 100 g and 135 g of potassium carbonate were added until the pH was 10.5. The mixture was extracted with four 4 L portions of methylene chloride which were then combined and dried over magnesium sulfate. The aqueous layer was treated with 1.4 Kg of sodium chloride and reextracted with four 4 L portions of methylene chloride which were then combined and dried over magnesium sulfate. The two 16 L batches of extracts were combined, filtered and concentrated to dryness under vacuum to give 115.5 g of product which contained 1.6% of an impurity identified as 7-iodo-3(R)-amino-2,3,4,5-tetrahydro-1H-1-benzazepin-2-one.

A solution of 107.02 g (0.607 mol) of the intermediate obtained above in 1.712 L of ethanol was hydrogenated at room temperature and 40 psi over 4.00 g of 10% palladium on carbon for 4 hours. The catalyst was removed by filtration through solkaflok and the filtrate concentrated to dryness under vacuum to give 101.08 g (0.574 mol, 94.4%) of product.

Step F: 4,4-Dimethylazetidin-2-one

A 3-neck 3 L round bottom flask equipped with a magnetic stirrer, thermometer, cold finger condenser and nitrogen bubbler was charged with 1 L of ether. The flask was cooled to −65° C. and into it was condensed 500–600mL of isobutylene. The cold finger condenser was replaced with a dropping funnel and 200mL (325 g, 2.30 mol) of chlorosulfonyl isocyanate was added dropwise over 1.5 hours. The mixture was maintained at −65° C. for 1.5 hours then the dry ice/acetone cooling bath replaced with methanol/ice and the internal temperature slowly increased to −5° C. at which time the reaction initiated and the internal temperature rose to 15° C. with evolution of gas. The internal temperature remained at 15° C. for several minutes then dropped back down to −5° C. and the mixture stirred at −5° C. for 1 hour. The methanol/ice bath was removed and the reaction mixture warmed to room temperature and stirred overnight.

The reaction mixture was transferred to a 3-neck 12 L round bottom flask fitted with a mechanical stirrer and diluted with 2 L of ether. The well stirred reaction mixture was treated with 2 L of saturated aqueous sodium sulfite. After 1 hour, an additional 1 L of saturated aqueous sodium sulfite was added followed by sufficient sodium bicarbonate to adjust the pH to approximately 7. The mixture was stirred another 30 minutes then the layers allowed to separate. The ether layer was removed and the aqueous layer reextracted with 2×1 L of ether. The combined ether extracts were washed once with 500 mL of saturated aqueous sodium bicarbonate and once with 500 mL of saturated aqueous sodium chloride. The ether layer was removed, dried over magnesium sulfate, filtered and concentrated under vacuum to give 33 g of a pale yellow oil. The aqueous layer was made basic by the addition of solid sodium bicarbonate and extracted with 3×1 L of ether. The combined ether extracts were washed and dried as described above, then combined with the original 33 g of pale yellow oil and concentrated under vacuum to give 67.7 g of product. Further extraction of the aqueous layer with 4×1 L of methylene chloride and washing and drying as before gave an additional 74.1 g of product. Still further extraction of the aqueous layer with 4×1 L of methylene chloride gave an additional 21.9 g of product. The combined product (163.7 g, 1.65 mol, 72%) was used in Step G without purification. $^1$H NMR (200 MHz,CDCl$_3$): 1.45 (s,6H), 2.75 (d,3 Hz,2H), 5.9 (br s,1H).

Step G: N-(t-Butoxycarbonyl)-4,4-dimethylazetidin-2-one

A 5 L, 3-neck round bottom flask equipped with a magnetic stirrer, thermometer, nitrogen bubbler and addition funnel was charged with 88.2 g (0.89 mol) of 4,4-dimethylazetidin-2-one (Step F), 800 mL of methylene chloride, 150 mL of triethylamine (1.08 mol) and 10.9 g (0.089 mol) of 4-dimethylaminopyridine. To the stirred solution at room temperature was added dropwise over 15 minutes a solution of 235 g (1.077 mol) of di-t-butyldicarbonate in 300 mL of methylene chloride. The reaction mixture was stirred at room temperature overnight then diluted with 1 L of methylene chloride and washed with 500 mL of saturated aqueous ammonium chloride, 500 mL of water, and 500 mL of saturated aqueous sodium chloride. The organic layer was separated, dried over magnesium sulfate, filtered and concentrated under vacuum to afford 180.3 g of crude product as an orange solid. The material was used directly in Step H without purification. $^1$H NMR (200 MHz,CDCl$_3$): 1.50 (s,9H), 1.54 (s,6H), 2.77 (s,2H).

Step H: 3-t-Butoxycarbonylamino-3-methylbutanoic acid

A 3 L, 3-neck round bottom flask equipped with a magnetic stirrer, thermometer, nitrogen bubbler and addition funnel was charged with 180.3 g (0.89 mol) of N-(t-butoxycarbonyl)-4,4-dimethylazetidin-2-one dissolved in 1 L of tetrahydrofuran. The solution was cooled to 0°–5° C. and treated dropwise with 890 mL of 1.0M aqueous lithium hydroxide over 30 minutes. The reaction mixture was stirred at 0°–5° C. for 2 hours then diluted with 1 L of ether and 1 L of water. The layers were allowed to separate and the aqueous layer reextracted with an additional 1 L of ether. The aqueous layer was acidified by the addition of 1 L of saturated aqueous sodium bisulfate, then extracted with 1×1 L and 2×500 mL of ether. The combined organic layer and ether extracts were washed with 500 mL of saturated aqueous sodium chloride, dried over magnesium sulfate and concentrated under vacuum to 173 g of a yellow oil that solidified upon standing. The material was slurried with warm hexane then filtered and dried under high vacuum to afford 168.5 g (0.775 mol, 87%) of product as a white solid. $^1$H NMR (200 MHz,CDCl$_3$): 1.39 (s,6H), 1.44 (s,9H), 2.72 (s,2H). FAB-MS: calculated for $C_{10}H_{19}NO_4$ 217; found 218 (M+H,54%).

Step I: 3-t-Butoxycarbonylamino-3-methyl-N-[2,3,4,5-tetrahydro-2-oxo-1H-1-benzazepin-3(R)-yl]-butanamide A solution of 8.70 g (49.4 mmol) of 3(R)-amino-2,3,4,5-tetrahydro-1H-1-benzazepin-2-one (Step E) in 100 mL of methylene chloride was treated with 10.73 g (49.4 mmol) of 3-t-butoxycarbonylamino-3-methylbutanoic acid (Step H) and 13.8 mL of triethylamine (10.0 g, 99 mmol, 2 eq.). The reaction flask was immersed in an ambient temperature water bath then 26 g of benzotriazol-1-yloxytris (dimethylamino)phosphonium hexafluorophosphate (59 mmol, 1.2 eq) was added all at once and the mixture stirred at room temperature for 2 hours. The reaction mixture was added to 300 mL of ethyl acetate and washed three times with 5% aqueous citric acid, twice with saturated aqueous sodium bicarbonate and once with saturated aqueous sodium chloride. The organic layer was removed, dried over magnesium sulfate, filtered and the filtrate concentrated under vacuum. The residue was purified by preparative high pressure liquid chromatography on silica, eluting with ethyl acetate/hexane (4:1), to afford 17.42 g (46.4 mmol, 94%) of the product as a white solid. $^1$H NMR (200 MHz,CDCl$_3$): 1.37 (s,6H), 1.44 (s,9H), 1.95 (m,1H), 2.46 (d,15 Hz,1H), 2.59 (d,15 Hz,1H), 2.6–3.0, (m,3H), 4.53 (m,1H), 5.30 (br s,1H), 6.72 (d,7 Hz,1H), 6.98 (d,8 Hz,1H), 7.1–7.3 (m,3H), 7.82 (br s,1H). FAB-MS: calculated for $C_{20}H_{29}N_3O_4$ 375; found 376 (M+H,70%).

Step J: 2-Hydroxy-5-methylbenzaldehyde

Methylmagnesium chloride solution in tetrahydrofuran (100 mL, 3.0M, 300 mmol) at room temperature was treated dropwise over 30 minutes with a solution of 32.3 g (300 mmol) of p-cresol in 30 mL of tetrahydrofuran. An additional 70 mL of tetrahydrofuran was added to moderate the exothermic reaction. The mixture was aged at room temperature for 2 hours then treated with 400 mL of toluene, 41mg of 1,3-dimethyl-3,4,5,6-tetrahydro-2(1H)-pyrimidinone and 23 g of paraformaldehyde. The reaction mixture was heated at reflux for 18 hours, then cooled and washed with 200 mL of 2N aqueous hydrochloric acid and 200 mL of water. The organic layer was removed, filtered through Celite, dried over magnesium sulfate, filtered and solvents removed under vacuum. Crystallization of the crude residue from cold hexanes gave 7.4 g (54 mmol, 18%) of the product. The mother liquors were further purified by column chromatography on silica gel, eluting with methylene chloride, to give an additional 17.5 g (128 mmol, 43%) of the product. $^1$H NMR (200 MHz,CDCl$_3$): 2.33 (s,3H), 6.89 (d,10 Hz,1H), 7.33 (m,2H), 9.83 (s,1H), 10.80 (s,1H).

Step K: 2-(2-Cyanophenyl)-5-methylbenzofuran

A 500 mL 3-neck round bottom flask equipped with a magnetic stirrer, dropping funnel, thermometer and nitrogen bubbler was charged with 10.7 g (108 mmol) of sodium methoxide and 75 mL of absolute ethanol. A solution of 24.9 g (183 mmol) of 2-hydroxy-5-methylbenzaldehyde in 75 mL of dry dimethylformamide was added dropwise over 15 minutes. The mixture was stirred for 20 minutes then treated dropwise over 20 minutes with a solution of 34.8 g (177 mmol) of α-bromo-o-tolunitrile in 75 mL of dry dimethylformamide. The mixture was heated at 75° C. for 30 minutes, then allowed to cool for one hour. A suspension of 10.7 g (188 mmol) of sodium methoxide in 20 mL of dry dimethylformamide was added and the resulting mixture heated at 90° C. for 1.5 hours. The reaction mixture was concentrated under vacuum at 50° C. to give a brown solid that was slurried in 100–200 mL of cold water and filtered. The solids were triturated with 200 mL of methanol, filtered, washed with additional methanol, then air dried. After drying in a dessicator under high vacuum, 26.1 g (112 mmol, 63%) of the product was isolated as a beige solid. $^1$H NMR (200 MHz,CDCl$_3$): 2.45 (s,3H), 7.17 (d,8 Hz,1H), 7.4 (m,3H), 7.6–7.8 (m,3H), 8.10 (d,8 Hz,1H).

Step L: 2-[2-(1H-Tetrazol-5-yl)phenyl]-5-methylbenzofuran

A 500 mL 3-neck round bottom flask equipped with a magnetic stirrer, condenser, thermometer and nitrogen bubbler was charged with 19.1 g (82 mmol) of 2-(2-cyanophenyl)-5-methylbenzofuran, 200 mL of toluene and 25.6 g (124 mmol) of trimethyltin azide. The suspension was heated at reflux for 20 hours, then an additional 10.0 g (48 mmol) of trimethyltin azide was added and heating at reflux was continued for another 24 hours. Additional trimethyltin azide (5.8 g, 27 mmol) was added and refluxing continued for 5 hours. The reaction mixture was cooled to room temperature and solids were removed by filtration and washed with hexane and air dried. The solids were partitioned between 400 mL of 2N aqueous sodium hydroxide and 400 mL of ethyl acetate. The layers were separated and the aqueous layer was acidified by the addition of 2N hydrochloric acid, then extracted with 100 mL of ethyl acetate. The combined extracts were washed with saturated aqueous sodium chloride, dried over magnesium sulfate, filtered and refrigerated for 48 hours. The crystals that formed were removed by filtration, washed with hexane and air dried to give 12.97 g (47 mmol, 57%) of the product as fluffy, white crystals. $^1$H NMR (200 MHz,CDCl$_3$): 2.38 (s,3H), 6.27 (s,1H), 7.05 (d,8 Hz,1H), 7.25 (m,2H), 7.4–7.7 (m,3H), 7.90 (d,8 Hz,1H).

Step M: 3-Bromo-2-[2-(1H-tetrazol-5-yl)phenyl]-5-methylbenzofuran

A 1 L 3-neck round bottom flask equipped with a magnetic stirrer, thermometer, dropping funnel and nitrogen bubbler was charged with 12.97 g (46.9 mmol) of 2-[2-(1H-tetrazol-5-yl)phenyl]-5-methylbenzofuran and 500 mL of 1,4-dioxane. To the well-stirred solution at room temperature was added a solution of 4.8 mL (93.2 mmol) of bromine in 35 mL of carbon tetrachloride dropwise over 1 hour. Cyclohexene (16 mL) was added to the reaction mixture then it was concentrated under vacuum to an oily residue that was partitioned between 100 mL of 1N aqueous sodium hydroxide and 100 mL of ether. The aqueous layer was removed, acidified with 50 mL of 2N aqueous hydrochloric acid, and extracted several times with ethyl acetate. The combined extracts were washed with saturated aqueous sodium chloride, dried over magnesium sulfate, filtered and concentrated under vacuum to give a white foam that was triturated with 100 mL of hot toluene. The mixture was cooled in an ice bath and the solids removed by filtration then washed with cold toluene, air dried and dried under vacuum to give 14.11 g (39.7 mmol, 85%) of product. $^1$H NMR (200 MHz,CDCl$_3$+1 drop DMSO-d$_6$): 2.44 (s,3H), 7.1–7.3 (m,4H), 7.6 (m,2H), 7.86 (m,1H), 7.95 (m,1H).

Step N: 3-Bromo-2-[2-[(N-triphenylmethyl)tetrazol-5-yl]phenyl]-5-methylbenzofuran A suspension of 14.1 g (39.7 mmol) of 3-bromo-2-[2-(1H-tetrazol-5-yl)phenyl]-5-methylbenzofuran in 400 mL of methylene chloride in a 1 L 3-neck round bottom flask equipped with a magnetic stirrer, thermometer and nitrogen bubbler was treated with 11 mL (79 mmol) of triethylamine, 11.1 g (39.8 mol) of triphenylmethyl chloride followed by 140 mg (1.1 mmol) of 4-dimethylaminopyridine. The reaction mixture was stirred at room temperature for one hour, then transferred to a separatory funnel and washed with 100 mL of water and 100 mL of saturated aqueous sodium chloride. The organic layer was removed, dried over magnesium sulfate, filtered and chromatographed on 200 g of silica gel to give 20 g of a crude product which was triturated with ether to afford 18.35 g (30.7 mmol, 77%) of the product as a white solid. $^1$H NMR (200 MHz,CDCl$_3$): 2.46 (s,3H), 6.8–7.0 (m,8H), 7.1–7.4 (m,10H), 7.58 (m,2H), 7.72 (m,1H), 8.20 (m,1H).

Step O: 3-Bromo-2-[2-[(N-triphenylmethyl)tetrazol-5-yl]phenyl]-5-(bromomethyl)benzofuran A 2 L 3-neck round bottom flask equipped with a magnetic stirrer, thermometer, condenser and nitrogen bubbler was charged with 18.35 g (30.7 mmol) of 3-bromo-2-[2-[(N-triphenylmethyl)tetrazol-5-yl]phenyl]-5-methylbenzofuran and 500 mL of carbon tetrachloride. The resulting suspension was heated at reflux briefly to dissolve the starting material. The mixture was cooled to 50° C. and treated with 5.52 g (31.0 mmol) of N-bromosuccinimide and 275 mg (1.13 mmol) of benzoyl peroxide. The reaction mixture was heated at reflux for three hours, then cooled to room temperature and washed with 100 mL of water and 100 mL of saturated aqueous sodium chloride. The organic layer was removed, dried over magnesium sulfate, filtered and concentrated under vacuum to a white foam. Trituration with 100 mL of ether/methanol (1:1) gave 20 g of solids that were removed by filtration. The crude product thus obtained was stirred for 16 hours in 100 mL of ether/methanol (1:1), filtered, washed with additional ether/methanol (1:1), and dried under vacuum to give 17.4 g of product. $^1$H NMR analysis of the product shows it to be a mixture containing 85% of the desired bromomethyl product in addition to 15% of the starting methyl compound. $^1$H NMR (200 MHz, CDCl$_3$): 4.63 (s,2H), 6.85 (m,6H), 7.0–7.4 (m,10H), 7.45 (s,1H), 7.55–7.75 (m,4H), 8.23 (d,7 Hz,1H).

Step P: 3-t-Butoxycarbonylamino-N-[1-[[3-bromo-2-[2-(N-triphenylmethyl)tetrazol-5-yl]phenyl]-5-benzofuranyl]methyl]-2,3,4,5-tetrahydro-2-oxo-1H-1-benzazepin-3(R)-yl]-3-methylbutanamide A solution of 200 mg (0.533 mmol) of 3-t-butoxycarbonylamino-3-methyl-N-[2,3,4,5-tetrahydro-2-oxo-1H-1-benzazepin-3(R)-yl]-butanamide (Step I) in 5 mL of dry dimethylformamide was treated with 28 mg of 60% sodium hydride oil dispersion (17 mg NaH, 0.70 mmol, 1.3 eq). The reaction mixture was stirred at room temperature for 30 minutes. To the solution was added a solution of 541 mg (0.80 mmol) of 3-bromo-2-[2-[(N-triphenylmethyl) tetrazol-5-yl]phenyl]-5-(bromomethyl)benzofuran in 3 mL of dry dimethylformamide. After stirring at room temperature for 1 hour, the reaction mixture was diluted with ethyl acetate. The organic layer was washed with water (4×), dried over magnesium sulfate, filtered and evaporated under vacuum to give 245 mg (0.25 mmol, 47%) of crude product that was used in the next step without purification. $^1$H NMR (400 MHz, CD$_3$OD): 1.35 (s,6H), 1.43 (s,9H), 2.00 (m,1H), 2.30 (m,2H), 2.41 (m,1H), 2.47 (d,14 Hz,1H), 2.62 (d,14 Hz,1H), 4.38 (dd;7,12 Hz;1H), 4.97 (d,15 Hz,1H), 5.43 (d,15 Hz,1H), 6.78 (d,8 Hz,6H), 6.97 (d,8 Hz,1H), 7.1–7.4 (m,15H), 7.68 (m,3H), 8.15 (d,7 Hz,1H).

Step Q: 3-Amino-N-[1-[[3-bromo-2-[2-(1H-tetrazol-5-yl) phenyl]-5-benzofuranyl]methyl]-2,3,4,5-tetrahydro-2-oxo-1H-1-benzazepin-3(R)-yl]-3-methylbutanamide, trifluoroactate The intermediate obtained in Step P (243 mg, 0.25 mmol) was partitioned between 30 mL of hexane and 30 mL of methanol and the resulting two-phase system stirred vigorously while 20 mL of 9N aqueous hydrochloric acid was slowly added. The mixture was stirred at room temperature for 2 hours, then stirring was discontinued and the layers allowed to separate. The aqueous layer was removed, concentrated under vacuum, and the residue purified by reverse phase medium pressure liquid chromatography on C8, eluting with methanol/0.1% aqueous trifluoroacetic acid (60:40), to give 160 mg (0.22 mmol, 86%) of the title compound as a white solid. $^1$H NMR (400 MHz,CD$_3$OD): 1.35 (s,3H), 1.38 (s,3H), 2.10 (m,1H), 2.32 (m,1H), 2.52 (m,4H), 4.40 (dd;8,12 Hz;1H), 4.99 (d, 15 Hz,1H), 5.43 (d,15 Hz,1H), 7.22 (d,5 Hz,2H), 7.27 (s,2H), 7.30–7.45 (m,3H), 7.74 (m,2H), 7.85 (d,8 Hz,1H), 7.94 (d,8 Hz,1H). FAB-MS: calculated for C$_{31}$H$_{30}$BrN$_7$O$_3$ 627,629; found 628 (10%), 630 (17%).

EXAMPLE 2

3-Amino-N-[1-[[2-[2-(1H-tetrazol-5-yl)phenyl]-5-benzofuranyl]methyl]-2,3,4,5-tetrahydro-2-oxo-1H-1-benzazepin-3(R)-yl]-3-methylbutanamide, trifluoroacetate A solution of 146 mg (0.197 mmol) of 3-amino-N-[1-[[3-bromo-2-[2-(1H-tetrazol-5-yl)phenyl]-5-benzofuranyl]methyl]-2,3,4,5-tetrahydro-2-oxo-1H-1-benzazepin-3(R)-yl]-3-methylbutanamide, trifluoroacetate (Example 1) in 10 mL of methanol was treated with several drops of trifluoroacetic acid and hydrogenated at ambient temperature and 40 psi over 50 mg of 10% palladium on carbon for 12 hours. The mixture was filtered through Celite and the filtrate concentrated under vacuum. The crude product was purified by reverse phase high pressure liquid chromatography on C18, eluting with methanol/0.1% aqueous trifluoroacetic acid (linear gradient: 60% methanol increased to 80% methanol over ten minutes), to give 107 mg (0.161 mmol, 82%) of the title compound as a colorless glass. FAB-MS: calculated for C$_{31}$H$_{31}$N$_7$O$_3$ 549; found 551 (5%). $^1$H NMR (400 MHz,CD$_3$OD): 1.36 (s,3H), 1.40 (s,3H), 2.10 (m,1H), 2.32 (m,1H), 2.55 (m,4H), 4.38 (dd;8,12 Hz;1H), 4.9 (d,15 Hz,1H), 5.38 (d,15 Hz,1H), 6.56 (s,1H), 7.18 (br s,4H), 7.35 (m,2H), 7.43 (s,1H), 7.62 (m,2H), 7.73 (t,7 Hz,1H), 8.00 (d,7 Hz,1H).

EXAMPLE 3

3-[2(R)-Hydroxypropyl]amino-N-[1-[[3-bromo-2-[2-(1H-tetrazol-5-yl)phenyl]-5-benzofuranyl]methyl]-2,3,4,5-tetrahydro-2-oxo-1H-1-benzazepin-3(R)-yl]-3-methylbutanamide, trifluoroacetate Step A: 3-Amino-3-methyl-N-[2,3,4,5-tetrahydro-2-oxo-1H-1-benzazepin-3(R)-yl]-butanamide, trifluoroacetate To a solution of 150 mg (0.40 mmol) of 3-t-butoxycarbonylamino-3-methyl-N-[2,3,4,5-tetrahydro-2-oxo-1H-1-benzazepin-3(R)-yl]-butanamide (Example 1, Step I) in 2 mL of methylene chloride at 0° C. was added 2 mL of trifluoroacetic acid and the mixture stirred at room temperature for 1 hour. All volatiles were removed under vacuum to give 130 mg (0.33 mmol, 84%) of the product. $^1$H NMR (200 MHz,CD$_3$OD): 1.33 (s,3H), 1.37 (s,3H), 2.12 (m,1H), 2.3–2.6 (m,3H), 2.6–3.0 (m,2H), 4.37 (dd;8,12 Hz;1H), 7.02 (d,8 Hz,1H), 7.1–7.3 (m,3H). FAB-MS: calculated for C$_{15}$H$_{21}$N$_3$O$_2$ 275; found 276 (M+H,100%).

Step B: 3-[2(R)-Benzyloxypropyl]amino-3-methyl-N-[2,3,4,5-tetrahydro-2-oxo-1H-1-benzazepin-3(R)-yl]-butanamide, trifluoroacetate To a solution of 1.0 g (2.57 mmol) of 3-amino-3-methyl-N-[2,3,4,5-tetrahydro-2-oxo-1H-1-benzazepin-3(R)-yl]-butanamide, trifluoroacetate in 25 mL of dry methanol was added 3.0 g of dry 3A powdered molecular sieves followed by a solution of 2.5 g (17 mmol) of (R)-2-benzyloxypropanal (prepared from ethyl-D-lactate according to the procedure of Hanessian and Kloss, Tetrahedron Lett. 1985, 26, 1261–1264.) in 5 mL of dry methanol. The pH of the mixture was carefully adjusted to 6 by the addition of trifluoroacetic acid. The reaction was stirred for 2 hours at room temperature at which time 15.4 mL (15.4 mmol) of a 1.0M solution of sodium cyanoborohydride in tetrahydrofuran was added by syringe. The reaction was stirred for 72 hours then filtered through a pad of Celite. To the filtrate was added 5 mL of trifluoroacetic acid (CAUTION! evolution of hydrogen cyanide) and the resulting mixture was stirred for three hours. The solvent was removed under vacuum to afford a clear oil which was purified by reverse phase medium pressure liquid chromatography on C-8, eluting with methanol/0.1% aqueous trifluoroacetic acid (60:40), to afford 1.27 g (2.36 mmol, 92%) of the product as a white solid. $^1$H NMR (200 MHz, CD$_3$OD): 1.31 (d,6 Hz,3H), 1.40 (s,3H), 1.43 (s,3H), 2.17 (m,1H), 2.30 (m,1H), 2.6–3.1 (m,5H), 3.22 (dd;3,12 Hz;1H), 3.86 (m,1H), 4.48 (dd;7,12 Hz;1H), 4.50 (d,12 Hz,1H), 4.70 (d,12 Hz,1H), 7.11 (d,8 Hz,1H), 7.15–7.45 (m,8H). FAB-MS: calculated for C$_{25}$H$_{33}$N$_3$O$_3$ 423; found 424 (M+H,100%).

Step C: 3-[2(R)-Benzyloxypropyl]amino-3-methyl-N-[2,3,4,5-tetrahydro-2-oxo-1H-1-benzazepin-3(R)-yl]-butanamide To a solution of 2.034 g (3.788 mmol) of the intermediate obtained in Step B in 40 mL of methylene chloride was added 40 mL of water. The mixture was stirred vigorously while sufficient solid potassium carbonate was added to adjust the pH of the aqueous layer to 10–11. Stirring was discontinued and the layers allowed to separate. The organic layer was removed and the aqueous layer extracted twice more with methylene chloride. The combined extracts were dried over potassium carbonate, filtered and solvents removed under vacuum to afford 1.53 g (3.62 mmol, 95%) of the product as a white solid.

Step D: 3-[2(R)-Benzyloxypropyl]amino-N-[1-[[3-bromo-2-[2-(1H-tetrazol-5-yl)phenyl]-5-benzofuranyl]methyl]-2,3,4,5-tetrahydro-2-oxo-1H-1-benzazepin-3(R)-yl]-3-methylbutanamide, trifluoroacetate A solution of 69 mg (0.16 mmol) of the intermediate obtained in Step C in 2.5 mL of dry dimethylformamide under a nitrogen atmosphere was treated with 8 mg of 60% sodium hydride/oil dispersion (4.8 mg NaH, 0.20 mmol) and the resulting mixture stirred at room temperature for 30 minutes. To this was added a solution of 166 mg (0.25 mmol) of 3-bromo-2-[2[-(N-triphenytriphenylmethyl)

tetrazol-5-yl]phenyl]-5-(bromoethyl)benzofuran in 0.5 mL of dry dimethylformamide and the resulting mixture stirred at room temperature for 1 hour. The reaction mixture was diluted with 20 mL of ethyl acetate and washed with saturated aqueous sodium chloride which had been made slightly basic by the addition of several drops of concentrated ammonium hydroxide. The organic layer was removed, dried over magnesium sulfate, filtered and concentrated under vacuum to a gummy residue.

The residue was partitioned between 20 mL of hexane and 20 mL of methanol, then treated with 10 mL of 9N aqueous hydrochloric acid. The two-phase mixture was stirred vigorously for two hours then stirring was discontinued and the layers allowed to separate. The aqueous layer was removed and concentrated under vacuum. The crude was purified by reverse phase medium pressure liquid chromatography on C8, eluting with methanol/0.1% aqueous trifluoroacetic acid (70:30), to give 145 mg (0.16 mmol, 100%) of the product as a white solid. $^1$H NMR (400 MHz,CD$_3$OD): 1.29 (d,7 Hz,3H), 1.34 (s,3H), 1.35 (s,3H), 2.13 (m,1H), 2.33 (m,1H), 2.58 (m,3H), 2.68 (d,16 Hz,1H), 2.95 (dd;8,12 Hz;1H), 3.20 (dd;3,12 Hz;1H), 3.83 (m,1H), 4.45 (d,12 Hz,1H), 4.46 (dd;8,12 Hz;1H), 4.67 (d,12 Hz,1H), 5.08 (d,15 Hz,1H), 5.30 (d,15 Hz,1H), 7.18 (m,3H), 7.27 (m,4H), 7.39 (m,5H), 7.75 (m,2H), 7.86 (d,7 Hz,1H), 7.94 (d,7 Hz,1H). FAB-MS: calculated for C$_{41}$H$_{42}$BrN$_7$O$_4$ 775,777; found 790 (M+Na, 40%).

Step E: 3-[2(R)-Hydroxypropyl]amino-N-[1-[[3-bromo-2-[2-(1H-tetrazol-5-yl)phenyl]-5-benzofuranyl]methyl]-2,3,4,5-tetrahydro-2-oxo-1H-1-benzazepin-3(R)-yl]-3-methylbutanamide, trifluoroacetate A solution of 53.4 mg (0.060 mmol) of the intermediate obtained in Step D in 1 mL of 30% hydrobromic acid in acetic acid was stirred at room temperature for two hours then evaporated to dryness under vacuum to give a yellow solid that was used the next step without purification.

The crude intermediate thus obtained was dissolved in 2 mL of methanol, cooled to 0° C. and treated with 0.20 mL of a 25% (weight/volume) solution of sodium methoxide in methanol. The mixture was stirred at room temperature for 5 minutes then treated with several drops of trifluoroacetic acid. All volatiles were removed under vacuum and the residue purified by reverse phase medium pressure liquid chromatography on C8, eluting with methanol/0.1% aqueous trifluoroacetic acid (65:35), to afford 34 mg (0.043 mmol, 71%) of the title compound as a white solid. $^1$H NMR (400 Hz, CDCl$_3$): 1.24 (d,7 Hz,3H), 1.36 (s,3H), 1.40 (s,3H), 2.12 (m,1H), 2.32 (m,1H), 2.55 (m,2H), 2.58 (d,16 Hz,1H), 2.67 (d,16 Hz,1H), 2.80 (dd;9,12 Hz;1H), 3.10 (dd;3,12 Hz;1H), 3.92 (m,1H), 4.39 (dd;8,12 Hz;1H), 5.03 (d,16 Hz,1H), 5.39 (d,16 Hz,1H), 7.21 (d,8 Hz,2H), 7.25–7.40 (m,5H), 7.74 (m,2H), 7.85 (d,8 Hz,1H), 7.95 (d,8 Hz,1H). FAB-MS: calculated for C$_{34}$H$_{36}$BrN$_7$O$_4$ 685,687; found 686 (40%), 688 (42%).

What is claimed is:

1. A compound having the formula:

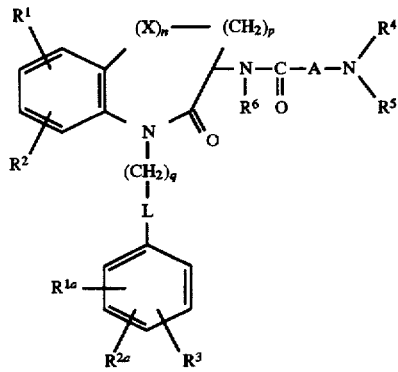

where L is

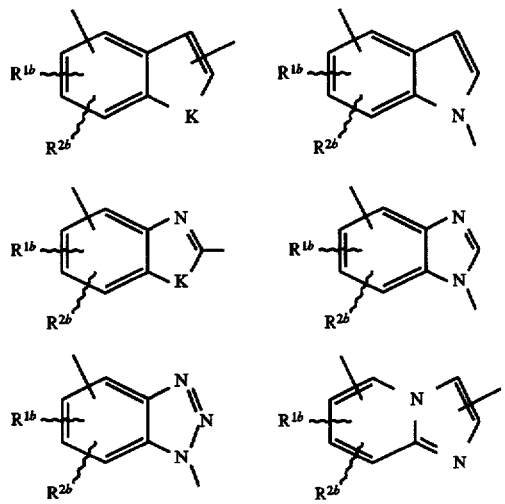

where K is O, S or N—R$^{13}$; and R$^{1b}$ and R$^{2b}$ may be attached to either ring of the benzo-fused heterocycle;

n is 0 or 1;
p is 0 to 3;
q is 0 to 4;
X is O or S(O)$_m$.

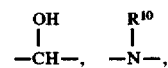

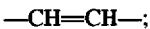

—CH=CH—;

m is 0 to 2;

R$^1$, R$^2$, R$^{1a}$, R$^{2a}$, R$^{1b}$, and R$^{2b}$ are independently hydrogen, halogen, C$_1$–C$_7$ alkyl, C$_1$–C$_3$ perfluoroalkyl, C$_1$–C$_3$ perfluoroalkoxy, —S(O)$_m$R$^{7a}$, cyano, nitro, R$^{7b}$O(CH$_2$)$_v$—, R$^{7b}$COO(CH$_2$)$_v$—, R$^{7b}$OCO(CH$_2$)$_v$—, R$^4$R$^5$N(CH$_2$)$_v$—, R$^{7b}$CON(R$^4$)(CH$_2$)$_v$—, R$^4$R$^5$NCO (CH$_2$)$_v$—, phenyl or substituted phenyl where the substituents are from 1 to 3 of halogen, C$_1$–C$_6$ alkyl, C$_1$–C$_6$ alkoxy, or hydroxy; R$^{7a}$ and R$^{7b}$ are independently hydrogen, C$_1$–C$_3$ perfluoroalkyl, C$_1$–C$_6$ alkyl, substituted C$_1$–C$_6$ alkyl, where the substituents are phenyl or substituted phenyl; phenyl or substituted phenyl where the phenyl substituents are from 1 to 3 of halogen, C$_1$–C$_6$ alkyl, C$_1$–C$_6$ alkoxy, or hydroxy and v is 0 to 3;

$R^3$ is hydrogen, $R^9$, $C_1$-$C_6$ alkyl substituted with $R^9$, phenyl substituted with $R^9$, or phenoxy substituted with $R^9$;

$R^9$ is

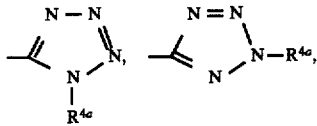

$R^{7b}O(CH_2)_v$—, $R^{7b}COO(CH_2)_v$—, $R^{7b}OCO(CH_2)_v$—, $R^{7b}CO(CH_2)_v$—, $R^{7b}(CH_2)_vCO$—, $R^4R^5N(CH_2)_v$—, $R^{7b}CON(R^4)(CH_2)_v$—, $R^4R^5NCO(CH_2)_v$, $R^4R^5NCS(CH_2)_v$—, $R^4R^5NN(R^5)CO(CH_2)_v$—, $R^4R^5NN(R^5)CS(CH_2)_v$—, $R^{7b}CON(R^4)N(R^5)CO(CH_2)_v$—, $R^{7b}CON(R^4)N(R^5)CS(CH_2)_v$—, $R^4N(OR^{7b})CO(CH_2)_v$—, $R^{7a}CON(OR^{7b})CO(CH_2)_v$—, $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CSN(R^{12c})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 3;

$R^{12a}$, $R^{12b}$ and $R^{12c}$ are independently $R^{5a}$, $OR^{5a}$, or $COR^{5a}$; $R^{12a}$ and $R^{12b}$, or $R^{12b}$ and $R^{12c}$, or $R^{13}$ and $R^{12b}$, or $R^{12a}$ and $R^{4b}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3 and $R^1$ and $R^{10}$ are as defined;

$R^{13}$ is $C_1$-$C_3$ perfluoroalkyl, $C_1$-$C_6$ alkyl, substituted $C_1$-$C_6$ alkyl, where the substitutents are hydroxy, —NR$^{10}$R$^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy; where $R^{10}$ and $R^{11}$ are independently hydrogen, $C_1$-$C_6$ alkyl, phenyl, phenyl $C_1$-$C_6$ alkyl, $C_1$-$C_5$-alkoxycarbonyl, or $C_1$-$C_5$-alkanoyl-$C_1$-$C_6$ alkyl;

$R^4$, $R^{4a}$, $R^{4b}$, and $R^5$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl, or substituted $C_3$-$C_{10}$ alkynyl where the substituents on the phenyl, alkyl, alkenyl or alkynyl are from 1 to 5 of hydroxy, $C_1$-$C_6$ alkoxy, $C_3$-$C_7$ cycloalkyl, fluoro, $R^1$, $R^2$ independently disubstituted phenyl $C_1$-$C_3$ alkoxy, $R^1$, $R^2$ independently disubstituted phenyl, $C_1$-$C_{20}$-alkanoyloxy, $C_1$-$C_5$ alkoxycarbonyl, carboxy, formyl, or —NR$^{10}$R$^{11}$; or $R^4$ and $R^5$ can be taken together to form —(CH$_2$)$_r$B(CH$_2$)$_s$— where B, r, s, $R^1$, $R^2$, $R^{10}$ and $R^{11}$ are as defined above;

$R^6$ is hydrogen, $C_1$-$C_{10}$ alkyl, phenyl or phenyl $C_1$-$C_{10}$ alkyl;

A is

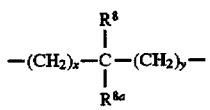

where x and y are independently 0–3;

$R^8$ and $R^{8a}$ are independently hydrogen, $C_1$-$C_{10}$ alkyl, trifluoromethyl, phenyl, substituted $C_1$-$C_{10}$ alkyl where the substituents are from 1 to 3 of imidazolyl, indolyl, hydroxy, fluoro, S(O)$_m$R$^{7a}$, $C_1$-$C_6$ alkoxy, $C_3$-$C_7$ cycloalkyl, $R^1$, $R^2$ independently disubstituted phenyl $C_1$-$C_3$ alkoxy, $R^1$, $R^2$ independently disubstituted phenyl, $C_1$-$C_5$-alkanoyloxy, $C_1$-$C_5$ alkoxycarbonyl, carboxy, formyl, or —NR$^{10}$R$^{11}$ where $R^1$, $R^2$, $R^{10}$ and $R^{11}$ are as defined above; or $R^8$ and $R^{8a}$ can be taken together to form —(CH$_2$)$_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

2. A compound of claim 1 wherein:

n is 0 or 1;

p is 0 to 3;

q is 0 to 2;

L is as defined in claim 1,

X is O or S(O)$_m$;

m is 0 to 2;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —S(O)$_m$R$^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl; phenyl and v is 0 to 2;

$R^3$ is hydrogen, $R^9$, $C_1$-$C_6$ alkyl substituted with $R^9$, phenyl substituted with $R^9$, or phenoxy substituted with $R^9$;

$R^9$ is

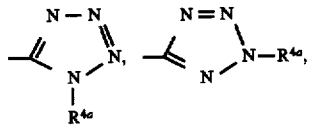

$R^{7b}O(CH_2)_v$—, $R^{7b}COO(CH_2)_v$—, $R^{7b}OCO(CH_2)_v$—, $R^{7b}CO(CH_2)_v$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4R^5NN(R^5)CO(CH_2)_v$—, $R^{7b}CON(R^4)N(R^5)CO(CH_2)_v$—, $R^4N(OR^{7b})CO(CH_2)_v$—, $R^{7a}CON(OR^{7b})CO(CH_2)_v$—, $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 3;

$R^{12a}$, $R^{12b}$ and $R^{12c}$ are independently $R^{5a}$, $OR^{5a}$ or $COR^{5a}$; $R^{12a}$ and $R^{12b}$, or $R^{12b}$ and $R^{12c}$, or $R^{13}$ and $R^{12b}$ or $R^{12a}$ and $R^{4b}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 3, $R^1$ is as defined above and $R^{10}$ is hydrogen, $C_1$-$C_6$ alkyl, phenyl $C_1$-$C_6$ alkyl or $C_1$-$C_5$ alkanoyl-$C_1$-$C_6$ alkyl;

$R^{13}$ is $C_1$-$C_3$ perfluoroalkyl, $C_1$-$C_6$ alkyl, substituted $C_1$-$C_6$ alkyl, where the substituents are hydroxy,

67

—NR$^{10}$R$^{11}$, carboxy, phenyl or substituted phenyl; phenyl or substituted phenyl where the substituents on the phenyl are from 1 to 3 of halogen, C$_1$–C$_6$ alkyl, C$_1$–C$_6$ alkoxy or hydroxy;

R$^4$, R$^{4a}$, R$^{4b}$, and R$^5$ are independently hydrogen, phenyl, substituted phenyl, C$_1$–C$_{10}$ alkyl, substituted C$_1$–C$_{10}$ alkyl, where the substituents on the alkyl or phenyl are from 1 to 5 of hydroxy, C$_1$–C$_6$ alkoxy, C$_3$–C$_7$ cycloalkyl, fluoro, R$^1$, R$^2$ independently disubstituted phenyl C$_1$–C$_3$ alkoxy, R$^1$, R$^2$ independently disubstituted phenyl, C$_1$–C$_{20}$-alkanoyloxy, C$_1$–C$_5$ alkoxycarbonyl, carboxy or formyl;

R$^4$ and R$^5$ can be taken together to form —(CH$_2$)$_r$B(CH$_2$)$_s$— where B is CHR$^1$, O, S(O)$_m$ or N—R$^{10}$, r and s are independently 1 to 3 and R$^1$ and R$^{10}$ are as defined above;

R$^6$ is hydrogen, C$_1$–C$_{10}$ alkyl or phenyl C$_1$–C$_{10}$ alkyl;

A is

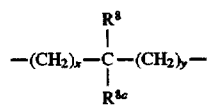

where x and y are independently 0–2;

R$^8$ and R$^{8a}$ are independently hydrogen, C$_1$–C$_{10}$ alkyl, substituted C$_1$–C$_{10}$ alkyl where the substituents are from 1 to 3 of imidazolyl, indolyl, hydroxy, fluoro, S(O)$_m$R$^{7a}$, C$_1$–C$_6$ alkoxy, R$^1$, R$^2$ independently disubstituted phenyl, C$_1$–C$_5$-alkanoyloxy, C$_1$–C$_5$ alkoxycarbonyl, carboxy, formyl or —NR$^{10}$R$^{11}$ where R$^{10}$ and R$^{11}$ are independently hydrogen, C$_1$–C$_6$ alkyl or C$_1$–C$_5$ alkanoyl-C$_1$–C$_6$ alkyl; or R$^8$ and R$^{8a}$ can be taken together to form —(CH$_2$)$_t$— where t is 2 to 4; and R$^8$ and R$^{8a}$ can independently be joined to one or both of R$^4$ and R$^5$ to form alkylene bridges between the terminal nitrogen and the alkyl portion of the A group wherein the bridge contains from 1 to 5 carbon atoms;

and pharmaceutically acceptable salts thereof.

3. A compound of claim 2 wherein:

n is 0 or 1;

p is 0 to 2;

q is 0 to 2;

X is S(O)$_m$, —CH=CH—;

m is 0 or 1;

R$^1$, R$^2$, R$^{1a}$, R$^{2a}$, R$^{1b}$, and R$^{2b}$ are independently hydrogen, halogen, C$_1$–C$_7$ alkyl, C$_1$–C$_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$, phenyl or substituted phenyl where the substituents are from 1 to 3 of halogen, C$_1$–C$_6$ alkyl, C$_1$–C$_6$ alkoxy, or hydroxy;

R$^{7a}$ and R$^{7b}$ are independently hydrogen, C$_1$–C$_6$ alkyl, substituted C$_1$–C$_6$ alkyl, where the substituents are phenyl and v is 0 to 2;

R$^3$ is hydrogen, R$^9$, C$_1$–C$_6$ alkyl substituted with R$^9$, phenyl substituted with R$^9$ or phenoxy substituted with R$^9$;

68

R$^9$ is

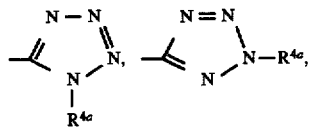

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^4$R$^5$N(CH$_2$)$_v$—, R$^{7b}$CON(R$^4$)(CH$_2$)$_v$—, R$^4$R$^5$NCO(CH$_2$)$_v$—, R$^4$R$^5$NCS(CH$_2$)$_v$—, R$^4$N(OR$^{7b}$)CO(CH$_2$)$_v$—, R$^{7a}$CON(OR$^{7b}$)CO(CH$_2$)$_v$—, R$^{4b}$R$^{12a}$NCON(R$^{12b}$)(CH$_2$)$_v$—, R$^{4b}$R$^{12a}$NCSN(R$^{12b}$)(CH$_2$)$_v$—, R$^{4b}$R$^{12a}$NN(R$^{12b}$)CON(R$^{12c}$)(CH$_2$)$_v$—, R$^{4b}$R$^{12a}$NN(R$^{12b}$)COO(CH$_2$)$_v$—, R$^{4b}$R$^{12a}$NCOO(CH$_2$)$_v$— or R$^{13}$OCON(R$^{12b}$)(CH$_2$)$_v$—, where v is 0 to 2;

R$^{12a}$, R$^{12b}$ and R$^{12c}$ are independently R$^{5a}$ or OR$^{5a}$, R$^{12a}$ and R$^{12b}$, or R$^{12b}$ and R$^{12c}$, or R$^{13}$ and R$^{12b}$ or R$^{12a}$ and R$^{4b}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 2, R$^1$ is as defined above, and R$^{10}$ is hydrogen, C$_1$–C$_6$ alkyl or C$_1$–C$_5$ alkanoyl-C$_1$–C$_6$ alkyl;

R$^{13}$ is C$_1$–C$_6$ alkyl, substituted C$_1$–C$_6$ alkyl, where the substituents are phenyl or substituted phenyl; phenyl or substituted phenyl where the substituents on the phenyl are from 1 to 3 of halogen, C$_1$–C$_6$ alkyl, C$_1$–C$_6$ alkoxy or hydroxy;

R$^4$, R$^{4a}$, R$^{4b}$, and R$^5$ are independently hydrogen, C$_1$–C$_{10}$ alkyl, substituted C$_1$–C$_{10}$ alkyl, where the substituents on the alkyl are from 1 to 5 of hydroxy, C$_1$–C$_6$ alkoxy, fluoro, R$^1$, R$^2$ independently disubstituted phenyl, C$_1$–C$_{20}$-alkanoyloxy, C$_1$–C$_5$ alkoxycarbonyl or carboxy;

R$^6$ is hydrogen or C$_1$–C$_{10}$ alkyl;

A is

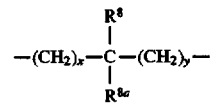

where x and y are independently 0–1;

R$^8$ and R$^{8a}$ are independently hydrogen, C$_1$–C$_{10}$ alkyl, substituted C$_1$–C$_{10}$ alkyl where the substituents are from 1 to 3 of imidazolyl, indolyl, hydroxy, fluoro, S(O)$_m$R$^{7a}$, C$_1$–C$_6$ alkoxy, R$^1$, R$^2$ independently disubstituted phenyl, C$_1$–C$_5$-alkanoyloxy, C$_1$–C$_5$ alkoxycarbonyl, carboxy; or R$^8$ and R$^{8a}$ can be taken together to form —(CH$_2$)$_t$— where t is 2; or R$^8$ and R$^{8a}$ can independently be joined to one or both of R$^4$ and R$^5$ to form alkylene bridges between the terminal nitrogen and the alkyl portion of the A group wherein the bridge contains from 1 to 5 carbon atoms; and pharmaceutically acceptable salts thereof.

4. A compound of claim 3 wherein:

n is 0 or 1;

p is 0 to 2;

q is 1;

X is S(O)$_m$; or —CH=CH—;

m is 0 or 1;

R$^1$, R$^2$, R$^{1a}$, R$^{2a}$, R$^{1b}$, and R$^{2b}$ are independently hydrogen, halogen, C$_1$–C$_7$ alkyl, C$_1$–C$_3$ perfluoroalkyl, —S(O)$_m$R$^{7a}$, R$^{7b}$O(CH$_2$)$_v$—, R$^{7b}$COO(CH$_2$)$_v$—, phenyl or substituted phenyl where the substituents are from 1 to 3 of halogen, $C_1$-$C_6$ alkyl, $C_1$-$C_6$ alkoxy, or hydroxy;

$R^{7a}$ and $R^{7b}$ are independently hydrogen, $C_1$-$C_6$ alkyl, substituted $C_1$-$C_6$ alkyl, where the substituents are phenyl and v is 0 or 1;

$R^3$ is hydrogen, $R^9$, or $C_1$-$C_6$ alkyl substituted with $R^9$;
$R^9$ is

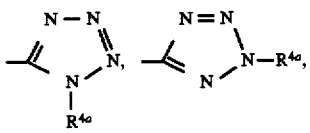

$R^{7b}O(CH_2)_v$—, $R^{7b}COO(CH_2)_v$—, $R^{7b}OCO(CH_2)_v$—, $R^{7b}CO(CH_2)_v$—,
$R^{7b}CON(R^4)(CH_2)_v$—, $R^4R^5NCO(CH_2)_v$—,
$R^4N(OR^{7b})CO(CH_2)_v$—,
$R^{4b}R^{12a}NCON(R^{12b})(CH_2)_v$—,
$R^{4b}R^{12a}NN(R^{12b})CON(R^{12c})(CH_2)_v$—,
$R^{4b}R^{12a}NN(R^{12b})COO(CH_2)_v$—,
$R^{4b}R^{12a}NCOO(CH_2)_v$— or $R^{13}OCON(R^{12b})(CH_2)_v$—,
where v is 0 to 1;

$R^{12a}$, $R^{12b}$ and $R^{12c}$ are independently $R^{5a}$, $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2, $R^1$ is as defined above and $R^{10}$ is hydrogen, $C_1$-$C_6$ alkyl or $C_1$-$C_5$ alkanoyl-$C_1$-$C_6$ alkyl;

$R^{13}$ is $C_1$-$C_6$ alkyl, substituted $C_1$-$C_6$ alkyl, where the substituents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

$R^4$, $R^{4a}$, $R^{4b}$, and $R^5$ are independently hydrogen, $C_1$-$C_{10}$ alkyl, substituted $C_1$-$C_{10}$ alkyl, where the substituents on the alkyl are from 1 to 3 of hydroxy, $C_1$-$C_3$ alkoxy, fluoro, $R^1$, $R^2$ independently disubstituted phenyl, $C_1$-$C_{20}$ alkanoyloxy, $C_1$-$C_5$ alkoxycarbonyl or carboxy;

$R^6$ is hydrogen;

A is

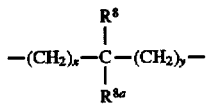

where x and y are independently 0–1;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy; or $R^8$ and $R^{8a}$ can be taken together to form —$(CH_2)_t$— where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

5. A stereospecific compound of claim 1 having the following structural formula:

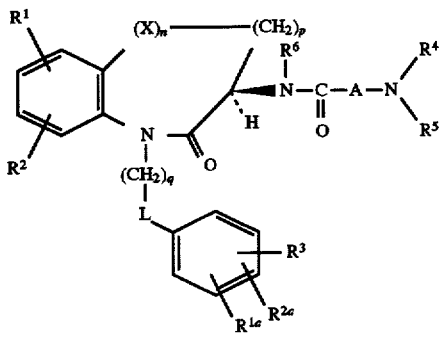

where $R^1$, $R^2$, X, n, p, q, L, $R^{1a}$, $R^{2a}$, $R^3$, $R^4$, $R^5$, $R^6$, and A are as defined in claim 1.

6. A compound of claim 1 which is:

3-Amino-N-[5-[[3-bromo-2-[2-(1H-tetrazol-5-yl)phenyl]-5-benzofuranyl]methyl]-2,3,4,5-tetrahydro-4-oxo-5H-1,5-benzothiazepin-3(S)-yl]-3-methylbutanamide;

3-[2(R)-Hydroxypropyl]amino-N-[5-[[3-bromo-2-[2-(1H-tetrazol-5-yl)phenyl]-5-benzofuranyl]methyl]-2,3,4,5-tetrahydro-4-oxo-5H-1,5-benzothiazepin-3(S)-yl]-3-methylbutanamide;

3-Amino-N-[5-[[3-bromo-2-[2-(1H-tetrazol-5-yl)phenyl]benzo[b]thien-5-yl]methyl]-2,3,4,5-tetrahydro-4-oxo-5H-1,5-benzothiazepin-3(S)-yl]-3-methylbutanamide;

3-[2(R)-Hydroxypropyl]amino-N-[5-[[3-bromo-2-[2-(1H-tetrazol-5-yl)phenyl]benzo[b]thien-5-yl]-methyl]-2,3,4,5-tetrahydro-4-oxo-5H-1,5-benzothiazepin-3(S)-yl]-3-methylbutanamide;

3-Amino-N-[5-[[3-bromo-2-[2-(1H-tetrazol-5-yl)phenyl]-1H-indol-5-yl]methyl]-2,3,4,5-tetrahydro-4-oxo-5H-1,5-benzothiazepin-3(S)-yl]-3-methylbutanamide;

3-[(2(R)-Hydroxypropyl)amino]-N-[5-[[3-bromo-2-[2-(1H-tetrazol-5-yl)phenyl]-1H-indol-5-yl]methyl]-2,3,4,5-tetrahydro-4-oxo-5H-1,5-benzothiazepin-3(S)-yl]-3-methylbutanamide;

(R)-2-[5-[[3-[(3-Amino-3-methyl-1-oxobutyl)amino]-2,3,4,5-tetrahydro-4-oxo-5H-1,5-benzothiazepin-5-yl]methyl]-3-bromo-2-benzofuranyl]-N-ethylbenzamide;

(R)-2-[5-[[3-[[3-[[2(R)-Hydroxypropyl]amino]-3-methyl-1-oxobutyl]amino]-2,3,4,5-tetrahydro-4-oxo-5H-1,5-benzothiazepin-1-yl]methyl]-3-bromo-2-benzofuranyl]-N-ethylbenzamide;

(R)-2-[5-[[3-[[3-[[2(R)-Hydroxypropyl]amino]-3-methyl-1-oxobutyl]amino]-2,3,4,5-tetrahydro-4-oxo-5H-1,5-benzothiazepin-1-yl]methyl]-3-bromo-2-benzofuranyl]-N-ethylbenzamide;

(R)-2-[5-[[3-[(3-Amino-3-methyl-1-oxobutyl)amino]-2,3,4,5-tetrahydro-4-oxo-5H-1,5-benzothiazepin-1-yl]methyl]-3-bromobenzo[b]thien-2-yl]-N-ethylbenzamide;

(R)-2-[5-[[3-[[3-[(2(R)-Hydroxypropyl)amino]-3-methyl-1-oxobutyl]amino]-2,3,4,5-tetrahydro-4-oxo-5H-1,5-benzothiazepin-1-yl]methyl]-3-bromobenzo[b]-thien-2-yl]-N-ethylbenzamide;

(R)-2-[5-[[3-[(3-Amino-3-methyl-1-oxobutyl)amino]-2,3,4,5-tetrahydro-4-oxo-5H-1,5-benzothiazepin-1-yl]methyl]-3-bromo-1H-indol-2-yl]-N-ethylbenzamide;

(R)-2-[5-[[3-[[3-[(2(R)-Hydroxypropyl)amino]-3-methyl-1-oxobutyl]amino]-2,3,4,5-tetrahydro-4-oxo-5H-1,5-benzothiazepin-1-yl]methyl]-3-bromo-1H-indol-2-yl]-N-ethylbenzamide;

3-Amino-N-[5-[[3-bromo-2-[2-[(methylaminocarbonyl)amino]phenyl]-5-benzofuranyl]methyl]-2,3,4,5-tetrahydro-4-oxo-5H-1,5-benzothiazepin-3(S)-yl]-3-methylbutanamide;

3-[(2(R)-Hydroxypropyl)amino]-N-[5-[[3-bromo-2-[2-[(methylaminocarbonyl)amino]phenyl]-5-benzofuranyl]methyl]-2,3,4,5-tetrahydro-4-oxo-5H-1,5-benzothiazepin-3(S)-yl]-3-methylbutanamide;

3-Amino-N-[5-[[3-bromo-2-[2-[(methylaminocarbonyl)amino]phenyl]-1H-indol-5-yl]methyl]-2,3,4,5-tetrahydro-4-oxo-5H-1,5-benzothiazepin-3(S)-yl]-3-methylbutanamide;

3-[(2(R)-Hydroxypropyl)amino]-N-[5-[[3-bromo-2-[2-[(methylaminocarbonyl)amino]phenyl]-1H-indol-5-yl]methyl]-2,3,4,5-tetrahydro-4-oxo-5H-1,5-benzothiazepin-3(S)-yl]-3-methylbutanamide;

3-Amino-N-[5-[[3-bromo-2-[2-[(methylaminocarbonyl)amino]phenyl]benzo[b]thien-5-yl]methyl]-2,3,4,5-tetrahydro-4-oxo-5H-1,5-benzothiazepin-3(S)-yl]-3-methylbutanamide;

3-[(2(R)-Hydroxypropyl)amino]-N-[5-[[3-bromo-2-[2-[(methylaminocarbonyl)amino]phenyl]benzo[b]thien-5-yl]methyl]-2,3,4,5-tetrahydro-4-oxo-5H-1,5-benzothiazepin-3(S)-yl]-3-methylbutanamide;

3-[(2(R)-Hydroxypropyl)amino]-N-[5-[[2-[2-(1H-tetrazol-5-yl)phenyl]-5-benzoxazolyl]methyl]-2,3,4,5-tetrahydro-4-oxo-5H-1,5-benzothiazepin-3(S)-yl]-3-methylbutanamide;

(R)-2-[5-[[3-[[3-[(2(R)-Hydroxypropyl)amino]-3-methyl-1-oxobutyl]amino]-2,3,4,5-tetrahydro-4-oxo-5H-1,5-benzothiazepin-1-yl]methyl]-2-benzoxazolyl]-N-ethylbenzamide;

3-[(2(R)-Hydroxypropyl)amino]-N-[5-[[3-bromo-2-[2-(hydroxymethyl)phenyl]-5-benzofuranyl]methyl]-2,3,4,5-tetrahydro-4-oxo-5H-1,5-benzothiazepin-3(S)-yl]-3-methylbutanamide;

3-[(2(R)-Hydroxypropyl)amino]-N-[5-[[2-[2-[(methylaminocarbonyl)amino]phenyl]-5-benzoxazolyl]methyl]-2,3,4,5-tetrahydro-4-oxo-5H-1,5-benzothiazepin-3(S)-yl]-3-methylbutanamide;

2-Amino-N-[5-[[3-bromo-2-[2-(hydroxymethyl)phenyl]-5-benzofuranyl]methyl]-2,3,4,5-tetrahydro-4-oxo-5H-1,5-benzothiazepin-3(S)-yl]-2-methylpropanamide;

3-[(2(R)-Hydroxypropyl)amino]-N-[5-[[3-bromo-2-[2-(hydroxymethyl)phenyl]benzo[b]thien-5-yl]methyl]-2,3,4,5-tetrahydro-4-oxo-5H-1,5-benzothiazepin-3(S)-yl]-3-methylbutanamide;

2-Amino-N-[5-[[3-bromo-2-[2-(hydroxymethyl)phenyl]benzo[b]thien-5-yl]methyl]-2,3,4,5-tetrahydro-4-oxo-5H-1,5-benzothiazepin-3(S)-yl]-2-methylpropanamide;

3-[(2(R)-Hydroxypropyl]amino-N-[5-[[3-bromo-2-[2-(hydroxymethyl)phenyl]-1H-indol-5-yl]methyl]-2,3,4,5-tetrahydro-4-oxo-5H-1,5-benzothiazepin-3(S)-yl]-3-methylbutanamide; or 3-[(2(R)-Hydroxypropyl)amino]-N-[1-[[2-[2-(1H-tetrazol-5-yl)phenyl]-5-benzoxazolyl]methyl]-2,3,4,5-tetrahydro-4-oxo-5H-1,5-benzothiazepin-3(S)-yl]-3-methylbutanamide.

* * * * *